(12) United States Patent
Köster

(10) Patent No.: US 6,225,450 B1
(45) Date of Patent: May 1, 2001

(54) DNA SEQUENCING BY MASS SPECTROMETRY

(75) Inventor: Hubert Köster, Concord, MA (US)

(73) Assignee: Sequenom, Inc., San Diego, CA (US)

( * ) Notice: Subject to any disclaimer, the term of this patent is extended or adjusted under 35 U.S.C. 154(b) by 0 days.

(21) Appl. No.: 08/481,033

(22) Filed: Jun. 7, 1995

Related U.S. Application Data

(60) Division of application No. 08/178,216, filed on Jan. 6, 1994, now Pat. No. 5,547,835, which is a continuation-in-part of application No. 08/001,323, filed on Jan. 7, 1993, now abandoned.

(51) Int. Cl.[7] ............................. C12Q 1/63; C07H 21/00; C07H 19/04; C07H 21/04

(52) U.S. Cl. .......................... 536/22.1; 435/6; 536/54; 536/24.3; 536/24.33; 536/26.13; 536/26.6; 536/28.52; 536/28.54; 536/28.55; 536/118; 536/122

(58) Field of Search .................... 435/6; 536/26.13, 536/26.6, 28.52, 28.54, 28.55, 54, 118, 122, 24.3, 24.33

(56) References Cited

U.S. PATENT DOCUMENTS

| 4,214,159 | 7/1980 | Hillenkamp et al. ............... 250/288 |
| 4,442,354 | 4/1984 | Hurst et al. ...................... 250/281 |

(List continued on next page.)

FOREIGN PATENT DOCUMENTS

| 0360677 A1 | 3/1990 | (EP) ............... C12Q/1/68 |
| WO 89/09282 | 10/1989 | (WO) ............ C12Q/1/68 |
| WO 89/12694 | 12/1989 | (WO) ............ C12Q/1/68 |
| WO 90/14148 | 11/1990 | (WO) ............ B01D/59/44 |
| WO 92/13629 | 8/1992 | (WO) ............ B01D/59/44 |
| 9411530 | 5/1994 | (WO) . |
| 9416101 | 7/1994 | (WO) . |
| 9421822 | 9/1994 | (WO) . |
| 9507361 | 3/1995 | (WO) . |
| 9629431 | 9/1996 | (WO) . |
| 9632504 | 10/1996 | (WO) . |
| 9636731 | 11/1996 | (WO) . |
| 9636986 | 11/1996 | (WO) . |
| 9636987 | 11/1996 | (WO) . |
| 9708306 | 3/1997 | (WO) . |
| 9716699 | 5/1997 | (WO) . |

(List continued on next page.)

OTHER PUBLICATIONS

Jacobson et al., "Applications of mass spectrometry to DNA fingerprinting and DNA sequencing", *International Symposium on the Forensic Aspects of DNA Analysis*, pp. 1–18, Mar. 29–Apr. 2, 1993.

(List continued on next page.)

*Primary Examiner*—Jezia Riley
(74) *Attorney, Agent, or Firm*—Stephanie L. Seidman; Heller Ehrman White & McAuliffe LLP

(57) ABSTRACT

The invention describes a new method to sequence DNA. The improvements over the existing DNA sequencing technologies are high speed, high throughput, no electrophoresis and gel reading artifacts due to the complete absence of an electrophoretic step, and no costly reagents involving various substitutions with stable isotopes. The invention utilizes the Sanger sequencing strategy and assembles the sequence information by analysis of the nested fragments obtained by base-specific chain termination via their different molecular masses using mass spectrometry, as for example, MALDI or ES mass spectrometry. A flirter increase in throughput can be obtained by introducing mass-modifications in the oligonucleotide primer, chain-terminating nucleoside triphosphates and/or in the chain-elongating nucleoside triphosphates, as well as using integrated tag sequences which allow multiplexing by hybridization tag specific probes with mass differentiated molecular weights.

42 Claims, 36 Drawing Sheets

U.S. PATENT DOCUMENTS

| | | | |
|---|---|---|---|
| 4,515,781 | * 5/1985 | Torrence et al. | 514/46 |
| 4,582,789 | * 4/1986 | Sheldon, III et al. | 435/6 |
| 4,711,955 | * 12/1987 | Ward et al. | 536/29 |
| 4,725,677 | 2/1988 | Köster et al. | 536/27 |
| 4,778,993 | 10/1988 | Waugh | 250/287 |
| 4,920,264 | 4/1990 | Becker | 250/282 |
| 5,003,059 | 3/1991 | Brennan | 536/27 |
| 5,045,694 | 9/1991 | Beavis et al. | 250/287 |
| 5,062,935 | 11/1991 | Schlag et al. | 204/154.41 |
| 5,064,754 | 11/1991 | Mills | 435/6 |
| 5,118,605 | 6/1992 | Urdea | 435/6 |
| 5,118,937 | 6/1992 | Hillenkamp et al. | 250/282 |
| 5,135,870 | 8/1992 | Williams et al. | 436/86 |
| 5,149,625 | 9/1992 | Church et al. | 435/6 |
| 5,202,561 | 4/1993 | Giessmann et al. | 250/281 |
| 5,210,412 | 5/1993 | Levis et al. | 250/288 |
| 5,237,016 | 8/1993 | Ghosh et al. | 525/329.4 |
| 5,242,974 | 9/1993 | Holmes | 525/54.11 |
| 5,288,644 | 2/1994 | Beavis et al. | 436/94 |
| 5,373,156 | 12/1994 | Franzen | 250/288 |
| 5,376,788 | 12/1994 | Standing et al. | 250/288 |
| 5,380,833 | 1/1995 | Urdea et al. | 536/22.1 |
| 5,381,008 | 1/1995 | Tanner et al. | 250/288 |
| 5,382,793 | 1/1995 | Weinberger et al. | 250/288 |
| 5,503,980 | 4/1996 | Cantor | 435/6 |
| 5,510,613 | 4/1996 | Reilly et al. | 250/287 |
| 5,512,439 | 4/1996 | Hornes et al. | 435/6 |
| 5,547,835 | 8/1996 | Köster | 435/6 |
| 5,580,733 | 12/1996 | Levis et al. | 435/6 |
| 5,605,798 | 2/1997 | Köster | 435/6 |
| 5,622,824 | 4/1997 | Köster | 435/6 |
| 5,625,184 | 4/1997 | Vestal et al. | 250/287 |
| 5,627,369 | 5/1997 | Vestal et al. | 250/287 |
| 5,631,134 | 5/1997 | Cantor | 435/6 |
| 5,641,959 | 6/1997 | Holle et al. | 250/287 |
| 5,654,545 | 8/1997 | Holle et al. | 250/287 |
| 5,691,141 | 11/1997 | Köster | 435/6 |
| 5,700,642 | 12/1997 | Monforte | 435/6 |
| 5,742,049 | 4/1998 | Holle et al. | 250/282 |
| 5,760,393 | 6/1998 | Vestal et al. | 250/282 |
| 5,777,324 | 7/1998 | Hillenkamp | 250/288 |
| 5,777,325 | 7/1998 | Weinberger et al. | 250/287 |
| 5,795,714 | 8/1998 | Cantor et al. | 435/6 |
| 5,830,655 | 11/1998 | Monforte et al. | 435/6 |
| 5,864,137 | 1/1999 | Becker et al. | 250/287 |
| 5,869,242 | 2/1999 | Kamb | 435/6 |

FOREIGN PATENT DOCUMENTS

| | | |
|---|---|---|
| 9737041 | 10/1997 | (WO) . |
| 9742348 | 11/1997 | (WO) . |
| 9743617 | 11/1997 | (WO) . |
| 9820019 | 5/1998 | (WO) . |
| 9820020 | 5/1998 | (WO) . |
| 9820166 | 5/1998 | (WO) . |

OTHER PUBLICATIONS

"Time of Flight Mass Spectrometry of DNA for Rapid Sequence Determination. Technical Progress Report, Jul. 31, 1991–Jul. 31, 1992" Arizona State University., Tempe.

Uhlmann et al. "Antisense oligonucleotides: A new therapeutic principle" Chemical Reviews, vol. 90, pp. 543–584, Jun. 1990.*

Leonard et al. "High–resolution structure of mutagenic lesion in DNA" PNAS, vol. 87, pp. 9573–9576, Jun. 1990.*

Fu et al., "A DNA sequencing strategy which requires only five bases of known terminal sequence for priming," Genome Mapping and Sequencing Conference, Cold Spring Harbor Laboratory: May 10 to 14, 1995.

Tang, et al., "Improving mass resolution in MALDI/TOF analysis of DNA", American Society of Mass Spectrometrists Conference: May 21 to 26, 1995.

Andersen, et al., Electrospray ionization and matrix assisted laser desorption/ionization mass spectrometry: Powerful analytical tools in recombinant protein chemistry, *Nature Biotech.* 14:449–457 (1996).

Ardey, Electrospray mass spectrometry, *Spectroscopy Europe*, 4:10–20 (1992).

Arlinghaus et al., "Applications of resonance ionization spectroscopy for semiconductor, environmental and biomedical analysis, and for DNA sequencing", *SPIE*, vol. 1435, *Opt. Methods Ultrasensitive Detect. Anal. Tech. Appl.* pp. 26–35 (1991).

Beck et al., Applications of dioxetane chemiluminescent probes to molecular biology, *Anal. Chem.* 62:2258–2270 (1990).

Beck et al., Chemiluminescent detection of DNA: application for DNA sequencing and hybridization, *Nucl Acids Res* 17:5115–5123 (1989).

Berkenkamp et al., Infrared MALDI mass spectrometry of large nucleic acids, *Science* 281:260–2 (1998).

Braun et al., Detecting *CFTR* gene mutations by using primer oligo base extension and mass spectrometry, *Clinical Chemistry* 43:1151–1158 (1997).

Braun et al., Improved Analysis of Microsatellites Using Mass Spectrometry, *Genomics* 46:18–23(1997).

Broude et al., Enhanced DNA sequencing by hybridization, *Proc. Natl. Acad. Sci. USA* 91:3072–3076 (1994).

Caldwell et al., Mid–infrared matrix assisted laser desorption ionization with a water/glycerol matrix, *Applied Surface Science* 127–129:242–247 (1998).

Covey, et al., The determination of protein, oligonucleotide and peptide molecular weights by ion–spray mass spectrometry, *Rapid Comm. Mass Spectrom.* 2:249–256 (1988).

Crain, Mass spectrometric techniques in nucleic acid research, *Mass Spectrom. Rev.* 9:505–554 (1990).

Eckstein (ed.), *Oligonucleotides and Analogues*, IRL Press, Oxford (1991).

Edmonds et al., Thermospray liquid chromatography–mass spectrometry of nucleosides and of enzymatic hydrolysates of nucleic acids, *Nucleic Acids Research* 13:8197–8206 (1985).

Ehring et al., Photochemical versus thermal mechanisms in matrix–assisted laser desorption/ionization probed by back side desorption, *Rapid Comm in Mass Spect* 10:821–824 (1996).

Frank et al., DNA chain length markers and the influence of base composition on electrophoretic mobility of oligodeoxyribonucleotides in polyacrylamide–gels, *Nucl Acids Res* 6:2069–2087, 1979.

Fu et al., A DNA sequencing strategy that requires only five bases of known terminal sequenec for priming, *Proc. Natl. Acad. Sci. USA* 92:10162–10166 (1995).

Fu et al., Efficient preparation of short DNA sequence ladders potentially suitable for MALDI–TOF DNA sequencing, *Genetic Analysis* 12:137–142 (1996).

Fu et al., Sequencing double–stranded DNA by strand displacement, *Nucl Acids Res* 25:677–679 (1997).

Fu et al., Sequencing exons 5 to 8 of the p53 gene by MALDI–TOF mass spectrometry, *Nat Biotechnol* 16:381–4 (1998).

Ganem et al., Detection of oligonucleotide duplex forms by ion–spray mass spectrometry, *Tetrahedron Letters* 34:1445–1448, (1993).

Gildea et al., A versatile acid–labile linker for modification of synthetic biomolecules, *Tetrahedron Letters* 31:7095–7398 (1990).

Gross et al., Investigations of the metastable decay of DNA under ultraviolet matrix–assisted laser desorption/ionization conditions with post–source–decay analysis and hydrogen/deuterium exchange, *J Amer Soc for Mass Spect* 9:866–878 (1998).

Gruić–Sovulj I. et al., Matrix–assisted laser desorption/ionisation mass spectrometry of transfer ribonucleic acids isolated from yeast, *Nucleic Acids Res.* 25(9):1859–61 (1997).

Hillenkamp and Ehring, Laser desorption mass spectrometry Part 1: Basic mechanisms and techniques, *Mass Spectrometry in the Biological Sciences: A tutorial*, pp. 165–179 (1992).

Hillenkamp, et al., Matrix assisted UV–laser desorption/ionization: A new approtach to mass spectrometry of large biomolecules, *In Biological Mass Spectrometry* (Burlingame and McCloskey, eds.), Elseveir, Amsterdam (1989).

Hsiung et al., A new simpler photoaffinity analogue of peptidyl rRNA, *Nucl Acids Res* 1:1753–1762 (1974).

Huth–Fehre et al., Matrix–assisted laser desorption mass spectrometry of oligodeoxythymidylic acids, *Rapid Comm in Mass Spect* 6:209–213 (1992).

Jacobson, et al. Applications of mass spectrometry to DNA sequencing, *GATA* 8:223–229 (1991).

Ji et al., Two–dimensional electrophoretic analysis of proteins expressed by normal and cancerous human crypts: Application of mass spectrometry to peptide–mass fingerprinting, *Electrophoresis* 15:391–405 (1994).

Juhasz et al., Applications of delayed extraction matrix–assisted laser desorption ionization time–of–flight mass spectrometry to oligonucleotide analysis, *Analy Chem* 68:941–946 (1996).

Jurinke et al., Analysis of ligase chain reaction products via matrix–assisted laser desorption/ionization time–of–flight–mass spectrometry, *Analy Biochem* 237:174–181 (1996).

Jurinke et al., Application of nested PCR and mass spectrometry for DNA–based virus detection: HBV–DNA detected in the majority of isolated anti–HBc positive sera, *Genetic Analysis* 14:97–102 (1998).

Jurinke et al., Detection of hepatitis B virus DNA in serum samples via nested PCR and MALDI–TOF mass spectrometry, *Genetic Analysis* 13:67–71 (1996).

Jurinke et al., Recovery of nucleic acids from immobilized biotin–streptavidin complexes using ammonium hydroxide and applications in MALDI–TOF mass spectrometry, *Anal. Chem.* 69:904–910 (1997).

Kirpekar et al., DNA sequence analysis by MALDI mass spectrometry, *Nucleic Acids Res.* 26:2554–9 (1998).

Köster et al., A strategy for rapid and efficient DNA sequencing by mass spectrometry, *Nature Biotech* 14:1123–1128 (1996).

Köster et al., N–ACYL proecting groups for deoxynucleosides, A quantitative and comparative study, *Tetrahedron* 37:363–369 (1981).

Köster et al., Oligonucleotide synthesis and multiplex DNA sequencing using chemiluminescent detection, *Nucl Acids Res* 24:318–321 (1991).

Köster et al., Polymer support oligonucleotide synthesis—XV[1,2], *Tetrahedron* 40:102–112 (1984).

Köster et al., Some improvements in the synthesis of DNA of biological interest, *Nucl Acids Res* 7:39–59 (1980).

Köster et al., Well–defined insoluble primers for the enzymatic synthesis of oligo– and polynucleotides, *Hoppe–Seyler's Z. Physiol. Chem.* 359:11579–1589 (1978).

Lawrance et al., Megabase–scale mapping of the HLA gene complex by pulsed field gel electrophoresis, *Science* 235:1387–1389 (1987).

Li et al., High–Resolution MALDI Fourier Transform Mass Spectrometry of Oligonucleotides, *Anal Chem* 68:2090–2096 (1996).

Little et al., Detection of RET proto–oncogene codon 634 mutations using mass spectrometry, *J. Mol Med.* 75:745–750 (1997).

Little et al., Direct detection of synthetic and biologically generated double–stranded DNA by MALDI–TOF MS, *J. Mass Spec* 17:1–8 (1997).

Little et al., MALDI on a chip: analysis of arrays of low–femtomole to subfemtomole quantities of synthetic oligonucleotides and DNA diagnostic products dispensed by a piezoelectric pipet, *Anal Chem* 69:4540–4546 (1997).

Little et al., Mass spectrometry from miniaturized arrays for full comparative DNA analysis, *Nature Med* 3:1413–1416 (1997).

Little et al., Verification of 50– to 100–mer DNA and RNA sequences with high–resolution mass spectrometry, *Proc. Natl. Acad. Sci. USA* 92:2318–2322 (1995).

Monforte and Becker, High–throughput DNA analysis by time–of–flight mass spectrometry, *Nature Medicine* 3:360–362 (1997).

Mosca et al., Mass spectrometry and DNA analysis, *Hemoglobin* 17(3):261–268 (1993).

Nordhoff et al., Ion stability of nucleic acids in infrared matrix–assisted laser desorption/ionization mass spectrometry, *Nuc Acids Res.* 21:3347–3357 (1993).

Nordoff et al., Matrix–assisted laser desorption/ionization mass spectrometry of nucleic acids with wavelength in the ultraviolet and infrared, *Rapid Comm. Mass Spect* 6:771–776 (1992).

O'Donnell et al., High–density, covalent attachment of DNA to siliocn wafers for analysis by MALDI–TOF mass spectrometry, *Analytical Chemistry* 69:2438–2443 (1997).

O'Donnell et al., MassArray as an enabling technology for the industrial–scale analysis of DNA, *Genetic Engineering News* 17 (1997).

O'Donnell–Maloney et al., Microfabrication and array technologies for DNA sequencing and diagnostics, *Genetic Analysis: Biomolecular Engineering* 13:151–157 (1996).

Overberg et al., Laser Desorption Mass Spectrometry. Part II Performance and Applications of Matrix–Assisted Laser Desorption/Ionization of Large Biomolecules, *Mass Spectrometry in the Biological Science: A Tutorial* 181–197 (1992).

Pieles et al., Matrix–assisted laser desorption ionization time–of–flight mass spectrometry: a powerful tool for the mass and sequence analysis of natural and modified oligonucleotides, *Nucleic Acids Res.* 21:3191–3196 (1993).

Pomerantz et al., Determination of oligonucleotide composition from mass spectrometrically measured molecular weight, *Am. Soc. Mass Spectrom.* 4:204–09 (1993).

Prome et al., Use of combined mass spectrometry methods for the characterization of a new variant of human hemoglobin: The double mutant hemoglobin villeparisis beta 77(EF1), *J. American Society for Mass Spect* 7(2):163–167 (1996).

Ruppert et al., A filtration method for plasmid isolation using microtiter filter plates, *Anal. Biochem.* 230:130–134 (1995).

Ruppert et al., A rapid and high throughput method for plasmid isolations, Presented: Automation in Mapping and DNA Sequencing Conference, Aug. 31–Sep. 2, 1994.

Ruppert et al., Preparation of plasmid DNA as sequencing templates in a microtiter plate format, Paper presented, Cold Spring Harbor Laboratory Sep. 1994.

Schram, Mass spectrometry of nucleic acid componenents, *Biomed. App. Mass Spectrom.* 34:203–287 (1990).

Sequenom Advances the Industrial Genomics Revolution with the Launch of Its DNA MassArray™Automated Process Line, Press Release: Sep. 28, 1998, http://www.sequenom.com/pressrelease.htm.

Sequenom Reports DNA MassArray™Technology More Sensitive Than Electrophoretic Methods in Detecting Gene Mutations: Automated DNA Analysis System Can Speed Up Microsatellite Analyses, Press Release: Dec. 15, 1997, http://www.sequenom.com/pressrelease.htm.

Sequenom Reports On Use of Its DNA MassArray™Technology to Analyze Genes Associated with Alzheimer's Disease adn Arteriosclerosis: Technology Has Applications in Drug Development, Press Release: Sep. 22, 1997, http://www.sequenom.com/pressrelease.htm.

Sequenom Signs Agreement With Bruker–Franzen Analytik to Develop Mass Spectrometer for DNA Massarray Analysis, Press Release: Jan. 12, 1998, http://www.sequenom.com/pressrelease.htm.

Sequenom Uses DNA MassArray™to Sequence Section of Human Cancer–Related p53 Gene, Press Release: Mar. 27, 1998, http://www.sequenom.com/pressrelease.htm.

Shaler et al., Effect of Impurities on the matrix–assisted laser desorption mass spectra of single–stranded oligodeoxynucleotides, *Anal. Chem.* 68:576–579 (1996).

Siegert et al., Matrix–assisted laser desorption/ionization time–of–flight mass spectrometry for the detection of polymerase hain reaction products containing 7–deasapurine moieties, *Anal. Biochem.* 243:55–65 (1996).

Sinha et al., β–cyanoethyl N, N–dialkylamino/N–morpholinomonochloro phosphoamidites, new phosphitylating agents facilitating ease of deprotection and work–up of synthesized oligonucleotides, *Tetrahedron Lett.* 24:5843–5846 (1983).

Sinha et al., Polymer support oligonucleotide synthesis XVIII: Use of B–cyanoethyl–N, N–dialkylamino–/N–morpholino phosphoramidite of deoxynucleosides for the synthesis of DNA fragments simplifying deprotection and isolation of final product, *Nucleic Acids Res.* 12:4539 (1984).

Siuzdak, The emergence of mass spectrometry in biochemical research, *Proc. Natl. Acad. Sci. USA* 91:11290–11297 (1994).

Smith et al., New Developments in Biochemical Mass Spectrometry: Electrospray Ionization, *Anal. Chem.* 62:882–899 (1990).

Smith et al., Capillary zone electrophoresis–mass spectrometry using an electrospray ionization interface, *Anal. Chem.* 60:436–441 (1988).

Sproat et al., The synthesis of protected 5'–amino–2', 5'–dideoxyribonucleoside–3'–O–phosphoramidites; applications of 5'–amino–oligodeoxyribonucleotides, *Nucleic Acids Res.* 15:6181–6196 (1987).

Tang et al., Matrix–assisted laser desorption/ionization mass spectrometry of immobilized duplex DNA probes, *Nucleic Acids Research* 23:3126–3131 (1995).

Vorm et al., Improved resolution and very high sensitivity in MALDI TOF of matrix surfaces made by fast evaporation, *Anal. Chem.* 66:3281–3287 (1994).

Wu et al., Matrix–assisted Laser Desorption Time–of–flight Mass Spectrometry of Oligonucleotides Using 3–Hydroxypicolinic Acid as an Ultraviolet–sensitive Matrix, *Rapid Comm Mass Spec* 7:142–146 (1993).

Wu et al., Time–of–Flight Mass Spectrometry of Underivatized Single–Stranded DNA Oligomers by Matrix–Assisted Laser Desorption, *Anal. Chem.* 66:1637–1645 (1994).

Yamashita et al., Electrospray ion source. Another variation on the free–jet theme, *J. Phys. Chem.* 88:4451–4459, (1984).

Barrell, B. (1991) "DNA Sequencing: present limitations and prospects for the future" *FASEB Journal* 5: 40–45.

Eckstein, F., ed. (1991) *Oligonucleotides and Analogues: A Practical Approach* Oxford: Oxford University Press, 56–57, 137–139, 256–259.

Hillenkamp, F. et al. (1989) "Matrix Assisted UV–Laser Desorption/Ionization: A New Approach to Mass Spectometry of Large Biomolecules" *Biological Mass Spectrometry,* A.L. Burlingame and J.A. McCloskey (eds.), Amsterdam: Elsevier Science Publishers B.V., 49–60.

Jacobson, K.B. et al. (1991) "Applications of Mass Spectrometry to DNA Sequencing" *GATA* 8(8): 223–229.

Köster, H. et al., "Oligonucleotide Synthesis and Multiplex DNA Sequencing Using Chemiluminescent Detection", *Nucleic Acids Research,* Symposium Series No. 24 (1991), pp. 318–321.

Mizusawa, Saeko et al., "Improvement of the Dideoxy Chain Termination Method of DNA Sequencing by Use of Deoxy–7–Deazaguanosine Triphosphate in Place of dGTP", *Nucleic Acids Research,* vol. 14, No. 3 (1986), pp. 1319–1325.

Nelson, R.W. et al. (1989) "Volatilization of High Molecular Weight DNA by Pulsed Laser Ablation of Frozen Aqueous Solutions" *Science* 246: 1585–1587.

Overberg, A. et al. (1992) "Laser Desorption Mass Spectrometry. Part II Performance and Applications of Matrix–Assisted Laser Desorption/Ionization of Large Biomolecules" in *Mass Spectrometry in the Biological Sciences: A Tutorial,* M.L. Gross (ed.), The Netherlands: Kluwer Publications, 181–197.

Stahl, Stefan et al., "Solid Phase DNA Sequencing Using the Biotin–Avidin System", *Nucleic Acids Research,* vol. 16, No. 7 (1988) pp. 3025–3039.

Trainor, George L., "DNA Sequencing, Automation, and the Human Genome", *Anal. Chem.* vol. 62 (1990) pp. 418–426.

Haglund et al., Marix–assisted laser–desorption mass spectrometry of DNA using an infrared free–electron laser, *SPIE* 1854:117–128 (1993).

Little et al., Identification of apolipoprotein E polymorphisms using temperature cycled primer oligo base extension and mass spectrometry, *Eur J. Clin Chem Clin Biochem* 35:545–548 (1997).

Valaskovic, et al., Attomole–sensitivity electrospray source for large–molecule mass spectrometry, *Anal. Chem.* 67:3802–3805 (1995).

\* cited by examiner

FIG. 2A

| Sequence | Value |
|---|---|
| 5'-dTAACGGTCATTACGGCCATTGACTGTAGGACCTGCATTACATGACTAGCT | 226.23 |
| 5'-dT | 2104.45 |
| 5'-dTAACGGT | 3011.04 |
| 5'-dTAACGGTCAT | 3315.24 |
| 5'-dTAACGGTCATT | 5771.82 |
| 5'-dTAACGGTCATTACGGCCAT | 6076.02 |
| 5'-dTAACGGTCATTACGGCCATT | 7311.82 |
| 5'-dTAACGGTCATTACGGCCATTGACT | 7945.22 |
| 5'-dTAACGGTCATTACGGCCATTGACTGT | 10112.63 |
| 5'-dTAACGGTCATTACGGCCATTGACTGTAGGACCT | 11348.43 |
| 5'-dTAACGGTCATTACGGCCATTGACTGTAGGACCTGCAT | 11652.62 |
| 5'-dTAACGGTCATTACGGCCATTGACTGTAGGACCTGCATT | 12872.42 |
| 5'-dTAACGGTCATTACGGCCATTGACTGTAGGACCTGCATTACAT | 14108.22 |
| 5'-dTAACGGTCATTACGGCCATTGACTGTAGGACCTGCATTACATGACT | 15344.02 |
| 5'-dTAACGGTCATTACGGCCATTGACTGTAGGACCTGCATTACATGACTAGCT | |

FIG. 3A

| Sequence | Mass |
|---|---|
| 5'-dTAACGGTCATTACGGCCATTGACTGTAGGACCTGCATTACATGACTAGCT | 530.43 |
| 5'-dTA | 843.64 |
| 5'-dTAA | 2697.83 |
| 5'-dTAACGGTCA | 3619.43 |
| 5'-dTAACGGTCATTA | 5458.61 |
| 5'-dTAACGGTCATTACGGCCA | 6709.42 |
| 5'-dTAACGGTCATTACGGCCATTGA | 8249.42 |
| 5'-dTAACGGTCATTACGGCCATTGACTGTA | 9221.05 |
| 5'-dTAACGGTCATTACGGCCATTGACTGTAGGA | 11035.22 |
| 5'-dTAACGGTCATTACGGCCATTGACTGTAGGACCTGCA | 11956.82 |
| 5'-dTAACGGTCATTACGGCCATTGACTGTAGGACCTGCATTA | 12559.21 |
| 5'-dTAACGGTCATTACGGCCATTGACTGTAGGACCTGCATTACA | 13505.83 |
| 5'-dTAACGGTCATTACGGCCATTGACTGTAGGACCTGCATTACATGA | 14412.42 |
| 5'-dTAACGGTCATTACGGCCATTGACTGTAGGACCTGCATTACATGACTA | |

FIG. 4A

| Sequence | Mass |
|---|---|
| 5'- dTAACGGTCATTACGGCCATTGACTGTAGGACCTGCATTACATGACTAGCT | 1471.05 |
| 5'- dTAACG | 1800.25 |
| 5'- dTAACGG | 4246.84 |
| 5'- dTAACGGTCATTACG | 4576.05 |
| 5'- dTAACGGTCATTACGG | 6405.23 |
| 5'- dTAACGGTCATTACGGCCATTG | 7641.03 |
| 5'- dTAACGGTCATTACGGCCATTGACTG | 8587.64 |
| 5'- dTAACGGTCATTACGGCCATTGACTGTAG | 8916.85 |
| 5'- dTAACGGTCATTACGGCCATTGACTGTAGG | 10441.84 |
| 5'- dTAACGGTCATTACGGCCATTGACTGTAGGACCTG | 13201.63 |
| 5'- dTAACGGTCATTACGGCCATTGACTGTAGGACCTGCATTACATG | 14750.64 |
| 5'- dTAACGGTCATTACGGCCATTGACTGTAGGACCTGCATTACATGACTAG | |

FIG. 5A

| Sequence | Value |
|---|---|
| 5'- dTAACGGTCATTACGGCCCATTGACTGTAGGACCTGCATTACATGACTAGCT | 1141.84 |
| 5'- dTAAC | 2393.63 |
| 5'- dTAACGGTC | 3917.63 |
| 5'- dTAACGGTCATTAC | 4865.23 |
| 5'- dTAACGGTCATTACGGC | 5154.42 |
| 5'- dTAACGGTCATTACGGCC | 7007.62 |
| 5'- dTAACGGTCATTACGGCCCATTGAC | 9519.25 |
| 5'- dTAACGGTCATTACGGCCCATTGACTGTAGGAC | 9808.43 |
| 5'- dTAACGGTCATTACGGCCCATTGACTGTAGGACC | 10731.02 |
| 5'- dTAACGGTCATTACGGCCCATTGACTGTAGGACCTGC | 12255.02 |
| 5'- dTAACGGTCATTACGGCCCATTGACTGTAGGACCTGCATTAC | 13804.02 |
| 5'- dTAACGGTCATTACGGCCCATTGACTGTAGGACCTGCATTACATGACTAGC | 15039.82 |

FIG. 6

| sequence | ddT | ddA | ddG | ddC |
|---|---|---|---|---|
| T | 226.23 | | | |
| A | | 530.43 | | |
| A | | 843.64 | | |
| C | | | | 1141.84 |
| G | | | 1471.05 | |
| G | | | 1800.25 | |
| T | 2104.45 | | | |
| C | | | | 2393.63 |
| A | | 2697.83 | | |
| T | 3011.04 | | | |
| T | 3315.24 | | | |
| A | | 3619.43 | | |
| C | | | | 3917.63 |
| G | | | 4246.84 | |
| G | | | 4576.05 | |
| C | | | | 4865.23 |
| C | | | | 5154.42 |
| A | | 5458.61 | | |
| T | 5771.82 | | | |
| T | 6076.02 | | | |
| G | | | 6405.23 | |
| A | | 6709.42 | | |
| C | | | | 7007.62 |
| T | 7311.82 | | | |
| G | | | 7641.03 | |
| T | 7945.22 | | | |
| A | | 8249.42 | | |
| G | | | 8587.64 | |
| G | | | 8916.85 | |
| A | | 9221.05 | | |
| C | | | | 9519.25 |
| C | | | | 9808.43 |
| T | 10112.63 | | | |
| G | | | 10441.84 | |
| C | | | | 10731.02 |
| A | | 11035.22 | | |
| T | 11348.43 | | | |
| T | 11652.62 | | | |
| A | | 11956.82 | | |
| C | | | | 12255.02 |
| A | | 12559.21 | | |
| T | 12872.42 | | | |
| G | | | 13201.63 | |
| A | | 13505.83 | | |
| C | | | | 13804.02 |
| T | 14108.22 | | | |
| A | | 14412.42 | | |
| G | | | 14750.64 | |
| C | | | | 15039.82 |
| T | 15344.02 | | | |

$\eta = 1 - 50$
M = H, OH, XR, Halogen, $N_3$

FIG. 7B

| | $M^1$ | $M^2$ | $M^3$ | $M^5$ |
|---|---|---|---|---|
| Type Ia (base modified DNA) | OH | XR/Hal | OH | H |
| Type Ib (base modified RNA) | OH | XR/Hal | OH | OH |
| Type IIa (5'-modified DNA) | XR/Hal | H | OH | H |
| Type IIb (5'-modified RNA) | XR/Hal | H | OH | OH |
| Type III (3'-modified) | OH | H | OH | XR/Hal |
| Type IVa (P-modified DNA) | OH | H | XR | H |
| Type IVb (P-modified RNA) | OH | H | XR | OH |

FIG. 8B

| | $M^2$ | $M^3$ | $M^4$ | $M^5$ |
|---|---|---|---|---|
| Type A (DNA-Termination) | XR | OH | H | H |
| Type B (DNA-Termination) | H | OH | H | XR |
| Type C (DNA-Termination) | H | XR | H | H |
| Type D (RNA-Termination) | XR | OH | OH | H |
| Type E (RNA-Termination) | H | OH | OH | XR |
| Type F (RNA-Termination) | H | XR | OH | H |

Alkyl: $-(CH_2)_r-CH_3$ e.g. $-CH_3, -C_2H_5$, and branched e.g. $-CH(CH_3)_2$ $ICH_2(CH_2)_r-O-H$ 2,3-Epoxy-1-propanol $-(CH_2)_m-CH_2-O-H$ $-(CH_2)_m-CH_2-O-$Alkyl $-(CH_2CH_2NH)_m-CH_2CH_2-NH_2$ $-[NH-(CH_2)_r-NH-\underset{\underset{O}{\|}}{C}-(CH_2)_r-\underset{\underset{O}{\|}}{C}-]_m-NH-(CH_2)_r-NH-\underset{\underset{O}{\|}}{C}-(CH_2)_r-\underset{\underset{O}{\|}}{C}-OH$ $-[NH-(CH_2)_r-\underset{\underset{O}{\|}}{C}-]_m-NH-(CH_2)_r-\underset{\underset{O}{\|}}{C}-OH$ $-[NH-CHY-\underset{\underset{O}{\|}}{C}-]_m-NH-CHY-\underset{\underset{O}{\|}}{C}-OH$ $-[O-(CH_2)_r-\underset{\underset{O}{\|}}{C}-]_m-O-(CH_2)_r-\underset{\underset{O}{\|}}{C}-OH$

-S-

-Si(Alkyl)$_3$

-Halogen

-N$_3$ $-CH_2F, -CHF_2, -CF_3$ m = 0, 1 - 200
r = 1 - 20

FIG.11
e.g. for dT-Termination:
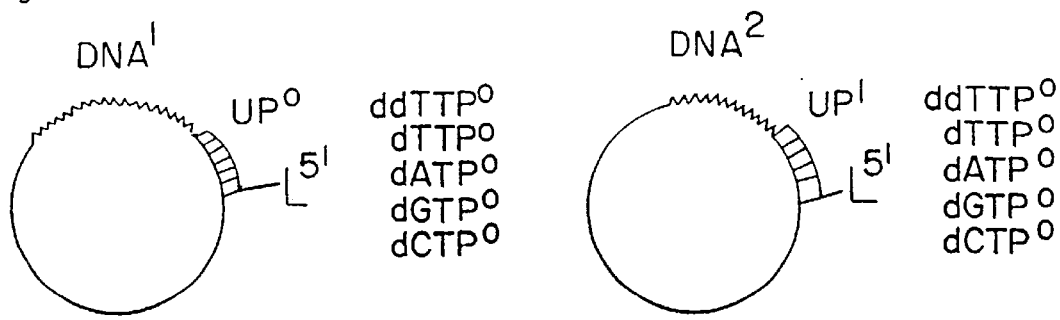
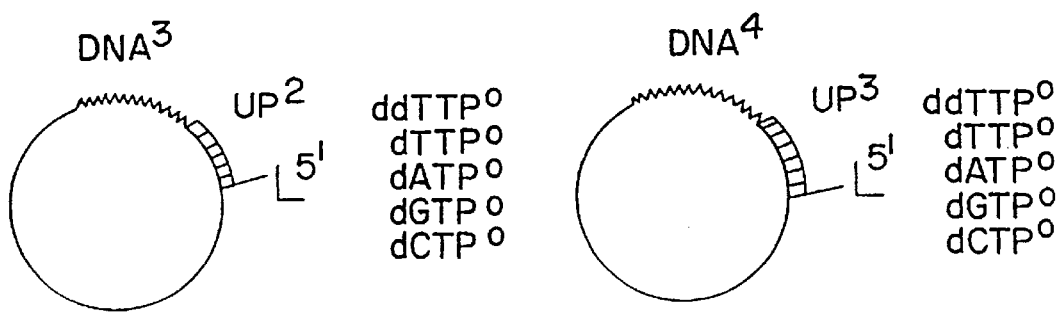
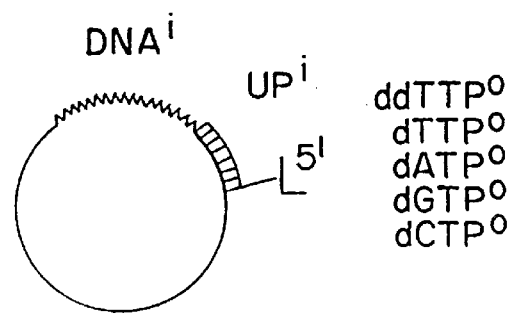

FIG. 12
e.g. for dT-Termination:
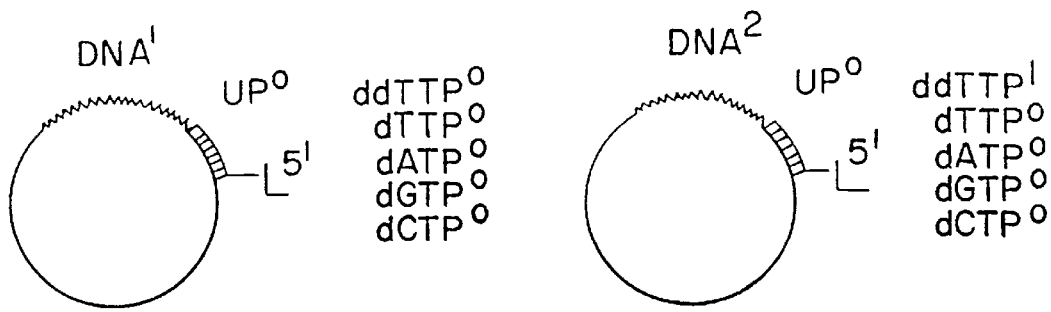
for signal amplification elongation with:
e.g. for dT-Termination:
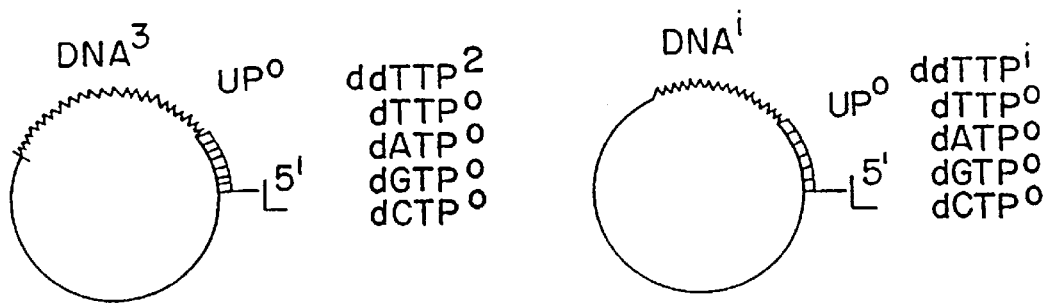
for signal amplification elongation with:

FIG. 19
$\text{(P)} \sim A^{\ominus} \quad B^{\oplus} \sim NA$          $\sim$ : Spacer
NA: Nucleic Acid (Sanger Nested Fragments)
(P)—      :     Polymer Support
$A^{\ominus}$      :     $-CO_2^{\ominus}$, $-SO_3^{\ominus}$, $PO_4^{2-}$, $SiO_4^{3-}$,
                   $PO_3^{2-}$, $SiO_3^{3-}$
R = Alkyl, Aralkyl
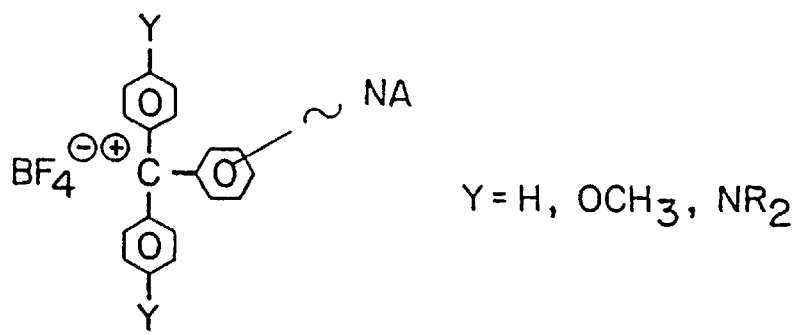
Y = H, $OCH_3$, $NR_2$
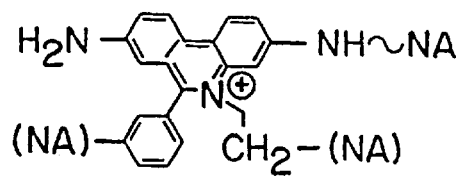
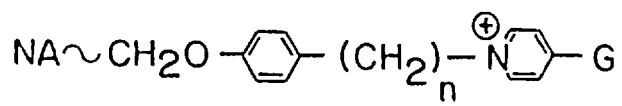
n = 1-10
G = $NO_2$, CN, F, CL, Br

FIG. 20A
Ⓟ∿A        D∿NA        ∿ : Spacer
Ⓟ—    :    Polymer Support
NA    :    Nucleic Acid (Sanger Nested Fragments)
A    :    Charge Transfer Acceptor
D    :    Charge Transfer Donator
D:    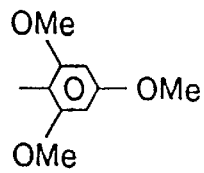    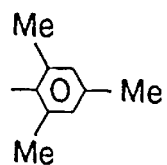    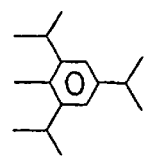
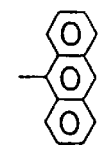    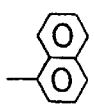    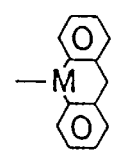
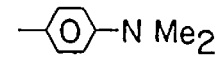
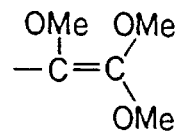
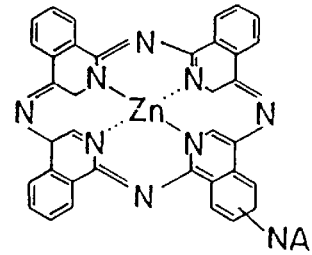
Zinc Phthalocyanine
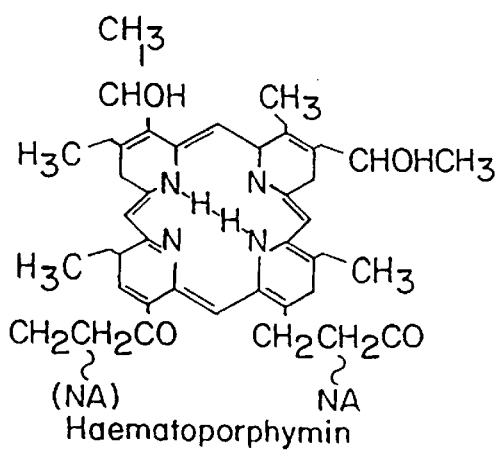
Haematoporphymin

FIG. 20B
A:
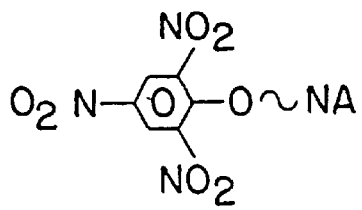
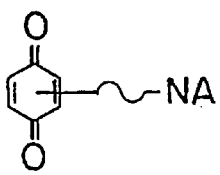
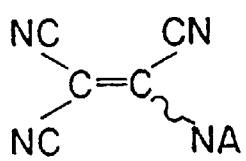
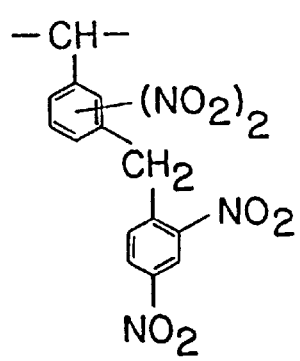
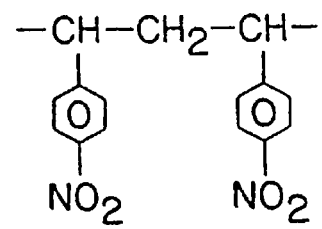
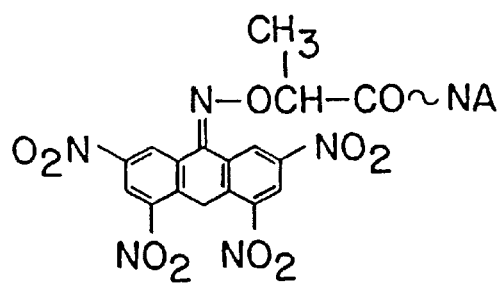

FIG. 21
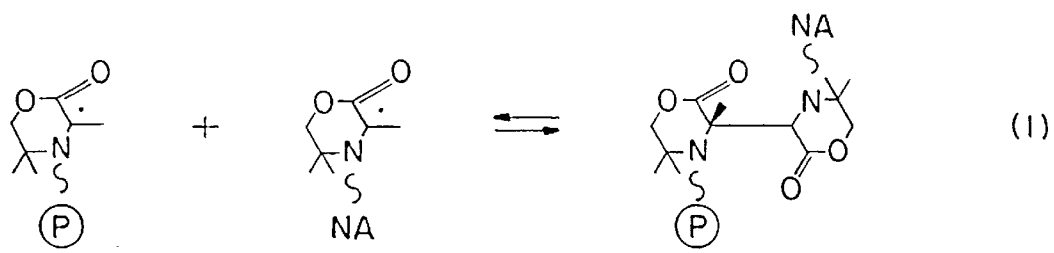 (1)
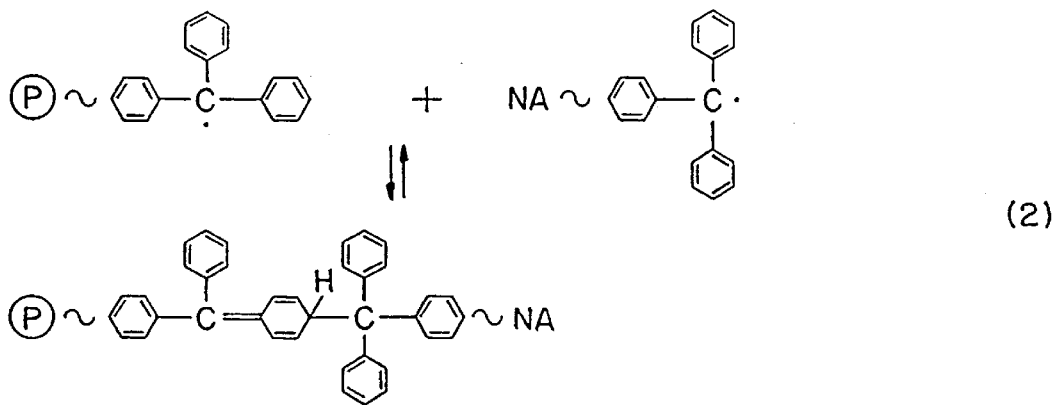 (2)
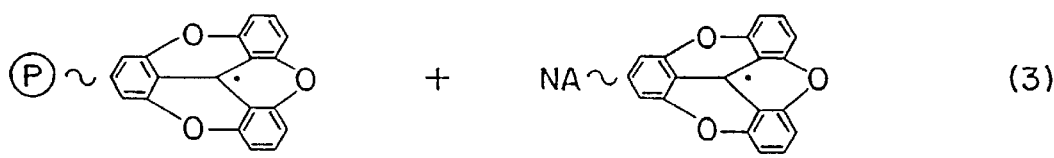 (3)
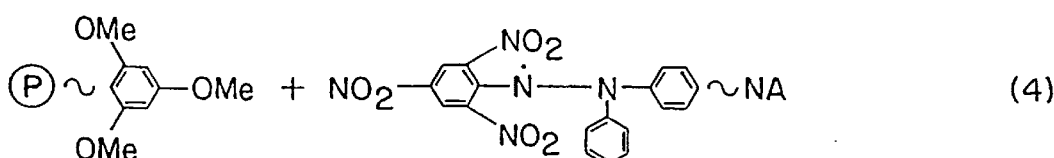 (4)
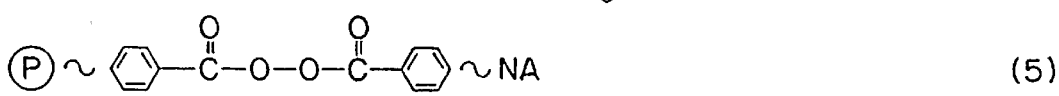 (5)
 (6)
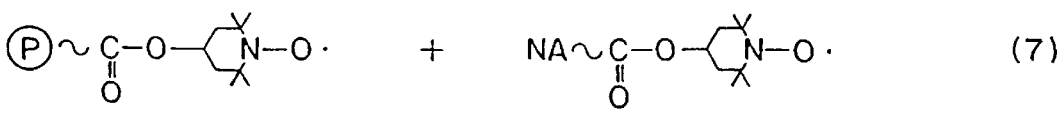 (7)

FIG. 22
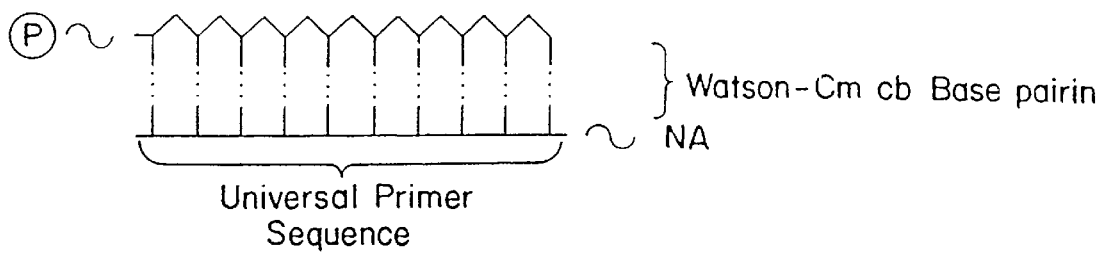
Universal Primer Sequence } Watson-Cm cb Base pairin ~NA
NA : Nucleic Acid (Nested Sanger Fragments)
(P)— : Polymer Support
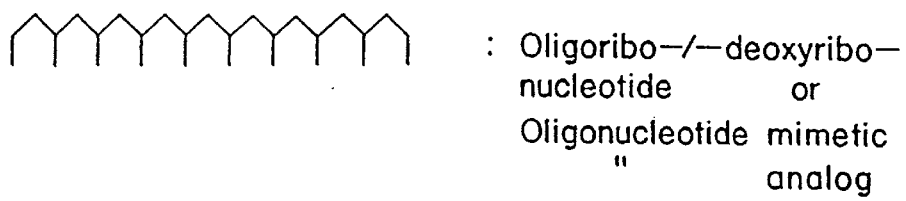 : Oligoribo-/-deoxyribo-nucleotide or Oligonucleotide mimetic " analog
FIG. 23
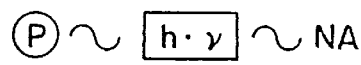
(P) : POLYMER SUPPORT
~ : SPACER
[h·ν] : PHOTOCLEAVABLE BOND
NA : NUCLEIC ACID (NESTED SANGER FRAGMENTS)

DNA SEQUENCING BY MASS SPECTROMETRY

This application is a divisional application of Ser. No. 08/178,216 filed on Jan. 6, 1994, now U.S. Pat. No. 5,547,835, which is a continuation in part of Ser. No. 08/001,323 filed Jan. 7, 1993 (abandoned). The contents of all of the aforementioned application(s) are hereby incorporated by reference.

BACKGROUND OF THE INVENTION

Since the genetic information is represented by the sequence of the four DNA building blocks deoxyadenosine-(dpA), deoxyguanosine-(dpG), deoxycytidine-(dpC) and deoxythymidine-5'-phosphate (dpT), DNA sequencing is one of the most fundamental technologies in molecular biology and the life sciences in general. The ease and the rate by which DNA sequences can be obtained greatly affects related technologies such as development and production of new therapeutic agents and new and useful varieties of plants and microorganisms via recombinant DNA technology. In particular, unraveling the DNA sequence helps in understanding human pathological conditions including genetic disorders, cancer and AIDS. In some cases, very subtle differences such as a one nucleotide deletion, addition or substitution can create serious, in some cases even fatal, consequences. Recently, DNA sequencing has become the core technology of the Human Genome Sequencing Project (e.g., J. E. Bishop and M. Waldholz, 1991, *Genome: The Story of the Most Astonishing Scientific Adventure of Our Time—The Attempt to Map All the Genes in the Human Body*, Simon & Schuster, New York). Knowledge of the complete human genome DNA sequence will certainly help to understand, to diagnose, to prevent and to treat human diseases. To be able to tackle successfully the determination of the approximately 3 billion base pairs of the human genome in a reasonable time frame and in an economical way, rapid, reliable, sensitive and inexpensive methods need to be developed, which also offer the possibility of automation. The present invention provides such a technology.

Recent reviews of today's methods together with future directions and trends are given by Barrell (*The FASEB Journal* 5, 40–45 (1991)), and Trainor (*Anal. Chem.* 62, 418–26 (1990)).

Currently, DNA sequencing is performed by either the chemical degradation method of Maxam and Gilbert (*Methods in Enzymology* 65, 499–560 (1980)) or the enzymatic dideoxynucleotide termination method of Sanger et al. (*Proc. Natl. Acad. Sci. USA* 74, 5463–67 (1977)). In the chemical method, base specific modifications result in a base specific cleavage of the radioactive or fluorescently labeled DNA fragment. With the four separate base specific cleavage reactions, four sets of nested fragments are produced which are separated according to length by polyacrylamide gel electrophoresis (PAGE). After autoradiography, the sequence can be read directly since each band (fragment) in the gel originates from a base specific cleavage event Thus, the fragment lengths in the four "ladders" directly translate into a specific position in the DNA sequence.

In the enzymatic chain termination method, the four base specific sets of DNA fragments are formed by starting with a primer/template system elongating the primer into the unknown DNA sequence area and thereby copying the template and synthesizing a complementary strand by DNA polymerases, such as Klenow fragment of *E. coli* DNA polymerase I, a DNA polymerase from *Thermus aquaticus*, Taq DNA polymerase, or a modified T7 DNA polymerase, Sequenase (Tabor et al., *Proc. Natl. Acad. Sci. USA* 84, 4767–4771 (1987)), in the presence of chain-terminating reagents. Here, the chain-terminating event is achieved by incorporating into the four separate reaction mixtures in addition to the four normal deoxynucleoside triphosphates, dATP, dGTP, dTTP and dCTP, only one of the chain-terminating dideoxynucleoside triphosphates, ddATP, ddGTP, ddTTP or ddCTP, respectively, in a limiting small concentration. The four sets of resulting fragments produce, after electrophoresis, four base specific ladders from which the DNA sequence can be determined.

A recent modification of the Sanger sequencing strategy involves the degradation of phosphorothioate-containing DNA fragments obtained by using alpha-thio dNTP instead of the normally used ddNTPs during the primer extension reaction mediated by DNA polymerase (Labeit et al., *DNA* 5, 173–177 (1986); Amersham, PCT-Application GB86/00349; Eckstein et al., *Nucleic Acids Res.* 16, 9947 (1988)). Here, the four sets of base-specific sequencing ladders are obtained by limited digestion with exonuclease III or snake venom phosphodiesterase, subsequent separation on PAGE and visualization by radioisotopic labeling of either the primer or one of the dNTPs. In a further modification, the base-specific cleavage is achieved by alkylating the sulphur atom in the modified phosphodiester bond followed by a heat treatment (Max-Planck-Gesellschaft, DE 3930312 A1). Both methods can be combined with the amplification of the DNA via the Polymerase Chain Reaction (PCR).

On the upfront end, the DNA to be sequenced has to be fragmented into sequencable pieces of currently not more than 500 to 1000 nucleotides. Starting from a genome, this is a multi-step process involving cloning and subcloning steps using different and appropriate cloning vectors such as YAC, cosmids, plasmids and M13 vectors (Sambrook et al., *Molecular Cloning: A Laboratory Manual*, Cold Spring Harbor Laboratory Press, 1989). Finally, for Sanger sequencing, the fragments of about 500 to 1000 base pairs are integrated into a specific restriction site of the replicative form I (RF I) of a derivative of the M13 bacteriophage (Vieria and Messing, *Gene* 19, 259 (1982)) and then the double-stranded form is transformed to the single-stranded circular form to serve as a template for the Sanger sequencing process having a binding site for a universal primer obtained by chemical DNA synthesis (Sinha, Biernat, McManus and Köster, *Nucleic Acids Res.* 2, 4539–57 (1984); U.S. Pat. No. 4,725,677 upstream of the restriction site into which the unknown DNA fragment has been inserted. Under specific conditions, unknown DNA sequences integrated into supercoiled double-stranded plasmid DNA can be sequenced directly by the Sanger method (Chen and Seeburg, *DNA* 4, 165–170 (1985)) and Lim et al., *Gene Anal. Techn.* 5, 32–39 (1988), and, with the Polymerase Chain Reaction (PCR) (*PCR Protocols: A Guide to Methods and Applications*, Innis et al., editors, Academic Press, San Diego (1990)) cloning or subcloning steps could be omitted by directly sequencing off chromosomal DNA by first amplifying the DNA segment by PCR and then applying the Sanger sequencing method (Innis et al., *Proc. Natl. Acad. Sci. USA* 85, 9436–9440 (1988)). In this case, however, the DNA sequence in the interested region most be known at least to the extent to bind a sequencing primer.

In order to be able to read the sequence from PAGE, detectable labels have to be used in either the primer (very often at the 5'-end) or in one of the deoxynucleoside triphosphates, dNTP. Using radioisotopes such as $^{32}P$, $^{33}P$, or $^{35}S$ is still the most frequently used technique. After PAGE, the gels are exposed to X-ray films and silver grain exposure is analyzed. The use of radioisotopic labeling creates several problems. Most labels useful for autoradiographic detection of sequencing fragments have relatively short half-lives which can limit the useful time of the labels. The emission high energy beta radiation, particularly from $^{32}$P, can lead to breakdown of the products via radiolysis so that the sample should be used very quickly after labeling. In addition, high energy radiation can also cause a deterioration of band sharpness by scattering. Some of these problems can be reduced by using the less energetic isotopes such as $^{33}$P or $^{35}$S (see, e.g., Ornstein et al., Biotechniques 3, 476 (1985)). Here, however, longer exposure times have to be tolerated. Above all, the use of radioisotopes poses significant health risks to the experimentalist and, in heavy sequencing projects, decontamination and handling the radioactive waste are other severe problems and burdens.

In response to the above mentioned problems related to the use of radioactive labels, non-radioactive labeling techniques have been explored and, in recent years, integrated into partly automated DNA sequencing procedures. All these improvements utilize the Sanger sequencing strategy. The fluorescent label can be tagged to the primer (Smith et al., Nature 321, 674–679 (1986) and EPO Patent No. 87300998.9; Du Pont De Nemours EPO Application No. 0359225; Ansorge et al. J. Biochem. Biophys. Methods 13, 325–32 (1986)) or to the chain-terminating dideoxynucloside triphosphates (Prober et al. Science 238, 336–41 (1987); Applied Biosystems, PCT Application WO 91/05060). Based on either labeling the primer or the ddNTP, systems have been developed by Applied Biosystems (Smith et al., Science 235, G89 (1987); U.S. Pat. Nos. 570,973 and 689,013), Du Pont De Nemours (Prober et al. Science 23, 336–341 (1987); U.S. Pat. Nos. 881,372 and 57,566), Pharmacia-LKB (Ansorge et al. Nucleic Acids Res. 15, 4593–4602 (1987) and EMBL Patent Application DE P3724442 and P3805808.1) and Hitachi (JP 1-90844 and DE 4011991 A1). A somewhat similar approach was developed by Brumbaugh et al. (Proc. Natl. Sci. USA 85, 5610–14 (1988) and U.S. Pat. No. 4,729,947). An improved method for the Du Pont system using two electrophoretic lanes with two different specific labels per lane is described (PCT Application W092/02635). A different approach uses fluorescently labeled avidin and biotin labeled primers. Here, the sequencing ladders ending with biotin are reacted during electrophoresis with the labeled avidin which results in the detection of the individual sequencing bands (Brumbaugh et al, U.S. Pat. No. 594,676).

More recently even more sensitive non-radioactive labeling techniques for DNA using chemiluminescence triggerable and amplifyable by enzymes have been developed (Beck, O'Keefe, Coull and Köster, Nucleic Acids Res. 17, 5115–5123 (1989) and Beck and Köster, Anal. Chem. 62, 2258–2270 (1990)). These labeling methods were combined with multiplex DNA sequencing (Church et al. Science 240, 185–188 (1988) to provide for a strategy aimed at high throughput DNA sequencing (Köster et al., Nucleic Acids Res. Symposium Ser. No. 24, 318–321 (1991), University of Utah, PCT Application No. WO 90/15883); this strategy still suffers from the disadvantage of being very laborious and difficult to automate.

In an attempt to simplify DNA sequencing, solid supports have been introduced. In most cases published so far, the template strand for sequencing (with or without PCR amplification) is immobilized on a solid support most frequently utilizing the strong biotin-avidin/streptavidin interaction (Orion-Yhtymä Oy, U.S. Pat. No. 277,643; M. Ulhlen et al. Nucleic Acids Res. 16, 3025–38 (1988); Cemu Bioteknik, PCT Application No. WO 89/09282 and Medical Research Council, GB, PCT Application No. WO 92/03575). The primer extension products synthesized on the immobilized template strand are purified of enzymes, other sequencing reagents and by-products by a washing step and then released under denaturing conditions by loosing the hydrogen bonds between the Watson-Crick base pairs and subjected to PAGE separation. In a different approach, the primer extension products (not the template) from a DNA sequencing reaction are bound to a solid support via biotin/avidin (Du Pont De Nemours, PCT Application WO 91/11533). In contrast to the above mentioned methods, here, the interaction between biotin and avidin is overcome by employing denaturing conditions (formamide/EDTA) to release the primer extension products of the sequencing reaction from the solid support for PAGE separation. As solid supports, beads, (e.g., magnetic beads (Dynabeads) and Sepharose beads), filters, capillaries, plastic dipsticks (e.g., polystyrene strips) and microtiter wells are being proposed.

All methods discussed so far have one central step in common: polyacrylamide gel electrophoresis (PAGE). In many instances, this represents a major drawback and limitation for each of these methods. Preparing a homogeneous gel by polymerization, loading of the samples, the electrophoresis itself, detection of the sequence pattern (e.g., by autoradiography), removing the gel and cleaning the glass plates to prepare another gel are very laborious and time-consuming procedures. Moreover, the whole process is error-prone, difficult to automate, and, in order to improve reproducibility and reliability, highly trained and skilled personnel are required. In the case of radioactive labeling, autoradiography itself can consume from hours to days. In the case of fluorescent labeling, at least the detection of the sequencing bands is being performed automatically when using the laser-scanning devices integrated into commercial available DNA sequencers. One problem related to the fluorescent labeling is the influence of the four different base-specific fluorescent tags on the mobility of the fragments during electrophoresis and a possible overlap in the spectral bandwidth of the four specific dyes reducing the discriminating power between neighboring bands, hence, increasing the probability of sequence ambiguities. Artifacts are also produced by base-specific interactions with the polyacrylamide gel matrix (Frank and Köster, Nucleic Acids Res. 6, 2069 (1979)) and by the formation of secondary structures which result in "band compressions" and hence do not allow one to read the sequence. This problem has, in part, been overcome by using 7-deazadeoxyguanosine triphosphates (Barr et al., Biotechniques 4, 428 (1986)). However, the reasons for some artifacts and conspicuous bands are still under investigation and need further improvement of the gel electrophoretic procedure.

A recent innovation in electrophoresis is capillary zone electrophoresis (CZE) (Jorgenson et al., J. Chromatography 352, 337 (1986); Gesteland et al., Nucleic Acids Res. 18, 1415–1419 (1990)) which, compared to slab gel electrophoresis (PAGE), significantly increases the resolution of the separation, reduces the time for an electrophoretic run and allows the analysis of very small samples. Here, however, other problems arise due to the miniaturization of the whole system such as wall effects and the necessity of highly sensitive on-line detection methods. Compared to PAGE, another drawback is created by the fact that CZE is only a "one-lane" process, whereas in PAGE samples in multiple lanes can be electrophoresed simultaneously.

Due to the severe limitations and problems related to having PAGE as an integral and central part in the standard DNA sequencing protocol, several methods have been proposed to do DNA sequencing without an electrophoretic step. One approach calls for hybridization or fragmentation sequencing (Bains, *Biotechnology* 10, 757–58 (1992) and Mirzabekov et al., *FEBS Letters* 256, 118–122 (1989)) utilizing the specific hybridization of known short oligonucleotides (e.g., octadeoxynucleotides which gives 65,536 different sequences) to a complementary DNA sequence. Positive hybridization reveals a short stretch of the unknown sequence. Repeating this process by performing hybridizations with all possible octadeoxynucleotides should theoretically determine the sequence. In a completely different approach, rapid sequencing of DNA is done by unilaterally degrading one single, immobilized DNA fragment by an exonuclease in a moving flow stream and detecting the cleaved nucleotides by their specific fluorescent tag via laser excitation (Jett et al.,*J. Biomolecular Structure & Dynamics* 7, 301–309, (1989); United States Department of Energy, PCT Application No. WO 89/03432). In another system proposed by Hyman (*Anal. Biochem.* 174, 423–436 (1988)), the pyrophosphate generated when the correct nucleotide is attached to the growing chain on a primer-template system is used to determine the DNA sequence. The enzymes used and the DNA are held in place by solid phases (DEAE-Sepharose and Sepharose) either by ionic interactions or by covalent attachment In a continuous flow-through system, the amount of pyrophosphate is determined via bioluminescence (luciferase). A synthesis approach to DNA sequencing is also used by Tsien et al. (PCT Application No. WO 91/06678). Here, the incoming dNTP's are protected at the 3'-end by various blocking groups such as acetyl or phosphate groups and are removed before the next elongation step, which makes this process very slow compared to standard sequencing methods. The template DNA is immobilized on a polymer support. To detect incorporation, a fluorescent or radioactive label is additionally incorporated into the modified dTP's. The same patent application also describes an apparatus designed to automate the process.

Mass spectrometry, in general, provides a means of "weighing" individual molecules by ionizing the molecules in vacuo and making them "fly" by volatilization. Under the influence of combinations of electric and magnetic fields, the ions follow trajectories depending on their individual mass (m) and charge (z). In the range of molecules with low molecular weight, mass spectrometry has long been part of the routine physical-organic repertoire for analysis and characterization of organic molecules by the determination of the mass of the parent molecular ion. In addition, by arranging collisions of this parent molecular ion with other particles (e.g., argon atoms), the molecular ion is fragmented forming secondary ions by the so-called collision induced dissociation (CID). The fragmentation pattern/pathway very often allows the derivation of detailed structural information. Many applications of mass spectrometric methods in the known in the art, particularly in biosciences, and can be found summarized in *Methods in Enzymology,* Vol. 193: "Mass Spectrometry" (J. A. McCloskey, editor), 1990, Academic Press, New York.

Due to the apparent analytical advantages of mass spectrometry in providing high detection sensitivity, accuracy of mass measurements, detailed structural information by CID in conjunction with an MS/MS configuration and speed, as well as on-line data transfer to a computer, there has been considerable interest in the use of mass spectrometry for the structural analysis of nucleic acids. Recent reviews summarizing this field include K. H. Schram, "Mass Spectrometry of Nucleic Acid Components, Biomedical Applications of Mass Spectrometry" 34, 203–287 (1990); and P. F. Crain, "Mass Spectrometric Techniques in Nucleic Acid Research," *Mass Spectrometry Reviews* 9, 505–554 (1990). The biggest hurdle to applying mass spectrometry to nucleic acids is the difficulty of volatilizing these very polar biopolymers. Therefore, "sequencing" has been limited to low molecular weight synthetic oligonucleotides by determining the mass of the parent molecular ion and through this, confirming the already known sequence, or alternatively, confirming the known sequence through the generation of secondary ions (fragment ions) via CID in an MS/MS configuration utilizing, in particular, for the ionization and volatilization, the method of fast atomic bombardment (FAB mass spectrometry) or plasma desorption (PD mass spectrometry). As an example, the application of FAB to the analysis of protected dimeric blocks for chemical synthesis of oligodeoxynucleotides has been described (Köster et al. *Biomedical Environmental Mass Spectrometry* 14, 111–116 (1987)).

Two more recent ionization/desorption techniques are electrospray/ionspray (ES) and matrix-assisted laser desorption/ionization (MALDI). ES mass spectrometry has been introduced by Fenn et al. (*J. Phys. Chem.* 88, 4451–59 (1984); PCT Application No. WO 90/14148) and current applications are summarized in recent review articles (R. D. Smith et al., *Anal. Chem.* 62, 882–89 (1990) and B. Ardrey, Electrospray Mass Spectrometry, *Spectroscopy Europe,* 4, 10–18 (1992)). The molecular weights of the tetradecanucleotide d(CATGCCATGGCATG) (SEQ ID NO:1) (Covey et al. "The Determination of Protein, Oligonucleotide and Peptide Molecular Weights by Ionspray Mass Spectrometry," *Rapid Communications in Mass Spectrometry,* 2, 249–256 (1988)), of the 21-mer d(AAATTGTGCACATCCTGCAGC) (SEQ ID NO:2) and without giving details of that of a tRNA with 76 nucleotides (*Methods in Enzymology,* 193, "Mass Spectrometry" (McCloskey, editor), p. 425, 1990, Academic Press, New York) have been published. As a mass analyzer, a quadrupole is most frequently used. The determination of molecular weights in femtomole amounts of sample is very accurate due to the presence of multiple ion peaks which all could be used for the mass calculation.

MALDI mass spectrometry, in contrast, can be particularly attractive when a time-of-flight (TOF) configuration is used as a mass analyzer. The MALDI-TOF mass spectrometry has been introduced by Hillenkamp et al. ("Matrix Assisted UV-Laser Desorption/Ionization: A New Approach to Mass Spectrometry of Large Biomolecules," *Biological Mass Spectrometry* (Burlingame and McCloskey, editors), Elsevier Science Publishers, Amsterdam, pp. 49–60, 1990.) Since, in most cases, no multiple molecular ion peaks are produced with this technique, the mass spectra, in principle, look simpler compared to ES mass spectrometry. Although DNA molecules up to a molecular weight of 410,000 daltons could be desorbed and volatilized (Williams et a., "Volatilization of High Molecular Weight DNA by Pulsed Laser Ablation of Frozen Aqueous Solutions," *Science,* 246, 1585–87 (1989)), this technique has so far only been used to determine the molecular weights of relatively small oligonucleotides of known sequence, e.g., oligothymidylic acids up to 18 nucleotides (Huth-Fehre-et al., "Matrix-Assisted Laser Desorption Mass Spectrometry of Oligodeoxythymidylic Acids," *Rapid Communications in Mass Spectrometry,* 6, 209–13 (1992)) and a double-stranded DNA of 28 base pairs (Williams et al., "Time-of-Flight Mass Spectrometry of Nucleic Acids by Laser Ablation and Ionization from a Frozen Aqueous Matrix," *Rapid Communications in Mass Spectrometry*, 4, 348–351 (1990)). In one publication (Huth-Fehre et al., 1992, supra), it was shown that a mixture of all the oligothymidylic acids from n=12 to n=18 nucleotides could be resolved.

In U.S. Pat. No. 5,064,754, RNA transcripts extended by DNA both of which are complementary to the DNA to be sequenced are prepared by incorporating NTP's, dNTP's and, as terminating nucleotides, ddNTP's which are substituted at the 5'-position of the sugar moiety with one or a combination of the isotopes $^{12}C$, $^{13}C$, $^{14}C$, $^{1}H$, $^{2}H$, $^{3}H$, $^{16}O$, $^{17}O$ and $^{18}O$. The polynucleotides obtained are degraded to 3'-nucleotides, cleaved at the N-glycosidic linkage and the isotopically labeled 5'-functionality removed by periodate oxidation and the resulting formaldehyde species determined by mass spectrometry. A specific combination of isotopes serves to discriminate base-specifically between internal nucleotides originating from the incorporation of NTP's and dNTP's and terminal nucleotides caused by linking ddNTP's to the end of the polynucleotide chain. A series of RNA/DNA fragments is produced, and in one embodiment, separated by electrophoresis, and, with the aid of the so-called matrix method of analysis, the sequence is deduced.

In Japanese Patent No. 59-131909, an instrument is described which detects nucleic acid fragments separated either by electrophoresis, liquid chromatography or high speed gel filtration. Mass spectrometric detection is achieved by incorporating into the nucleic acids atoms which normally do not occur in DNA such as S, Br, I or Ag, Au, Pt, Os, Hg. The method, however, is not applied to sequencing of DNA using the Sanger method. In particular, it does not propose a base-specific correlation of such elements to an individual ddNTP.

PCT Application No. WO 89/12694 (Brennan et al., *Proc. SPIE-Int, Soc. Opt. Eng.* 1206, (*New Technol. Cytom. Mol. Biol.*), pp. 60–77 (1990); and Brennan, U.S. Pat. No. 5,003,059) employs the Sanger methodology for DNA sequencing by using a combination of either the four stable isotopes $^{32}S$, $^{33}S$, $^{34}S$, $^{36}S$ or $^{35}Cl$, $^{37}Cl$, $^{79}Br$, $^{81}Br$ to specifically label the chain-terminating ddNTP's. The sulfur isotopes can be located either in the base or at the alpha-position of the triphosphate moiety whereas the halogen isotopes are located either at the base or at the 3'-position of the sugar ring. The sequencing reaction mixtures are separated by an electrophoretic technique such as CZE, transferred to a combustion unit in which the sulfur isotopes of the incorporated ddNTP's are transformed at about 900° C. in an oxygen atmosphere. The $SO_2$ generated with masses of 64, 65, 66 or 68 is determined on-line by mass spectrometry using, e.g., as mass analyzer, a quadrupole with a single ion-multiplier to detect the ion current.

A similar approach is proposed in U.S. Pat. No. 5,002,868 (Jacobson et al., *Proc. SPIE-Int. Soc. Opt. Eng.* 1435, (*Opt. Methods Ultrasensitive Detect. Anal. Tech. Appl.*), 26–35 (1991)) using Sanger sequencing with four ddNTP's specifically substituted at the alpha-position of the triphosphate moiety with one of the four stable sulfur isotopes as described above and subsequent separation of the four sets of nested sequences by tube gel electrophoresis. The only difference is the use of resonance ionization spectroscopy (RIS) in conjunction with a magnetic sector mass analyzer as disclosed in U.S. Pat. No. 4,442,354 to detect the sulfur isotopes corresponding to the specific nucleotide terminators, and by this, allowing the assignment of the DNA sequence.

EPO Patent Applications No. 0360676 A1 and 0360677 A1 also describe Sanger sequencing using stable isotope substitutions in the ddNTP's such as D, $^{13}C$, $^{15}N$, $^{17}O$, $^{18}O$, $^{32}S$, $^{33}S$, $^{34}S$, $^{36}S$, $^{19}F$, $^{35}Cl$, $^{37}Cl$, $^{79}Br$, $^{81}Br$ and $^{127}I$ or functional groups such as $CF_3$ or $Si(CH_3)_3$ at the base, the sugar or the alpha position of the triphosphate moiety according to chemical functionality. The Sanger sequencing reaction mixtures are separated by tube gel electrophoresis. The effluent is converted into an aerosol by the electrospray/thermospray nebulizer method and then atomized and ionized by a hot plasma (7000 to 8000° K) and analyzed by a simple mass analyzer. An instrument is proposed which enables one to automate the analysis of the Sanger sequencing reaction mixture consisting of tube electrophoresis, a nebulizer and a mass analyzer.

The application of mass spectrometry to perform DNA sequencing by the hybridization/fragment method (see above) has been recently suggested (Bains, "DNA Sequencing by Mass Spectrometry: Outline of a Potential Future Application," *Chimicaoggi* 9, 13–16 (1991)).

SUMMARY OF THE INVENTION

The invention describes a new method to sequence DNA. The improvements over the existing DNA sequencing technologies include high speed, high throughput, no required electrophoresis (and, thus, no gel reading artifacts due to the complete absence of an electrophoretic step), and no costly reagents involving various substitutions with stable isotopes. The invention utilizes the Sanger sequencing strategy and assembles the sequence information by analysis of the nested fragments obtained by base-specific chain termination via their different molecular masses using mass spectrometry, for example, MALDI or ES mass spectrometry. A further increase in throughput can be obtained by introducing mass modifications in the oligonucleotide primer, the chain-terminating nucleoside triphosphates and/or the chain-elongating nucleoside triphosphates, as well as using integrated tag sequences which allow multiplexing by hybridization of tag specific probes with mass differentiated molecular weights.

BRIEF DESCRIPTION OF THE FIGURES

FIG. 2A shows the Sanger sequencing products using ddTTP as terminating deoxynucleoside triphosphate of a hypothetical DNA fragment of 50 nucleotides (SEQ ID NO:3) in length with approximately equally balanced base composition. The molecular masses of the various chain terminated fragments are given.

FIGS. 3A and 3B show, in analogy to FIGS. 2A and 2B, data for the same model sequence (SEQ ID NO:3) with ddATP as chain terminator.

FIGS. 4A and 4B show data, analogous to FIGS. 2A and 2B when ddGTP is used as a chain terminator for the same model sequence (SEQ ID NO:3).

FIGS. 5A and 5B illustrate the results obtained where chain termination is performed with ddCTP as a chain terminator, in a similar way as shown in FIGS. 2A and 2B for the same model sequence (SEQ ID NO:3).

FIG. 6 summarizes the results of FIGS. 2A to 5B, showing the correlation of molecular weights of the nested four fragment families to the DNA sequence (SEQ ID NO:3).

FIGS. 7A and 7B illustrate the general structure of mass-modified sequencing nucleic acid primers or tag sequencing probes for either Sanger DNA or Sanger RNA sequencing.

FIGS. 8A and 8B show the general structure for the mass-modified triphosphates for either Sanger DNA or Sanger RNA sequencing. General formulas of the chain-elongating and the chain-terminating nucleoside triphosphates are demonstrated.

FIG. 10 illustrates similar linking chemistries as shown in FIG. 8 and depicts various mass modifying moieties (R).

FIG. 11 outlines how multiplex mass spectrometric sequencing can work using the mass-modified nucleic acid primer (UP).

FIG. 12 shows the process of multiplex mass spectrometric sequencing employing mass-modified chain-elongating and/or terminating nucleoside triphosphates.

FIG. 19 illustrates various linking chemistries between the solid support (P) and the nucleic acid primer (NA) through a strong electrostatic interaction.

FIGS. 20A and 20B illustrate various linking chemistries between the solid support (P) and the nucleic acid primer (NA) through a charge transfer complex of a charge transfer acceptor (A) and a charge transfer donor (I).

FIG. 21 and illustrates various linking chemistries between the solid support (P) and the nucleic acid primer (NA) through a stable organic radical.

FIG. 22 illustrates a possible linking chemistry between the solid support (P) and the nucleic acid primer (NA) through Watson-Crick base pairing.

FIG. 23 illustrates linking the solid support (P) and the nucleic acid primer (NA) through a photolytically cleavable bond.

DETAILED DESCRIPTION OF THE INVENTION

Figure 1:
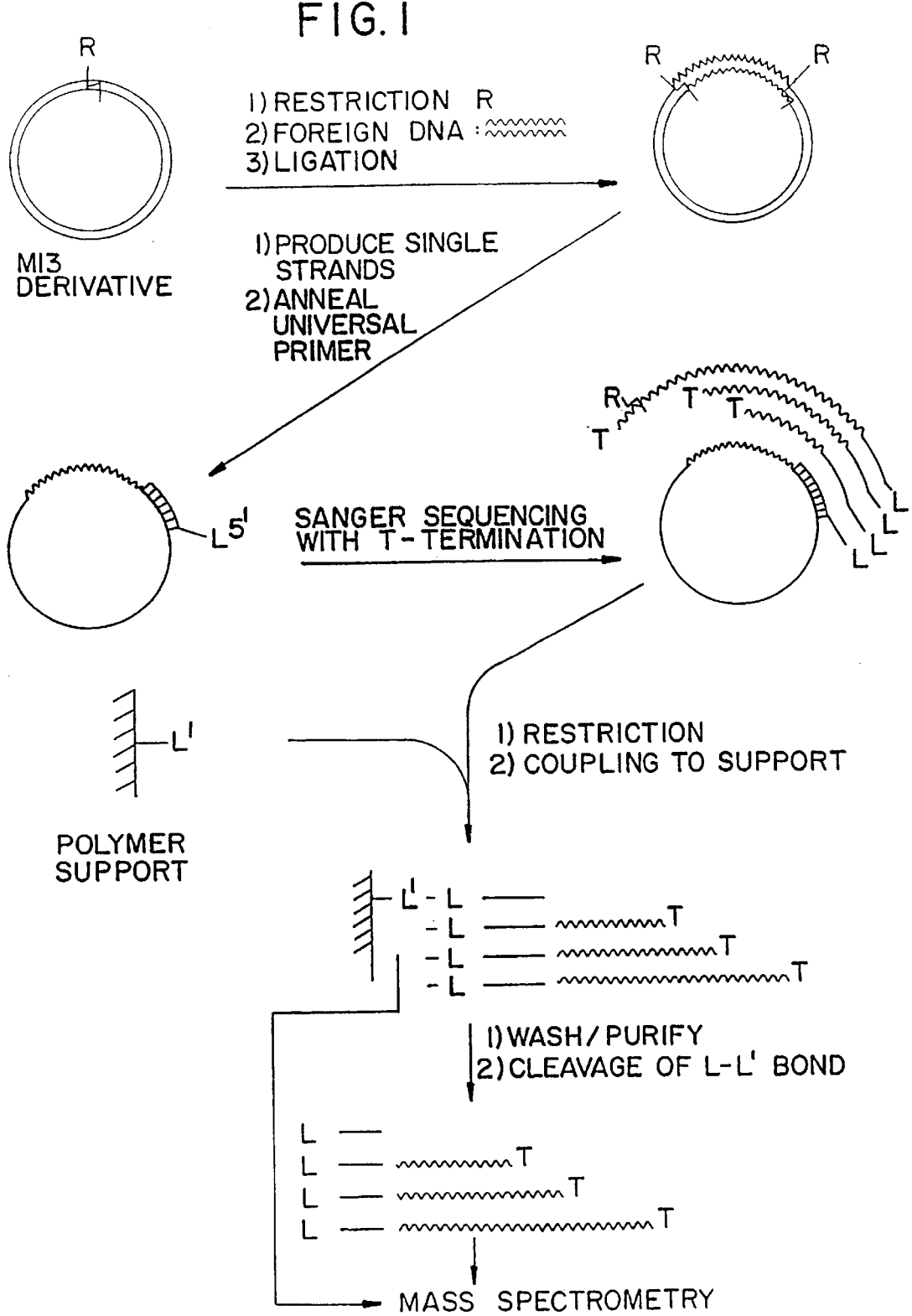
FIG. 1 is a representation of a process to generate the samples to be analyzed by mass spectrometry. This process entails insertion of a DNA fragment of unknown sequence into a cloning vector such as derivatives of M13, pUC or phagemids; transforming the double-stranded form into the single-stranded form; performing the four Sanger sequencing reactions; linking the base-specifically terminated nested fragment family temporarily to a solid support; removing by a washing step all by-products; conditioning the nested DNA or RNA fragments by, for example, cation-ion exchange or modification reagent and presenting the immobilized nested fragments either directly to mass spectrometric analysis or cleaving the purified fragment family off the support and evaporating the cleavage reagent.
Figure 2B:
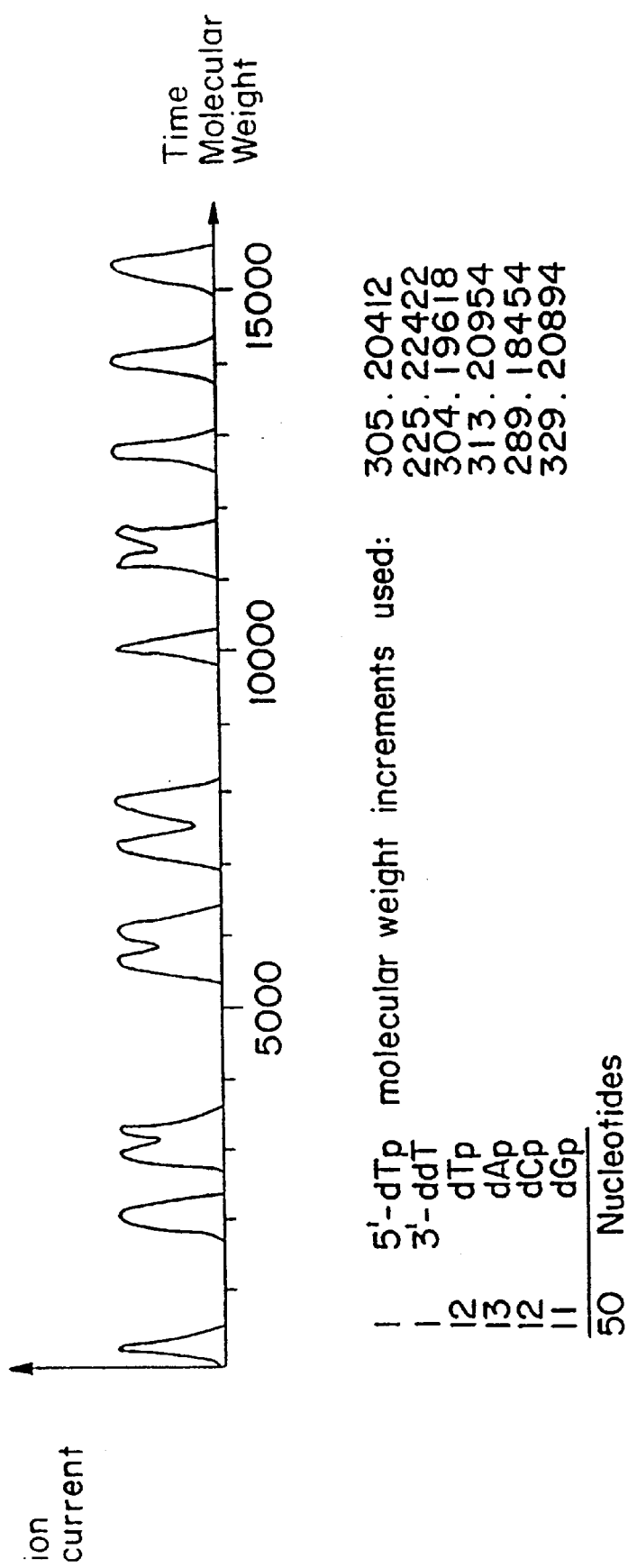
FIG. 2B shows an idealized mass spectrum of such a DNA fragment mixture.
Figure 3B:
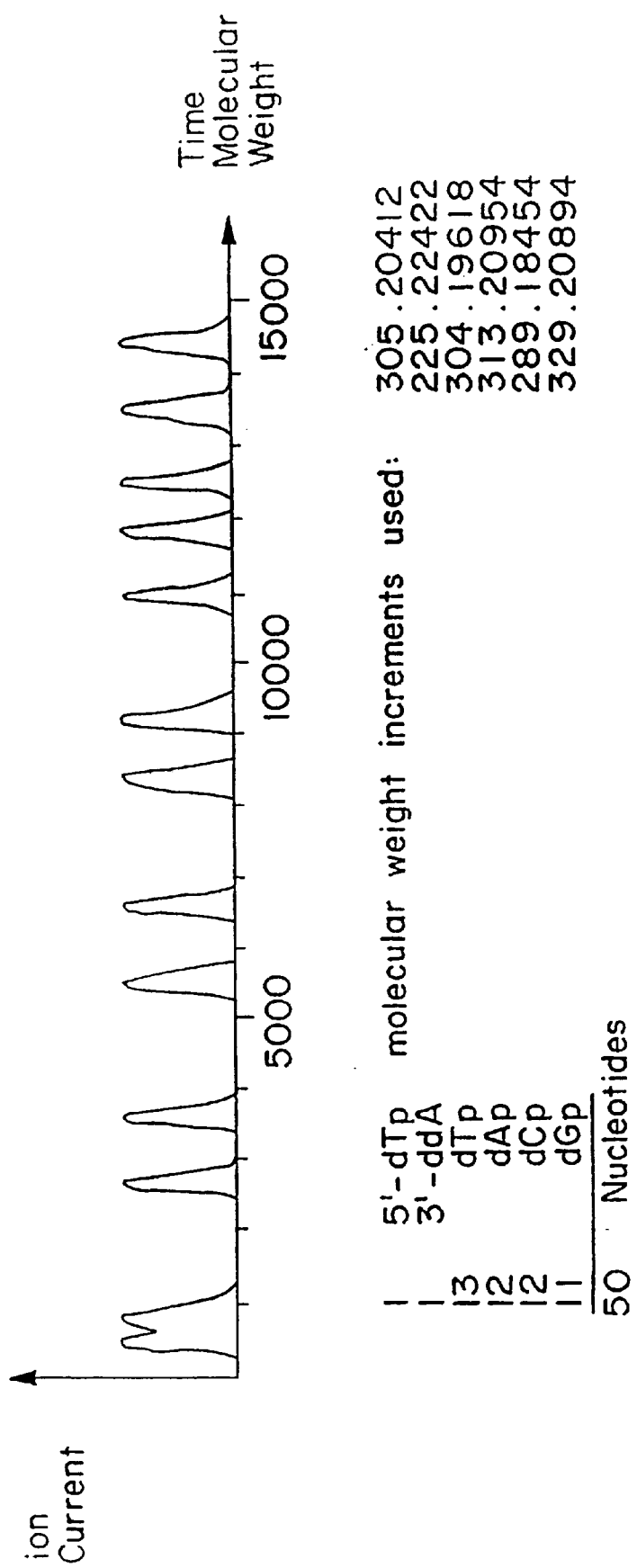
Figure 4B:
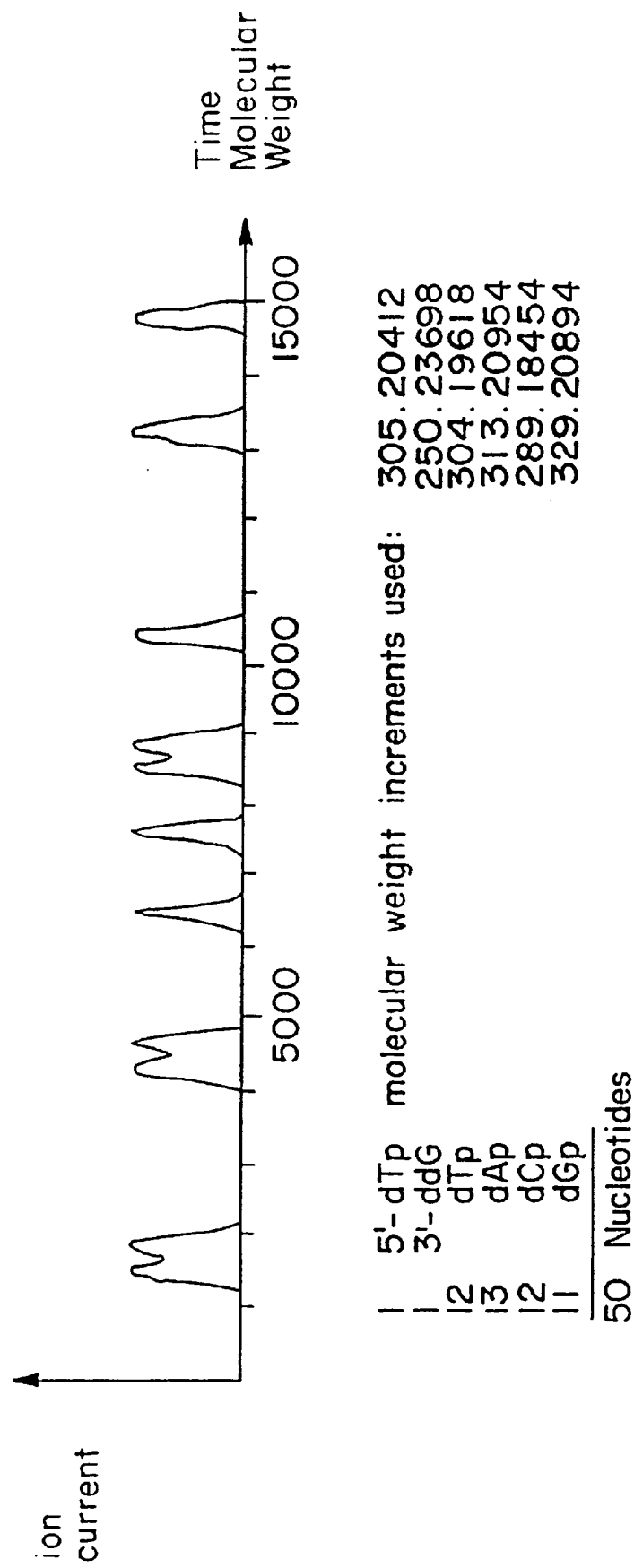
Figure 5B:
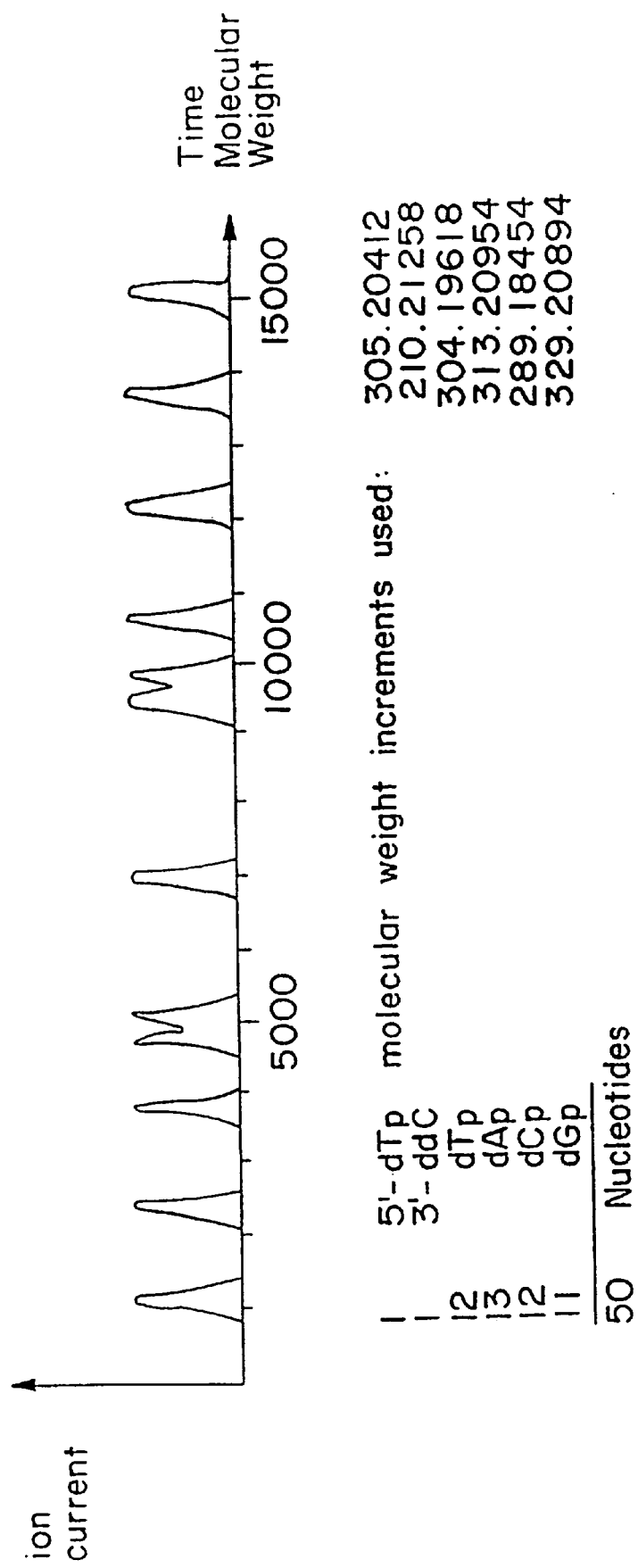

This invention describes an improved method of sequencing DNA. In particular, this invention employs mass spectrometry, such as matrix-assisted laser desorption/ionization (MALDI) or electrospray (ES) mass spectrometry (MS), to analyze the Sanger sequencing reaction mixtures.

In Sanger sequencing, four families of chain-terminated fragments are obtained. The mass difference per nucleotide addition is 289.19 for dpC, 313.21 for dpA, 329.21 for dpG and 304.2 for dpT, respectively.

In one embodiment, through the separate determination of the molecular weights of the four base-specifically terminated fragment families, the DNA sequence can be assigned via superposition (e.g., interpolation) of the molecular weight peaks of the four individual experiments. In another embodiment, the molecular weights of the four specifically terminated fragment families can be determined simultaneously by MS, either by mixing the products of all four reactions run in at least two separate reaction vessels (i.e., all run separately, or two together, or three together) or by running one reaction having all four chain-terminating nucleotides (e.g., a reaction mixture comprising-dTTP, ddTTP, dATP, ddATP, dCTP, ddCTP, dGTP, ddGTP) in one reaction vessel. By simultaneously analyzing all four base-specifically terminated reaction products, the molecular weight values have been, in effect, interpolated. Comparison of the mass difference measured between fragments with the known masses of each chain-terminating nucleotide allows the assignment of sequence to be carried out. In some instances, it may be desirable to mass modify, as discussed below, the chain-terminating nucleotides so as to expand the difference in molecular weight between each nucleotide. It will be apparent to those skilled in the art when mass-modification of the chain-terminating nucleotides is desirable and can depend, for instance, on the resolving ability of the particular spectrometer employed. By way of example, it may be desirable to produce four chain-terminating nucleotides, ddTTP, $ddCTP^1$, $ddATP^2$ and $ddGTP^3$ where $ddCTP^1$, $ddATP^2$ and $ddGTP^3$ have each been mass-modified so as to have molecular weights resolvable from one another by the particular spectrometer being used.

The terms chain-elongating nucleotides and chain-terminating nucleotides are well known in the art. For DNA, chain-elongating nucleotides include 2'-deoxyribonucleotides and chain-terminating nucleotides include 2',3'-dideoxyribonucleotides. For RNA, chain-elongating nucleotides include ribonucelotides and chain-terminating nucleotides include 3'-deoxyribonucleotides. The term nucleotide is also well known in the art. For the purposes of this invention, nucleotides include nucleoside mono-, di-, and triphosphates. Nucleotides also include modified nucleotides such as phosphorothioate nucleotides.

Since mass spectrometry is a serial method, in contrast to currently used slab gel electrophoresis which allows several samples to be processed in parallel, in another embodiment of this invention, a further improvement can be achieved by multiplex mass spectrometric DNA sequencing to allow simultaneous sequencing of more than one DNA or RNA fragment. As described in more detail below, the range of about 300 mass units between one nucleotide addition can be utilized by employing either mass-modified nucleic acid sequencing primers or chain-elongating and/or terminating nucleoside triphosphates so as to shift the molecular weight of the base-specifically terminated fragments of a particular DNA or RNA species being sequenced in a predetermined manner. For the first time, several sequencing reactions can be mass spectrometrically analyzed in parallel. In yet another embodiment of this invention, multiplex mass spectrometric DNA sequencing can be performed by mass modifying the fragment families through specific oligonucleotides (tag probes) which hybridize to specific tag sequences within each of the fragment families. In another embodiment, the tag probe can be covalently attached to the individual and specific tag sequence prior to mass spectrometry.

In one embodiment of the invention, the molecular weight values of at least two base-specifically terminated fragments are determined concurrently using mass spectrometry. The molecular weight values of preferably at least five and more preferably at least ten base-specifically terminated fragments are determined by mass spectrometry. Also included in the invention are determinations of the molecular weight values of at least 20 base-specifically terminated fragments and at least 30 base-specifically terminated fragments. Further, the nested base-specifically terminated fragments in a specific set can be purified of all reactants and by-products but are not separated from one another. The entire set of nested base-specifically terminated fragments is analyzed concurrently and the molecular weight values are determined. At least two base-specifically terminated fragments are analyzed concurrently by mass spectrometry when the fragments are contained in the same sample.

In general, the overall mass spectrometric DNA sequencing process will start with a library of small genomic fragments obtained after first randomly or specifically cutting the genomic DNA into large pieces which then, in several subcloning steps, are reduced in size and inserted into vectors like derivatives of M13 or pUC (e.g., M13mp18 or M13mp19) (see FIG. 1). In a different approach, the fragments inserted in vectors, such as M13, are obtained via subcloning starting with a cDNA library. In yet another approach, the DNA fragments to be sequenced are generated by the polymerase chain reaction (e.g., Higuchi et al., "A General Method of in vitro Preparation and Mutagenesis of DNA Fragments: Study of Protein and DNA Interactions," *Nucleic Acids Res.*, 16, 7351–67 (1988)). As is known in the art, Sanger sequencing can start from one nucleic acid primer (UP) binding to the plus-strand or from another nucleic acid primer binding to the opposite minus-strand. Thus, either the complementary sequence of both strands of a given unknown DNA sequence can be obtained (providing for reduction of ambiguity in the sequence determination) or the length of the sequence information obtainable from one clone can be extended by generating sequence information from both ends of the unknown vector-inserted DNA fragment.

The nucleic acid primer carries, preferentially at the 5'-end, a linking functionality, L, which can include a spacer of sufficient length and which can interact with a suitable functionality, L', on a solid support to form a reversible linkage such as a photocleavable bond. Since each of the four Sanger sequencing families starts with a nucleic acid primer (L-UP; FIG. 1) this fragment family can be bound to the solid support by reacting with functional groups, L', on the surface of a solid support and then intensively washed to remove all buffer salts, triphosphates, enzymes, reaction by-products, etc. Furthermore, for mass spectrometric analysis, it can be of importance at this stage to exchange the cation at the phosphate backbone of the DNA fragments in order to eliminate peak broadening due to a heterogeneity in the cations bound per nucleotide unit. Since the L-L' linkage is only of a temporary nature with the purpose to capture the nested Sanger DNA or RNA fragments to properly condition them for mass spectrometric analysis, there are different chemistries which can serve this purpose. In addition to the examples given in which the nested fragments are coupled covalently to the solid support, washed, and cleaved off the support for mass spectrometric analysis, the temporary linkage can be such that it is cleaved under the conditions of mass spectrometry, i.e., a photocleavable bond such as a charge transfer complex or a stable organic radical. Furthermore, the linkage can be formed with L' being a quaternary ammonium group (some examples are given in FIG. 19). In this case, preferably, the surface of the solid support carries negative charges which repel the negatively charged nucleic acid backbone and thus facilitates desorption. Desorption will take place either by the heat created by the laser pulse and/or, depending on L,' by specific absorption of laser energy which is in resonance with the L' chromophore (see, e.g., examples given in FIG. 19). The functionalities, L and L', can also form a charge transfer complex and thereby form the temporary L-L' linkage. Various examples for appropriate functionalities with either acceptor or donator properties are depicted without limitation in FIG. 20. Since in many cases the "charge-transfer band" can be determined by UV/vis spectrometry (see e.g. *Organic Charge Transfer Complexes* by R. Foster, Academic Press, 1969), the laser energy can be tuned to the corresponding energy of the charge-transfer wavelength and, thus, a specific desorption off the solid support can be initiated. Those skilled in the art will recognize that several combinations can serve this purpose and that the donor functionality can be either on the solid support or coupled to the nested Sanger DNA/RNA fragments or vice versa.

In yet another approach, the temporary linkage L-L' can be generated by homolytically forming relatively stable radicals as exemplified in FIG. 21. In example 4 of FIG. 21, a combination of the approaches using charge-transfer complexes and stable organic radicals is shown. Here, the nested Sanger DNA/RNA fragments are captured via the formation of a charge transfer complex. Under the influence of the laser pulse, desorption (as discussed above) as well as ionization will take place at the radical position. In the other examples of FIG. 21 under the influence of the laser pulse, the L-L' linkage will be cleaved and the nested Sanger DNA/RNA fragments desorbed and subsequently ionized at the radical position formed. Those skilled in the art will recognize that other organic radicals can be selected and that, in relation to the dissociation energies needed to homolytically cleave the bond between them, a corresponding laser wavelength can be selected (see e.g. *Reactive Molecules* by C. Wentrup, John Wiley & Sons, 1984). In yet another approach, the nested Sanger DNA/RNA fragments are captured via Watson-Crick base pairing to a solid support-bound oligonucleotide complementary to either the sequence of the nucleic acid primer or the tag oligonucleotide sequence (see FIG. 22). The duplex formed will be cleaved under the influence of the laser pulse and desorption can be initiated. The solid support-bound base sequence can be presented through natural oligoribo- or oligodeoxyribonucleotide as well as analogs (e.g. thio-modified phosphodiester or phosphotriester backbone) or employing oligonucleotide mimetics such as PNA analogs (see e.g. Nielsen et al., *Science*, 254, 1497 (1991)) which render the base sequence less susceptible to enzymatic degradation and hence increases overall stability of the solid support-bound capture base sequence. With appropriate bonds, L-L', a cleavage can be obtained directly with a laser tuned to the energy necessary for bond cleavage. Thus, the immobilized nested Sanger fragments can be directly ablated during mass spectrometric analysis.

To increase mass spectrometric performance, it may be necessary to modify the phosphodiester backbone prior to MS analysis. This can be accomplished by, for example, using alpha-thio modified nucleotides for chain elongation and termination. With alkylating agents such as akyliodides, iodoacetamide, β-iodoethanol, 2,3-epoxy-1-propanol (see FIG. 10), the monothio phosphodiester bonds of the nested Sanger fragments are transformed into phosphotriester bonds. Multiplexing by mass modification in this case is obtained by mass-modifying the nucleic acid primer (UP) or the nucleoside triphosphates at the sugar or the base moiety. To those skilled in the art, other modifications of the nested Sanger fragments can be envisioned. In one embodiment of the invention, the linking chemistry allows one to cleave off the so-purified nested DNA enzymatically, chemically or physically. By way of example, the L-L' chemistry can be of a type of disulfide bond (chemically cleavable, for example, by mercaptoethanol or dithioerythrol), a biotin/streptavidin system, a heterobifunctional derivative of a trityl ether group (Köster et al, "A Versatile Acid-Labile Linker for Modification of Synthetic Biomolecules," *Tetrahedron Letters* 31, 7095 (1990)) which can be cleaved under mildly acidic conditions, a levulinyl group cleavable under almost neutral conditions with a hydrazinium/acetate buffer, an arginine—arginine or lysine—lysine bond cleavable by an endopeptidase enzyme like trypsin or a pyrophosphate bond cleavable by a pyrophosphatase, a photocleavable bond which can be, for example, physically cleaved and the like (see, e.g., FIG. 23). Optionally, another cation exchange can be performed prior to mass spectrometric analysis. In the instance that an enzyme-cleavable bond is utilized to immobilize the nested fragments, the enzyme used to cleave the bond can serve as an internal mass standard during MS analysis.

The purification process and/or ion exchange process can be carried out by a number of other methods instead of, or in conjunction with, immobilization on a solid support. For example, the base-specifically terminated products can be separated from the reactants by dialysis, filtration (including ultrafiltration), and chromatography. Likewise, these techniques can be used to exchange the cation of the phosphate backbone with a counter-ion which reduces peak broadening.

The base-specifically terminated fragment families can be generated by standard Sanger sequencing using the Large Klenow fragment of *E. coli*DNA polymerase I, by Sequenase, Taq DNA polymerase and other DNA polymerases suitable for this purpose, thus generating nested DNA fragments for the mass spectrometric analysis. It is, however, part of this invention that base-specifically terminated RNA transcripts of the DNA fragments to be sequenced can also be utilized for mass spectrometric sequence determination. In this case, various RNA polymerases such as the SP6 or the T7 RNA polymerase can be used on appropriate vectors containing, for example, the SP6 or the T7 promoters (e.g. Axelrod et al, "Transcription from Bacteriophage T7 and SP6 RNA Polymerase Promoters in the Presence of 3'-Deoxyribonucleoside 5'-triphosphate Chain Terminators," *Biochemistry* 24, 5716–23 (1985)). In this case, the unknown DNA sequence fragments are inserted downstream from such promoters. Transcription can also be initiated by a nucleic acid primer (Pitulle et al., "Initiator Oligonucleotides for the Combination of Chemical and Enzymatic RNA Synthesis," *Gene* 112, 101–105 (1992)) which carries, as one embodiment of this invention, appropriate linking functionalities, L, which allow the immobilization of the nested RNA fragments, as outlined above, prior to mass spectrometric analysis for purification and/or appropriate modification and/or conditioning.

For this immobilization process of the DNA/RNA sequencing products for mass spectrometric analysis, various solid supports can be used, e.g., beads (silica gel, controlled pore glass, magnetic beads, Sephadex/Sepharose beads, cellulose beads, etc.), capillaries, glass fiber filters, glass surfaces, metal surfaces or plastic material. Examples of useful plastic materials include membranes in filter or microtiter plate formats, the latter allowing the automation of the purification process by employing microtiter plates which, as one embodiment of the invention, carry a permeable membrane in the bottom of the well functionalized with L'. Membranes can be based on polyethylene, polypropylene, polyamide, polyvinylidenedifluoride and the like. Examples of suitable metal surfaces include steel, gold, silver, aluminum, and copper. After purification, cation exchange, and/or modification of the phosphodiester backbone of the L-L' bound nested Sanger fragments, they can be cleaved off the solid support chemically, enzymatically or physically. Also, the L-L' bound fragments can be cleaved from the support when they are subjected to mass spectrometric analysis by using appropriately chosen L-L' linkages and corresponding laser energies/intensities as described above and in FIGS. 19–23.

The highly purified, four base-specifically terminated DNA or RNA fragment families are then analyzed with regard to their fragment lengths via determination of their respective molecular weights by MALDI or ES mass spectrometry.

For ES, the samples, dissolved in water or in a volatile buffer, are injected either continuously or discontinuously into an atmospheric pressure ionization interface (API) and then mass analyzed by a quadrupole. With the aid of a computer program, the molecular weight peaks are searched for the known molecular weight of the nucleic acid primer (UP) and determined which of the four chain-terminating nucleotides has been added to the UP. This represents the first nucleotide of the unknown sequence. Then, the second, the third, the $n^{th}$ extension product can be identified in a similar manner and, by this, the nucleotide sequence is assigned. The generation of multiple ion peaks which can be obtained using ES mass spectrometry can increase the accuracy of the mass determination.

In MALDI mass spectrometry, various mass analyzers can be used, e.g., magnetic sector/magnetic deflection instruments in single or triple quadrupole mode (MS/MS), Fourier transform and time-of-flight (TOF) configurations as is known in the art of mass spectrometry. FIGS. 2A through 6 are given as an example of the data obtainable when sequencing a hypothetical DNA fragment of 50 nucleotides in length (SEQ ID NO:3) and having a molecular weight of 15,344.02 daltons. The molecular weights calculated for the ddT (FIGS. 2A and 2B), ddA (FIGS. 3A and 3B), ddG (FIGS. 4A and 4B) and ddC (FIGS. 5A and 5B) terminated products are given (corresponding to fragments of SEQ ID NO:3) and the idealized four MALDI-TOF mass spectra shown. All four spectra are superimposed, and from this, the DNA sequence can be generated. This is shown in the summarizing FIG. 6, demonstrating how the molecular weights are correlated with the DNA sequence. MALDI-TOF spectra have been generated for the ddT terminated products (FIG. 16) corresponding to those shown in FIG. 2 and these spectra have been superimposed (FIG. 17). The correlation of calculated molecular weights of the ddT fragments and their experimentally-verified weights are shown in Table 1. Likewise, if all four chain-terminating reactions are combined and then analyzed by mass spectrometry, the molecular weight difference between two adjacent peaks can be used to determine the sequence. For the desorption/ionization process, numerous matrix/laser combinations can be used.

TABLE I

Correlation of calculated and experimentally verified molecular weights of the 13 DNA fragments of FIGS. 2 and 16.

| Fragment (n-mer) | calculated mass | experimental mass | difference |
|---|---|---|---|
| 7-mer | 2104.45 | 2119.9 | +15.4 |
| 10-mer | 3011.04 | 3026.1 | +15.1 |
| 11-mer | 3315.24 | 3330.1 | +14.9 |
| 19-mer | 5771.82 | 5788.0 | +16.2 |
| 20-mer | 6076.02 | 6093.8 | +17.8 |
| 24-mer | 7311.82 | 7374.9 | +63.1 |
| 26-mer | 7945.22 | 7960.9 | +15.7 |
| 33-mer | 10112.63 | 10125.3 | +12.7 |
| 37-mer | 11348.43 | 11361.4 | +13.0 |
| 38-mer | 11652.62 | 11670.2 | +17.6 |
| 42-mer | 12872.42 | 12888.3 | +15.9 |
| 46-mer | 14108.22 | 14125.0 | +16.8 |
| 50-mer | 15344.02 | 15362.6 | +18.6 |

In order to increase throughput to a level necessary for high volume genomic and cDNA sequencing projects, a further embodiment of the present invention is to utilize multiplex mass spectrometry to simultaneously determine more than one sequence. This can be achieved by several, albeit different, methodologies, the basic principle being the mass modification of the nucleic acid primer (UP), the chain-elongating and/or terminating nucleoside triphosphates, or by using mass-differentiated tag probes hybridizable to specific tag sequences. The term "nucleic acid primer" as used herein encompasses primers for both DNA and RNA Sanger sequencing.

By way of example, FIG. 7 presents a general formula of the nucleic acid primer (UP) and the tag probes (1P). The mass modifying moiety can be attached, for instance, to either the 5'-end of the oligonucleotide ($M^1$), to the nucleobase (or bases) ($M^2$, $M^7$), to the phosphate backbone ($M^3$), and to the 2'-position of the nucleoside (nucleosides) ($M^4$, $M^6$) or/and to the terminal 3'-position ($M^5$). Primer length can vary between 1 and 50 nucleotides in length. For the priming of DNA Sanger sequencing, the primer is preferentially in the range of about 15 to 30 nucleotides in length. For artificially priming the transcription in a RNA polymerase-mediated Sanger sequencing reaction, the length of the primer is preferentially in the range of about 2 to 6 nucleotides. If a tag probe (TP) is to hybridize to the integrated tag sequence of a family chain-terminated fragments, its preferential length is about 20 nucleotides.

The table in FIG. 7 depicts some examples of mass-modified primer/tag probe configurations for DNA, as well as RNA, Sanger sequencing. This list is, however, not meant to be limiting, since numerous other combinations of mass-modifying functions and positions within the oligonucleotide molecule are possible and are deemed part of the invention. The mass-modifying functionality can be, for example, a halogen, an azido, or of the type, XR, wherein X is a linking group and R is a mass-modifying functionality. The mass-modifying functionality can thus be used to introduce defined mass increments into the oligonucleotide molecule.

In another embodiment, the nucleotides used for chain-elongation and/or termination are mass-modified. Examples of such modified nucleotides are shown in FIG. 8. Here the mass-modifying moiety, M, can be attached either to the nucleobase, $M^2$ (in case of the $c^7$-deazanucleosides also to C-7, $M^7$), to the triphosphate group at the alpha phosphate, $M^3$, or to the 2'-position of the sugar ring of the nucleoside triphosphate, $M^4$ and $M^6$. Furthermore, the mass-modifying functionality can be added so as to affect chain termination, such as by attaching it to the 3'-position of the sugar ring in the nucleoside triphosphate, $M^5$. The list in FIG. 8 represents examples of possible configurations for generating chain-terminating nucleoside triphosphates for RNA or DNA Sanger sequencing. For those skilled in the art, however, it is clear that many other combinations can serve the purpose of the invention equally well. In the same way, those skilled in the art will recognize that chain-elongating nucleoside triphosphates can also be mass-modified in a similar fashion with numerous variations and combinations in functionality and attachment positions.

Figure 9:
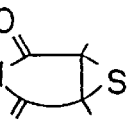
FIG. 9 outlines various linking chemistries (X) with either polyethylene glycol or terminally monoalkylated polyethylene glycol (R) as an example.

Without limiting the scope of the invention, FIG. 9 gives a more detailed description of particular examples of how the mass-modification, M, can be introduced for X in XR as well as using oligo-/polyethylene glycol derivatives for R. The mass-modifying increment in this case is 44, i.e. five different mass-modified species can be generated by just changing m from 0 to 4 thus adding mass units of 45 (m=0), 89 (m=1), 133 (m=2), 177 (m=3) and 221 (m=4) to the nucleic acid primer (UP), the tag probe (TP) or the nucleoside triphosphates respectively. The oligo/polyethylene glycols can also be monoalkylated by a lower alkyl such as methyl, ethyl, propyl, isopropyl, t-butyl and the like. A selection of linking functionalities, X, are also illustrated. Other chemistries can be used in the mass-modified compounds, as for example, those described recently in *Oligonucleotides and Analogues, A Practical Approach*, F. Eckstein, editor, IRL Press, Oxford, 1991.

In yet another embodiment, various mass-modifying functionalities, R, other than oligo/polyethylene glycols, can be selected and attached via appropriate linking chemistries, X. Without any limitation, some examples are given in FIG. 10. A simple mass-modification can be achieved by substituting H for halogens like F, Cl, Br and/or I, or pseudohalogens such as SCN, NCS, or by using different alkyl, aryl or aralkyl moieties such as methyl, ethyl, propyl, isopropyl, t-butyl, hexyl, phenyl, substituted phenyl, benzyl, or functional groups such as $CH_2F$, $CHF_2$, $CF_3$, $Si(CH_3)_3$, $Si(CH_3)_2(C_2H_5)$, $Si(CH_3)(C_2H_5)_2$, $Si(C_2H_5)_3$. Yet another mass-modification can be obtained by attaching homo- or heteropeptides through X to the UP, TP or nucleoside triphosphates. One example useful in generating mass-modified species with a mass increment of 57 is the attachment of oligoglycines, e.g., mass-modifications of 74 (r=1, m=0), 131 (r=1, m=2), 188 (r=1, m=3), 245 (r=1, m=4) are achieved. Simple oligoamides also can be used, e.g., mass-modifications of 74 (r=1, m=0), 88 (r=2, m=0), 102 (r=3, m=0), 116 (r=4, m=0), etc. are obtainable. For those skilled in the art, it will be obvious that there are numerous possibilities in addition to those given in FIG. 10 and the above mentioned reference (*Oligonucleotides and Analogues*, F. Eckstein, 1991), for introducing, in a predetermined manner, many different mass-modifying functionalities to UP, TP and nucleoside triphosphates which are acceptable for DNA and RNA Sanger sequencing.

As used herein, the superscript 0–i designates i+1 mass differentiated nucleotides, primers or tags. In some instances, the superscript 0 (e.g., $NTP^0$, $UP^0$) can designate an unmodified species of a particular reactant, and the superscript i (e.g., $NTP^i$, $NTP^1$, $NTP^2$, etc.) can designate the i-th mass-modified species of that reactant. If, for example, more than one species of nucleic acids (e.g., DNA clones) are to be concurrently sequenced by multiplex DNA sequencing, then i+1 different mass-modified nucleic acid primers ($UP^0, UP^1, \ldots UP^i$) can be used to distinguish each set of base-specifically terminated fragments, wherein each species of mass-modified $UP^i$ can be distinguished by mass spectrometry from the rest.

Figure 13:
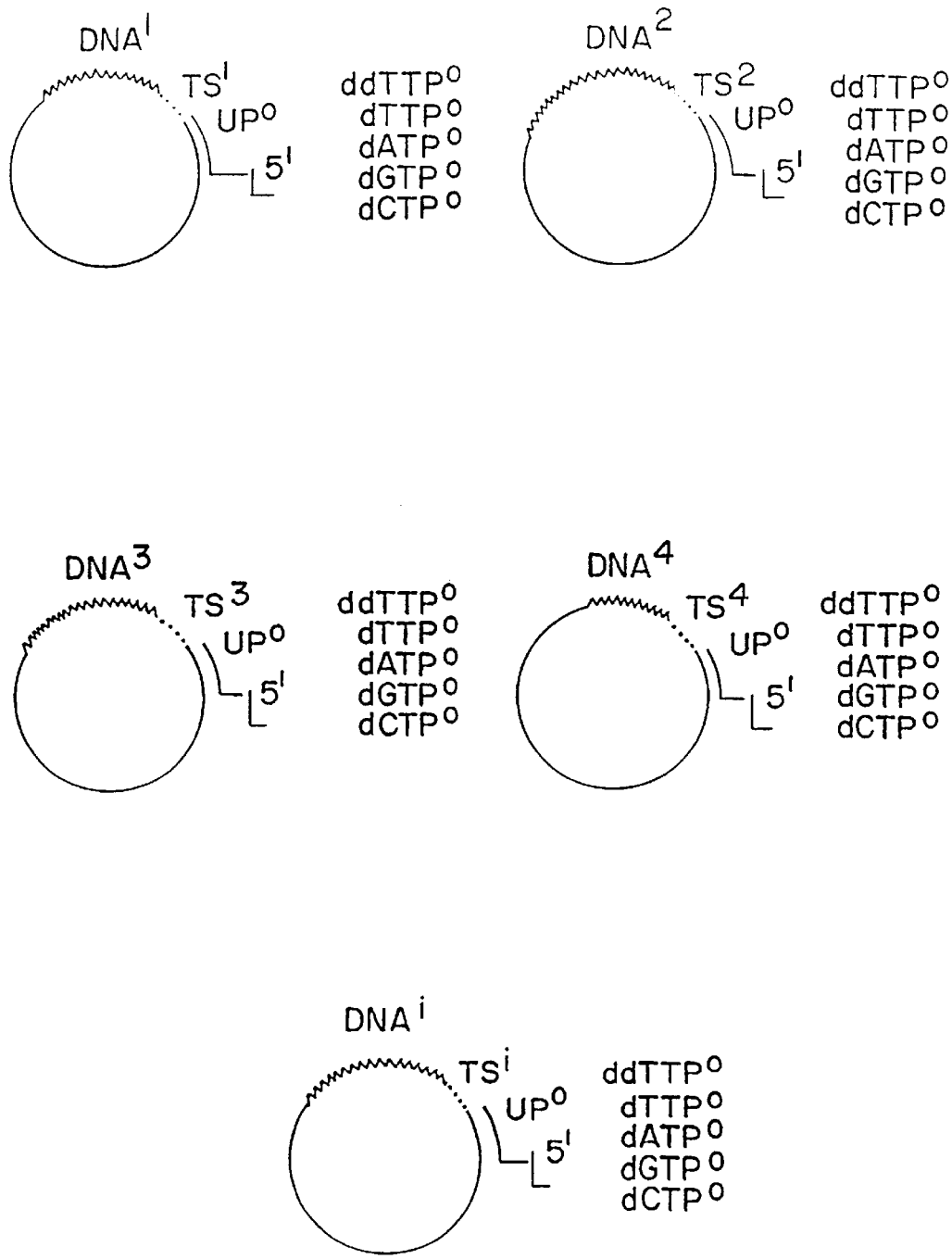
FIG. 13 shows multiplex mass spectrometric sequencing by involving the hybridization of mass-modified tag sequence specific probes.

As illustrative embodiments of this invention, three different basic processes for multiplex mass spectrometric DNA sequencing employing the described mass-modified reagents are described below:

A) Multiplexing by the use of mass-modified nucleic acid primers (UP) for Sanger DNA or RNA sequencing (see for example FIG. 11);

B) Multiplexing by the use of mass-modified nucleoside triphosphates as chain elongators and/or chain terminators for Sanger DNA or RNA sequencing (see for example FIG. 12); and C) Multiplexing by the use of tag probes which specifically hybridize to tag sequences which are integrated into part of the four Sanger DNA/RNA base-specifically terminated fragment families. Mass modification here can be achieved as described for FIGS. 7, 9 and 10, or alternately, by designing different oligonucleotide sequences having the same or different length with unmodified nucleotides which, in a predetermined way, generate appropriately differentiated molecular weights (see for example FIG. 13).

The process of multiplexing by mass-modified nucleic acid primers (UP) is illustrated by way of example in FIG. 11 for mass analyzing four different DNA clones simultaneously. The first reaction mixture is obtained by standard Sanger DNA sequencing having unknown DNA fragment 1 (clone 1) integrated in an appropriate vector (e.g., M13mp18), employing an unmodified nucleic acid primer $UP^0$, and a standard mixture of the four unmodified deoxynucleoside triphosphates, $dNTP^0$, and with ⅒th of one of the four dideoxynucleoside triphosphates, $ddNTP^0$. A second reaction mixture for DNA fragment 2 (clone 2) is obtained by employing a mass-modified nucleic acid primer $Up^1$ and, as before, the four unmodified nucleoside triphosphates, $dNTP^0$, containing in each separate Sanger reaction ⅒th of the chain-terminating unmodified dideoxynucleoside triphosphates $ddNTP^0$. In the other two experiments, the four Sanger reactions have the following compositions: DNA fragment 3 (clone 3), $UP^2$, $dNTP^0$, $ddNTP^0$ and DNA fragment 4 (clone 4), $UP^3$, $dNTP^0$, $ddNTP^0$. For mass spectrometric DNA sequencing, all base-specifically terminated reactions of the four clones are pooled and mass analyzed. The various mass peaks belonging to the four dideoxy-terminated (e.g., ddT-terminated) fragment families are assigned to specifically elongated and ddT-terminated fragments by searching (such as by a computer program) for the known molecular ion peaks of $UP^0$, $UP^1$, $UP^2$ and $UP^3$ extended by either one of the four dideoxynucleoside triphosphates, $UP^0$-$ddN^0$, $UP^1$-$ddN^0$, $UP^2$-$ddN^0$ and $UP^3$-$ddN^0$. In this way, the first nucleotides of the four unknown DNA sequences of clone 1 to 4 are determined. The process is repeated, having memorized the molecular masses of the four specific first extension products, until the four sequences are assigned. Unambiguous mass/sequence assignments are possible even in the worst case scenario in which the four mass-modified nucleic acid primers are extended by the same dideoxynucleoside triphosphate, the extension products then being, for example, $UP^0$-ddT, $UP^1$-ddT, $UP^2$-ddT and $UP^3$-ddT, which differ by the known mass increment differentiating the four nucleic acid primers. In another embodiment of this invention, an analogous technique is employed using different vectors containing, for example, the SP6 and/or T7 promoter sequences, and performing transcription with the nucleic acid primers $UP^0$, $UP^1$, $Up^2$ and $UP^3$ and either an RNA polymerase (e.g., SP6 or T7 RNA polymerase) with chain-elongating and terminating unmodified nucleoside triphosphates $NTP^0$ and 3'-$dNTP^0$. Here, the DNA sequence is being determined by Sanger RNA sequencing.

FIG. 12 illustrates the process of multiplexing by mass-modified chain-elongating or/and terminating nucleoside triphosphates in which three different DNA fragments (3 clones) are mass analyzed simultaneously. The first DNA Sanger sequencing reaction (DNA fragment 1, clone 1) is the standard mixture employing unmodified nucleic acid primer $UP^0$, $dNTP^0$ and in each of the four reactions one of the four $ddNTP^0$. The second (DNA fragment 2, clone 2) and the third (DNA fragment 3, clone 3) have the following contents: $UP^0$, $dNTP^0$, $ddNTP^1$ and $UP^0$, $dNTP^0$, $ddNTP^2$, respectively. In a variation of this process, an amplification of the mass increment in mass-modifying the extended DNA fragments can be achieved by either using an equally mass-modified deoxynucleoside triphosphate (i.e., $dNTP^1$, $dNTP^2$) for chain elongation alone or in conjunction with the homologous equally mass-modified dideoxynucleoside triphosphate. For the three clones depicted above, the contents of the reaction mixtures can be as follows: either $UP^0/dNTP^0/ddNTP^0$, $UP^0/dNTP^1/ddNTP^0$ and $UP^0/dNTP^2/ddNTP^0$ or $UP^0/dNT^0/ddNTP^0$, $UP^0/dNTP^1/ddNT^1$ and $UP^0/dNTP^2/ddNTP^2$. As described above, DNA sequencing can be performed by Sanger RNA sequencing employing unmodified nucleic acid primers, $UP^0$, and an appropriate mixture of chain-elongating and terminating nucleoside triphosphates. The mass-modification can be again either in the chain-terminating nucleoside triphosphate alone or in conjunction with mass-modified chain-elongating nucleoside triphosphates. Multiplexing is achieved by pooling the three base-specifically terminated sequencing reactions (e.g., the ddTTP terminated products) and simultaneously analyzing the pooled products by mass spectrometry. Again, the first extension products of the known nucleic acid primer sequence are assigned, e.g., via a computer program. Mass/sequence assignments are possible even in the worst case in which the nucleic acid primer is extended/terminated by the same nucleotide, e.g., ddT, in all three clones. The following configurations thus obtained can be well differentiated by their different mass-modifications: $UP^0$-$ddT^0$, $UP^0$-$ddT^1$, $UP^0$-$ddT^2$.

In yet another embodiment of this invention, DNA sequencing by multiplex mass spectrometry can be achieved by cloning the DNA fragments to be sequenced in "plex-vectors" containing vector specific "tag sequences" as described (Köster et al, "Oligonucleotide Synthesis and Multiplex DNA Sequencing Using Chemiluminescent Detection," *Nucleic Acids Res.* Symposium Ser. No. 24, 318–321 (1991)); then pooling clones from different plex-vectors for DNA preparation and the four separate Sanger sequencing reactions using standard $dNTP^0/ddNTP^0$ and nucleic acid primer $UP^0$; purifying the four multiplex fragment families via linking to a solid support through the linking group, L, at the 5'-end of UP; washing out all by-products, and cleaving the purified multiplex DNA fragments off the support or using the L-L' bound nested Sanger fragments as such for mass spectrometric analysis as described above; performing demultiplexing by one-by-one hybridization of specific "tag probes"; and subsequently analyzing by mass spectrometry (see, for example, FIG. 13). As a reference point, the four base-specifically terminated multiplex DNA fragment families are run by the mass spectrometer and all ddT$^O$-, ddA$^O$-, ddC$^O$- and ddG$^O$-terminated molecular ion peaks are respectively detected and memorized. Assignment of, for example, ddT$^O$-terminated DNA fragments to a specific fragment family is accomplished by another mass spectrometric analysis after hybridization of the specific tag probe (TP) to the corresponding tag sequence contained in the sequence of this specific fragment family. Only those molecular ion peaks which are capable of hybridizing to the specific tag probe are shifted to a higher molecular mass by the same known mass increment (e.g. of the tag probe). These shifted ion peaks, by virtue of all hybridizing to a specific tag probe, belong to the same fragment family. For a given fragment family, this is repeated for the remaining chain terminated fragment families with the same tag probe to assign the complete DNA sequence. This process is repeated i-1 times corresponding to i clones multiplexed (the i-th clone is identified by default).

The differentiation of the tag probes for the different multiplexed clones can be obtained just by the DNA sequence and its ability to Watson-Crick base pair to the tag sequence. It is well known in the art how to calculate stringency conditions to provide for specific hybridization of a given tag probe with a given tag sequence (see, for example, *Molecular Cloning: A laboratory manual* 2ed, ed. by Sambrook, Fritsch and Maniatis (Cold Spring Harbor Laboratory Press: NY, 1989, Chapter 11). Furthermore, differentiation can be obtained by designing the tag sequence for each plex-vector to have a sufficient mass difference so as to be unique just by changing the length or base composition or by mass-modifications according to FIGS. 7, 9 and 10. In order to keep the duplex between the tag sequence and the tag probe intact during mass spectrometric analysis, it is another embodiment of the invention to provide for a covalent attachment mediated by, for example, photoreactive groups such as psoralen and ellipticine and by other methods known to those skilled in the art (see, for example, Hélène et al., *Nature* 344, 358 (1990) and Thuong et al. "Oligonucleotides Attached to Intercalators, Photoreactive and Cleavage Agents" in F. Eckstein, *Oligonucleotides and Analogues: A Practical Approach,* IRL Press, Oxford 1991, 283–306).

The DNA sequence is unraveled again by searching for the lowest molecular weight molecular ion peak corresponding to the known UP$^O$-tag sequence/tag probe molecular weight plus the first extension product, e.g., ddT$^O$, then the second, the third, etc.

In a combination of the latter approach with the previously described multiplexing processes, a finer increase in multiplexing can be achieved by using, in addition to the tag probe/tag sequence interaction, mass-modified nucleic acid primers (FIG. 7) and/or mass-modified deoxynucleoside, dNTP$^{O-i}$, and/or dideoxynucleoside triphosphates, ddNTP$^{O-i}$. Those skilled in the art will realize that the tag sequence/tag probe multiplexing approach is not limited to Sanger DNA sequencing generating nested DNA fragments with DNA polymerases. The DNA sequence can also be determined by transcribing the unknown DNA sequence from appropriate promoter-containing vectors (see above) with various RNA polymerases and mixtures of NTP$^{O-i}$/3'-dNTP$^{O-i}$, thus generating nested RNA fragments.

In yet another embodiment of this invention, the mass-modifying functionality can be introduced by a two or multiple step process. In this case, the nucleic acid primer, the chain-elongating or terminating nucleoside triphosphates and/or the tag probes are, in a first step, modified by a precursor functionality such as azido, —N$_3$, or modified with a functional group in which the R in XR is H (FIGS. 7, 9) thus providing temporary functions, e.g., but not limited to —OH, —NH$_2$, —NHR, —SH, —NCS, —OCO (CH$_2$)$_r$COOH (r=1–20), —NHCO(CH$_2$)$_r$COOH (r=1–20), —OSO$_2$OH, —OCO(CH$_2$)$_r$I (r=1–20), —OP(O-Alkyl)N (Alkyl)$_2$. These less bulky functionalities result in better substrate properties for the enzymatic DNA or RNA synthesis reactions of the DNA sequencing process. The appropriate mass-modifying functionality is then introduced after the generation of the nested base-specifically terminated DNA or RNA fragments prior to mass spectrometry. Several examples of compounds which can serve as mass-modifying functionalities are depicted in FIGS. 9 and 10 without limiting the scope of this invention.

Another aspect of this invention concerns kits for sequencing nucleic acids by mass spectrometry which include combinations of the above-described sequencing reactants. For instance, in one embodiment, the kit comprises reactants for multiplex mass spectrometric sequencing of several different species of nucleic acid. The kit can include a solid support having a linking functionality (L$^1$) for immobilization of the base-specifically terminated products; at least one nucleic acid primer having a linking group (L) for reversibly and temporarily linking the primer and solid support through, for example, a photocleavable bond; a set of chain-elongating nucleotides (e.g., dATP, dCTP, dGTP and dTTP, or ATP, CTP, GTP and UTP); a set of chain-terminating nucleotides (such as 2',3'-dideoxynucleotides for DNA synthesis or 3'-deoxynucleotides for RNA synthesis); and an appropriate polymerase for synthesizing complementary nucleotides. Primers and/or terminating nucleotides can be mass-modified so that the base-specifically terminated fragments generated from one of the species of nucleic acids to be sequenced can be distinguished by mass spectrometry from all of the others. Alternative to the use of mass-modified synthesis reactants, a set of tag probes (as described above) can be included in the kit. The kit can also include appropriate buffers as well as instructions for performing multiplex mass spectrometry to concurrently sequence multiple species of nucleic acids.

In another embodiment, a nucleic acid sequencing kit can comprise a solid support as described above, a primer for initiating synthesis of complementary nucleic acid fragments, a set of chain-elongating nucleotides and an appropriate polymerase. The mass-modified chain-terminating nucleotides are selected so that the addition of one of the chain terminators to a growing complementary nucleic acid can be distinguished by mass spectrometry.

EXAMPLE 1

Immobilization of primer-extension products of Sanger DNA sequencing reaction for mass spectrometric analysis via disulfide bonds As a solid support, Sequelon membranes (Millipore Corp., Bedford, Mass.) with phenyl isothiocyanate groups are used as a starting material. The membrane disks, with a diameter of 8 mm, are wetted with a solution of N-methylmorpholine/water/2-propanol (NMM solution) (2/49/49 v/v/v), the excess liquid removed with filter paper and placed on a piece of plastic film or aluminum foil located on a heating block set to 55° C. A solution of 1 mM 2-mercaptoethylamine (cysteamine) or 2,2'-dithio-bis (ethylamine) (cystamine) or S-(2-thiopyridyl)2-thio-ethylamine (10 ul, 10 nmol) in NMM is added per disk and heated at 55° C. After 15 min, 10 ul of NMM solution are added per disk and heated for another 5 min. Excess of isothiocyanate groups may be removed by treatment with 10 ul of a 10 mM solution of glycine in NMM solution. For cystamine, the disks are treated with 10 ul of a solution of 1M aqueous dithiothreitol (DTT)/2-propanol (1:1 v/v) for 15 min at room temperature. Then, the disks are thoroughly washed in a filtration manifold with 5 aliquots of 1 ml each of the NMM solution, then with 5 aliquots of 1 ml acetonitrile/water (1/1 v/v) and subsequently dried. If not used immediately the disks are stored with free thiol groups in a solution of 1M aqueous dithiothreitol/2-propanol (1:1 v/v) and, before use, DTT is removed by three washings with 1 ml each of the NMM solution. The primer oligonucleotides with 5'-SH functionality can be prepared by various methods (e.g., B. C. F Chu et al., *Nucleic Acids Res.* 14, 5591–5603 (1986), Sproat et al., *Nucleic Acids Res.* 15, 4837–48 (1987) and *Oligonucleotides and Analogues: A Practical Approach* (F. Eckstein, editor), IRL Press Oxford, 1991). Sequencing reactions according to the Sanger protocol are performed in a standard way (e.g., H. Swerdlow et al., *Nucleic Acids Res.* 18, 1415–19 (1990)). In the presence of about 7–10 mM DTT the free 5'-thiol primer can be used; in other cases, the SH functionality can be protected, e.g., by a trityl group during the Sanger sequencing reactions and removed prior to anchoring to the support in the following way. The four sequencing reactions (150 ul each in an Eppendorf tube) are terminated by a 10 min incubation at 70° C. to denature the DNA polymerase (such as Klenow fragment, Sequenase) and the reaction mixtures are ethanol precipitated. The supernatants are removed and the pellets vortexed with 25 ul of an 1M aqueous silver nitrate solution, and after one hour at room temperature, 50 ul of an 1 M aqueous solution of DTT is added and mixed by vortexing. After 15 min, the mixtures are centrifuged and the pellets are washed twice with 100 ul ethylacetate by vortexing and centrifugation to remove excess DTT. The primer extension products with free 5'-thiol group are now coupled to the thiolated membrane supports under mild oxidizing conditions. In general, it is sufficient to add the 5'-thiolated primer extension products dissolved in 10 ul 10 mM de-aerated triethylammonium acetate buffer (TEAA) pH 7.2 to the thiolated membrane supports. Coupling is achieved by drying the samples onto the membrane disks with a cold fan. This process can be repeated by wetting the membrane with 10 ul of 10 mM TEAA buffer pH 7.2 and drying as before. When using the 2-thiopyridyl derivatized compounds, anchoring can be monitored by the release of pyridine-2-thione spectrophotometrically at 343 nm.

In another variation of this approach, the oligonucleotide primer is functionalized with an amino group at the 5'-end which is introduced by standard procedures during automated DNA synthesis. After primer extension, during the Sanger sequencing process, the primary amino group is reacted with 3-(2-pyridyldithio) propionic acid N-hydroxysuccinimide ester (SPDP) and subsequently coupled to the thiolated supports and monitored by the release of pyridyl-2-thione as described above. After denaturation of DNA polymerase and ethanol precipitation of the sequencing products, the supernatants are removed and the pellets dissolved in 10 ul 10 mM TEAA buffer pH 7.2 and 10 ul of a 2 mM solution of SPDP in 10 mM TEAA are added. The reaction mixture is vortexed and incubated for 30 min at 25° C. Excess SPDP is then removed by three extractions (vortexing, centrifugation) with 50 ul each of ethanol and the resulting pellets are dissolved in 10 ul 10 mM TEAA buffer pH 7.2 and coupled to the thiolated supports (see above).

The primer-extension products are purified by washing the membrane disks three times each with 100 ul NMM solution and three times with 100 ul each of 10 mM TEAA buffer pH 7.2. The purified primer-extension products are released by three successive treatments with 10 ul of 10 mM 2-mercaptoethanol in 10 mM TEAA buffer pH 7.2, lyophilized and analyzed by either ES or MALDI mass spectrometry.

This procedure can also be used for the mass-modified nucleic acid primers $UP^{0-i}$ in an analogous and appropriate way, taking into account the chemical properties of the mass-modifying functionalities.

EXAMPLE 2

Immobilization of primer-extension products of Sanger DNA sequencing reaction for mass spectrometric analysis via the levulinyl group 5-Aminolevulinic acid is protected at the primary amino group with the Fmoc group using 9-fluorenylmethyl N-succinimidyl carbonate and is then transformed into the N-hydroxysuccinimide ester (NHS ester) using N-hydroxysuccinimide and dicyclohexyl carbodiimide under standard conditions. For the Sanger sequencing reactions, nucleic acid primers, $UP^{0-i}$, are used which are functionalized with a primary amino group at the 5'-end introduced by standard procedures during automated DNA synthesis with aminolinker phosphoamidites as the final synthetic step. Sanger sequencing is performed under standard conditions (see above). The four reaction mixtures (150 ul each in an Eppendorf tube) are heated to 70° C. for 10 min to inactivate the DNA polymerase, ethanol precipitated, centrifuged and resuspended in 10 ul of 10 mM TEAA buffer pH 7.2. 10 ul of a 2 mM solution of the Fmoc-5-aminolevulinyl-NHS ester in 10 mM TEAA buffer is added, vortexed and incubated at 25° C. for 30 min. The excess of the reagent is removed by ethanol precipitation and centrifugation. The Fmoc group is cleaved off by resuspending the pellets in 10 ul of a solution of 20% piperidine in N,N-dimethylformamide/water (1:1 v/v). After 15 min at 25° C., piperidine is thoroughly removed by three precipitations/centrifugations with 100 ul each of ethanol, the pellets are resuspended in 10 ul of a solution of N-methylmorpholine, 2-propanol and water (2/10/88 v/v/v) and are coupled to the solid support carrying an isothiocyanate group. In the case of the DITC-Sequelon membrane (Millipore Corp., Bedford, Mass.), the membranes are prepared as described in EXAMPLE 1 and coupling is achieved on a heating block at 55° C. as described above. RNA extension products are immobilized in an analogous way. The procedure can be applied to other solid supports with isothiocyanate groups in a similar manner.

The immobilized primer-extension products are extensively washed three times with 100 ul each of NMM solution and three times with 100 ul 10 mM TEAA buffer pH 7.2. The purified primer-extension products are released by three successive treatments with 10 ul of 100 mM hydrazinium acetate buffer pH 6.5, lyophilized and analyzed by either ES or MALDI mass spectrometry.

EXAMPLE 3

Immobilization of primer-extension products of Sanger DNA sequencing reaction for mass spectrometric analysis via a trypsin sensitive linkage Sequelon DITC membrane disks of 8 mm diameter (Millipore Corp., Bedford, Mass.) are wetted with 10 ul of NMM solution (N-methylmorpholine/propanaol-2/water; 2/49/49 v/v/v) and a linker arm introduced by reaction with 10 ul of a 10 mM solution of 1,6-diaminohexane in NMM. The excess diamine is removed by three washing steps with 100 ul of NMM solution. Using standard peptide synthesis protocols, two L-lysine residues are attached by two successive condensations with N-Fmoc-N-tBoc-L-lysine pentafluorophenylester, the terminal Fmoc group is removed with piperidine in NMM and the free α-amino group coupled to 1,4-phenylene diisothiocyanate (DITC). Excess DITC is removed by three washing steps with 100 ul 2-propanol and the N-tBoc groups removed with trifluoroacetic acid according to standard peptide synthesis procedures. The nucleic acid primer-extension products are prepared from oligonucleotides which carry a primary amino group at the 5'-terminus. The four Sanger DNA sequencing reaction mixtures (150 ul each in Eppendorf tubes) are heated for 10 min at 70° C. to inactivate the DNA polymerase, ethanol precipitated, and the pellets resuspended in 10 ul of a solution of N-methylmorpholine, 2-propanol and water (2/10/88 v/v/v). This solution is transferred to the Lys-Lys-DITC membrane disks and coupled on a heating block set at 55° C. After drying, 10 ul of NMM solution is added and the drying process repeated.

The immobilized primer-extension products are extensively washed three times with 100 ul each of NMM solution and three times with 100 ul each of 10 mM TEAA buffer pH 7.2. For mass spectrometric analysis, the bond between the primer-extension products and the solid support is cleaved by treatment with trypsin under standard conditions and the released products analyzed by either ES or MALDI mass spectrometry with trypsin serving as an internal mass standard.

EXAMPLE 4
Immobilization of primer-extension products of Sanger DNA sequencing reaction for mass spectrometric analysis via pyrophosphate linkage The DITC Sequelon membrane (disks of 8 mm diameter) are prepared as described in EXAMPLE 3 and 10 ul of a 10 mM solution of 3-aminopyridine adenine dinucleotide (APAD) (Sigma) in NMM solution added. The excess APAD is removed by a 10 ul wash of NMM solution and the disks are treated with 10 ul of 10 mM sodium periodate in NMM solution (15 min, 25° C.). Excess periodate is removed and the primer-extension products of the four Sanger DNA sequencing reactions (150 ul each in Eppendorf tubes) employing nucleic acid primers with a primary amino group at the 5'-end are ethanol precipitated, dissolved in 10 ul of a solution of N-methylmorpholine/2-propanol/water (2/10/88 v/v/v) and coupled to the 2'3'-dialdehydo groups of the immobilized NAD analog.

The primer-extension products are extensively washed with the NMM solution (3 times with 100 ul each) and 10 mM TEAA buffer pH 7.2 (3 times with 100 ul each) and the purified primer-extension products are released by treatment with either NADase or pyrophosphatase in 10 mM TEAA buffer at pH 7.2 at 37° C. for 15 min, lyophilized and analyzed by either ES or MALDI mass spectrometry, the enzymes serving as internal mass standards.

EXAMPLE 5
Synthesis of nucleic acid primers mass-modified by glycine residues at the 5'-position of the sugar moiety of the terminal nucleoside Oligonucleotides are synthesized by standard automated DNA synthesis using β-cyanoethylphosphoamidites (H. Köster et al., *Nucleic Acids Res.* 12, 4539 (1984)) and a 5'-amino group is introduced at the end of solid phase DNA synthesis (e.g. Agrawal et al., *Nucleic Acids Res.* 14, 6227–45 (1986) or Sproat et al., *Nucleic Acids Res.* 15, 6181–96 (1987)). The total amount of an oligonucleotide synthesis, starting with 0.25 umol CPG-bound nucleoside, is deprotected with concentrated aqueous ammonia, purified via OligoPAK™ Cartridges (Millipore Corp., Bedford, Mass.) and lyophilized. This material with a 5'-terminal amino group is dissolved in 100 ul absolute N,N-dimethylformamide (DMF) and condensed with 10 μmole N-Fmoc-glycine pentafluorophenyl ester for 60 min at 25° C. After ethanol precipitation and centrifugation, the Fmoc group is cleaved off by a 10 min treatment with 100 ul of a solution of 20% piperidine in N,N-dimethylformamide. Excess piperidine, DMF and the cleavage product from the Fmoc group are removed by ethanol precipitation and the precipitate lyophilized from 10 mM TEAA buffer pH 7.2. This material is now either used as primer for the Sanger DNA sequencing reactions or one or more glycine residues (or other suitable protected amino acid active esters) are added to create a series of mass-modified primer oligonucleotides suitable for Sanger DNA or RNA sequencing. Immobilization of these mass-modified nucleic acid primers $UP^{1-i}$ after primer-extension during the sequencing process can be achieved as described, e.g., in EXAMPLES 1 to 4.

EXAMPLE 6
Synthesis of nucleic acid primers mass-modified at C-5 of the heterocyclic base of a pyrimidine nucleoside with glycine residues Starting material was 5-(3-aminopropynyl-1)-3' 5'-di-p-tolyldeoxyuridine prepared and 3' 5'-de-O-acylated according to literature procedures (Haralambidis et al., *Nucleic Acids Res.* 15, 4857–76 (1987)). 0.281 g (1.0 mmole) 5-(3-aminopropynyl-1)-2'-deoxyuridine were reacted with 0.927 g (2.0 mmole) N-Fmoc-glycine pentafluorophenylester in 5 ml absolute N,N-dimethylformamide in the presence of 0.129 g (1 mmole; 174 ul) N,N-diisopropylethylamine for 60 min at room temperature. Solvents were removed by rotary evaporation and the product was purified by silica gel chromatography (Kieselgel 60, Merck; column: 2.5×50 cm, elution with chloroform/methanol mixtures). Yield was 0.44 g (0.78 mmole, 78%). In order to add another glycine residue, the Fmoc group is removed with a 20 min treatment with 20% solution of piperidine in DMF, evaporated in vacuo and the remaining solid material extracted three times with 20 ml ethylacetate. After having removed the remaining ethylacetate, N-Fmoc-glycine pentafluorophenylester is coupled as described above. 5-(3-(N-Fmoc-glycyl)-amidopropynyl-1)-2'-deoxyuridine is transformed into the 5'-O-dimethoxytritylated nucleoside-3'-O-β-cyanoethyl-N,N-diisopropylphosphoamidite and incorporated into automated oligonucleotide synthesis by standard procedures (H. Köster et al., *Nucleic Acids Res.* 12, 2261 (1984)). This glycine modified thymidine analogue building block for chemical DNA synthesis can be used to substitute one or more of the thymidine/uridine nucleotides in the nucleic acid primer sequence. The Fmoc group is removed at the end of the solid phase synthesis with a 20 min treatment with a 20% solution of piperidine in DMF at room temperature. DMF is removed by a washing step with acetonitrile and the oligonucleotide deprotected and purified in the standard way.

EXAMPLE 7
Synthesis of a nucleic acid primer mass-modified at C-5 of the heterocyclic base of a pyrimidine nucleoside with β-alanine residues Starting material was the same as in EXAMPLE 6. 0.281 g (1.0 mmole) 5-(3-Aminopropynyl-1)-2'-deoxyuridine was reacted with N-Fmoc-β-alanine pentafluorophenylester (0.955 g, 2.0 mmole) in 5 ml N,N-dimethylformamide (DMF) in the presence of 0.129 g (174 ul; 1.0 mmole)

N,N-disopropylethylamine for 60 min at room temperature. Solvents were removed and the product purified by silica gel chromatography as described in EXAMPLE 6. Yield was 0.425 g (0.74 mmole, 74%). Another δ-alanine moiety can be added in exactly the same way after removal of the Fmoc group. The preparation of the 5'-O-dimethoxytritylated nucleoside-3'-O-β-cyanoethyl-N,N-diisopropylphosphoamidite from 5-(3-(N-Fmoc-β-alanyl)-amidopropynyl-1)-2'-deoxyuridine and incorporation into automated oligonucleotide synthesis is performed under standard conditions. This building block can substitute for any of the thymidine/uridine residues in the nucleic acid primer sequence. In the case of only one incorporated mass-modified nucleotide, the nucleic acid primer molecules prepared according to EXAMPLES 6 and 7 would have a mass difference of 14 daltons.

EXAMPLE 8

Synthesis of a nucleic acid primer mass-modified at C-5 of the heterocyclic base of a pyrimidine nucleoside with ethylene glycol monomethyl ether As a nucleosidic component, 5-(3-aminopropynyl-1)-2'-deoxyuridine was used in this example (see EXAMPLES 6 and 7). The mass-modifying functionality was obtained as follows: 7.61 g (100.0 mmole) freshly distilled ethylene glycol monomethyl ether dissolved in 50 ml absolute pyridine was reacted with 10.01 g (100.0 mmole) recrystallized succinic anhydride in the presence of 1.22 g (10.0 mmole) 4-N,N-dimethylaminopyridine overnight at room temperature. The reaction was terminated by the addition of water (5.0 ml), the reaction mixture evaporated in vacuo, co-evaporated twice with dry toluene (20 ml each) and the residue redissolved in 100 ml dichloromethane. The solution was extracted successively, twice with 10 % aqueous citric acid (2×20 ml) and once with water (20 ml) and the organic phase dried over anhydrous sodium sulfate. The organic phase was evaporated in vacuo, the residue redissolved in 50 ml dichloromethane and precipitated into 500 ml pentane and the precipitate dried in vacuo. Yield was 13.12 g (74.0 mmole; 74%). 8.86 g (50.0 mmole) of succinylated ethylene glycol monomethyl ether was dissolved in 100 ml dioxane containing 5% dry pyridine (5 ml) and 6.96 g (50.0 mmole) 4-nitrophenol and 10.32 g (50.0 mmole) dicyclohexylcarbodiimide was added and the reaction run at room temperature for 4 hours. Dicyclohexylurea was removed by filtration, the filtrate evaporated in vacuo and the residue redissolved in 50 ml anhydrous DMF. 12.5 ml (about 12.5 mmole 4-nitrophenylester) of this solution was used to dissolve 2.81 g (10.0 mmole) 5-(3-aminopropynyl-1)-2'-deoxyuridine. The reaction was performed in the presence of 1.01 g (10.0 mmole; 1.4 ml) triethylamine at room temperature overnight. The reaction mixture was evaporated in vacuo, co-evaporated with toluene, redissolved in dichloromethane and chromatographed on silicagel (Si60, Merck; column 4×50 cm) with dichloromethane/methanol mixtures. The fractions containing the desired compound were collected, evaporated, redissolved in 25 ml dichloromethane and precipitated into 250 ml pentane. The dried precipitate of 5-(3-N-(O-succinyl ethylene glycol monomethyl ether)-amidopropynyl-1)-2'-deoxyuridine (yield: 65%) is 5'-O-dimethoxytritylated and transformed into the nucleoside-3'-O-β-cyanoethyl-N, N-diisopropylphosphoamidite and incorporated as a building block in the automated oligonucleotide synthesis according to standard procedures. The mass-modified nucleotide can substitute for one or more of the thymidine/uridine residues in the nucleic acid primer sequence. Deprotection and purification of the primer oligonucleotide also follows standard procedures.

EXAMPLE 9

Synthesis of a nucleic acid primer mass-modified at C-5 of the heterocyclic base of a pyrimidine nucleoside with diethylene glycol monomethyl ether Nucleosidic starting material was as in previous examples, 5-(3-aminopropynyl-1)-2'-deoxyuridine. The mass-modifying functionality was obtained similar to EXAMPLE 8. 12.02 g (100.0 mmole) freshly distilled diethylene glycol monomethyl ether dissolved in 50 ml absolute pyridine was reacted with 10.01 g (100.0 mmole) recrystallized succinic anhydride in the presence of 1.22 g (10.0 mmole) 4-N,N-dimethylaminopyridine (DMAP) overnight at room temperature. The work-up was as described in EXAMPLE 8. Yield was 18.35 g (82.3 mmole, 82.3%). 11.06 g (50.0 mmole) of succinylated diethylene glycol monomethyl ether was transformed into the 4-nitrophenylester and, subsequently, 12.5 mmole was reacted with 2.81 g (10.0 mmole) of 5-(3-aminopropynyl-1)-2'-deoxyuridine as described in EXAMPLE 8. Yield after silica gel column chromatography and precipitation into pentane was 3.34 g (6.9 mmole, 69 %). After dimethoxytritylation and transformation into the nucleoside-β-cyanoethylphosphoamidite, the mass-modified building block is incorporated into automated chemical DNA synthesis according to standard procedures. Within the sequence of the nucleic acid primer $UP^{o-i}$, one or more of the thymidine/uridine residues can be substituted by this mass-modified nucleotide. In the case of only one incorporated mass-modified nucleotide, the nucleic acid primers of EXAMPLES 8 and 9 would have a mass difference of 44.05 daltons.

EXAMPLE 10

Synthesis of a nucleic acid primer mass-modified at C-8 of the heterocyclic base of deoxyadenosine with glycine Starting material was $N^6$-benzoyl-8-bromo-5'-O-(4,4'-dimethoxytrityl)-2'-deoxyadenosine prepared according to literature (Singh et al., *Nucleic Acids Res.* 18, 3339–45 (1990)). 632.5 mg (1.0 mmole) of this 8-bromo-deoxyadenosine derivative was suspended in 5 ml absolute ethanol and reacted with 251.2 mg (2.0 mmole) glycine methyl ester (hydrochloride) in the presence of 241.4 mg (2.1 mmole; 366 ul) N, N-diisopropylethylamine and refluxed until the starting nucleosidic material had disappeared (4–6 hours) as checked by thin layer chromatography (TLC). The solvent was evaporated and the residue purified by silica gel chromatography (column 2.5×50 cm) using solvent mixtures of chloroform/methanol containing 0.1% pyridine. The product fractions were combined, the solvent evaporated, the fractions dissolved in 5 ml dichloromethane and precipitated into 100 ml pentane. Yield was 487 mg (0.76 mmole, 76%). Transformation into the corresponding nucleoside-β-cyanoethylphosphoamidite and integration into automated chemical DNA synthesis is performed under standard conditions. During final deprotection with aqueous concentrated ammonia, the methyl group is removed from the glycine moiety. The mass-modified building block can substitute one or more deoxyadenosine/adenosine residues in the nucleic acid primer sequence.

EXAMPLE 11

Synthesis of a nucleic acid primer mass-modified at C-8 of the heterocyclic base of deoxyadenosine with glycylglycine This derivative was prepared in analogy to the glycine derivative of EXAMPLE 10. 632.5 mg (1.0 mmole) $N^6$-Benzoyl-8-bromo-5'-O-(4,4'-dimethoxytrityl)-2'-deoxyadenosine was suspended in 5 ml absolute ethanol and reacted with 324.3 mg (2.0 mmole) glycyl-glycine methyl ester in the presence of 241.4 mg (2.1 mmole, 366 μl) N,N-diisopropylethylamine. The mixture was refluxed and completeness of the reaction checked by TLC. Work-up and purification was similar to that described in EXAMPLE 10. Yield after silica gel column chromatography and precipitation into pentane was 464 mg (0.65 mmole, 65%). Transformation into the nucleoside-β-cyanoethylphosphoamidite and into synthetic oligonucleotides is done according to standard procedures. In the case where only one of the deoxyadenosine/adenosine residues in the nucleic acid primer is substituted by this mass-modified nucleotide, the mass difference between the nucleic acid primers of EXAMPLES 10 and 11 is 57.03 daltons.

EXAMPLE 12

Synthesis of a nucleic acid primer mass-modified at the C-2' of the sugar moiety of 2'-amino-2'-deoxythymidine with ethylene glycol monomethyl ether residues Starting material was 5'-O-(4,4-dimethoxytrityl)-2'-amino-2'-deoxythymidine synthesized according to published procedures (e.g., Verheyden et al., *J. Org. Chem.* 36, 250–254 (1971); Sasaki et al., *J. Org. Chem.* 41, 3138–3143 (1976); Imazawa et al., *J. Org. Chem.* 44, 2039–2041 (1979); Hobbs et al., *J. Org. Chem.* 42, 714–719 (1976); Ikehara et al., *Chem. Pharm. Bull. Japan* 36, 240–244 (1978); see also PCT Application WO 88/00201). 5'-O-(4,4-Dimethoxytrityl)-2'-amino-2'-deoxythymidine (559.62 mg; 1.0 mmole) was reacted with 2.0 mmole of the 4-nitrophenyl ester of succinylated ethylene glycol monomethyl ether (see EXAMPLE 8) in 10 ml dry DMF in the presence of 1.0 mmole (140 μl) triethylamine for 18 hours at room temperature. The reaction mixture was evaporated in vacuo, co-evaporated with toluene, redissolved in dichloromethane and purified by silica gel chromatography (Si60, Merck; column: 2.5×50 cm; eluent: chloroform/methanol mixtures containing 0.1% triethylamine). The product containing fractions were combined, evaporated and precipitated into pentane. Yield was 524 mg (0.73 mmol; 73%). Transformation into the nucleoside-β-cyanoethyl-N,N-diisopropylphosphoamidite and incorporation into the automated chemical DNA synthesis protocol is performed by standard procedures. The mass-modified deoxythymidine derivative can substitute for one or more of the thymidine residues in the nucleic acid primer.

In an analogous way, by employing the 4-nitrophenyl ester of succinylated diethylene glycol monomethyl ether (see EXAMPLE 9) and triethylene glycol monomethyl ether, the corresponding mass-modified oligonucleotides are prepared. In the case of only one incorporated mass-modified nucleoside within the sequence, the mass difference between the ethylene, diethylene and triethylene glycol derivatives is 44.05, 88.1 and 132.15 daltons respectively.

EXAMPLE 13

Synthesis of a nucleic acid primer mass-modified in the internucleotidic linkage via alkylation of phosphorothioate groups Phosphorothioate-containing oligonucleotides were prepared according to standard procedures (see e.g. Gait et al., *Nucleic Acids Res.,* 12 1183 (1991)). One, several or all internucleotide linkages can be modified in this way. The (—)-M13 nucleic acid primer sequence (17-mer) 5'-dGTAAAACGACOGCCAGT was synthesized in 0.25 μmole scale on a DNA synthesizer and one phosphorothioate group introduced after the final synthesis cycle (G to T coupling). Sulfurization, deprotection and purification followed standard protocols. Yield was 31.4 nmole (12.6% overall yield), corresponding to 31.4 nmole phosphorothioate groups. Alkylation was performed by dissolving the residue in 31.4 μl TE buffer (0.01 M Tris pH 8.0, 0.001 M EDTA) and by adding 16 μl of a solution of 20 mM solution of 2-iodoethanol (320 nmole; i.e., 10-fold excess with respect to phosphorothioate diesters) in N,N-dimethylformamide (DMF). The altylated oligonucleotide was purified by standard reversed phase HPLC (RP-1 8 Ultraphere, Beckman; column: 4.5×250 mm; 100 mM triethylammonium acetate, pH 7.0 and a gradient of 5 to 40% acetonitrile).

In a variation of this procedure, the nucleic acid primer containing one or more phosphorothioate phosphodiester bond is used in the Sanger sequencing reactions. The primer-extension products of the four sequencing reactions are purified as exemplified in EXAMPLES 1–4, cleaved off the solid support, lyophilized and dissolved in 4 μl each of TE buffer pH 8.0 and alkylated by addition of 2 μl of a 20 mM solution of 2-iodoethanol in DMF. It is then analyzed by ES and/or MALDI mass spectrometry.

In an analogous way, employing instead of 2-iodoethanol, e.g., 3-iodopropanol, 4-iodobutanol mass-modified nucleic acid primer are obtained with a mass difference of 14.03, 28.06 and 42.03 daltons respectively compared to the unmodified phosphorothioate phosphodiester-containing oligonucleotide.

EXAMPLE 14

Synthesis of 2'-amino-2'-deoxyuridine-5'-triphosphate and 3'-amino-2',3'-dideoxythymidine-5'-triphosphate mass-modified at the 2'- or 3'-amino function with glycine or β-alanine residues Starting material was 2'-azido-2'-deoxyuridine prepared according to literature (Verheyden et al., *J. Org. Chem* 36, 250 (1971)), which was 4,4-dimethoxytritylated at 5'-OH with 4,4-dimethoxytrityl chloride in pyridine and acetylated at 3'-OH with acetic anhydride in a one-pot reaction using standard reaction conditions. With 191 mg (0.71 mmole) 2'-azido-2'-deoxyuridine as starting material, 396 mg (0.65 mmol, 90.8%) 5'-O-(4,4-dimethoxytrityl)3'-O-acetyl-2'-azido-2'-deoxyuridine was obtained after purification via silica gel chromatography. Reduction of the azido group was performed using published conditions (Barta et al, *Tetrahedron* 46, 587–594 (1990)). Yield of 5'-O-(4,4-dimethoxytrityl)-3'-O-acetyl-2'-amino-2'-deoxyuridine after silica gel chromatography was 288 mg (0.49 mmole; 76%). This protected 2'-amino-2'-deoxyuridine derivative (588 mg, 1.0 mmole) was reacted with 2 equivalents (927 mg, 2.0 mmole) N-Fmoc-glycine pentafluorophenyl ester in 10 ml dry DMF overnight at room temperature in the presence of 1.0 mmole (174 μl) N,N-diisopropylethylamine. Solvents were removed by evaporation in vacuo and the residue purified by silica gel chromatography. Yield was 711 mg (0.71 mmole, 82%). Detritylation was achieved by a one hour treatment with 80% aqueous acetic acid at room temperature. The residue was evaporated to dryness, co-evaporated twice with toluene, suspended in 1 ml dry acetonitrile and 5'-phosphorylated with $POCl_3$ according to literature (Yoshikawa et al, *Bull. Chem. Soc. Japan* 48, 3505 (1969) and Sowa et al., *Bull. Chem. Soc. Japan* 48, 2084 (1975)) and directly transformed in a one-pot reaction to the 5'-triphosphate using 3 ml of a 0.5 M solution (1.5 mmole) tetra (tri-n-butylammonium) pyrophosphate in DMF according to literature (e.g. Seela et al., *Helvetica Chimica Acta* 74, 1048 (1991)). The Fmoc and the 3'-O-acetyl groups were removed by a one-hour treatment with concentrated aqueous ammonia at room temperature and the reaction mixture evaporated and lyophilized. Purification also followed standard procedures by using anion-exchange chromatography on DEAE-Sephadex with a linear gradient of triethylammonium bicarbonate (0.1 M–1.0 M). Triphosphate containing fractions (checked by thin layer chromatography on polyethyleneimine cellulose plates) were collected, evaporated and lyophilized. Yield (by UV-absorbance of the uracil moiety) was 68% (0.48 mmole).

A glycyl-glycine modified 2'-amino-2'-deoxyuridine-5'-triphosphate was obtained by removing the Fmoc group from 5'-O-(4,4-dimethoxytrityl)-3'-O-acetyl-2'-N-(N-9-fluorenylmethyloxycarbonyl-glycyl)-2'-amino-2'-deoxyuridine by a one-hour treatment with a 20% solution of piperidine in DMF at room temperature, evaporation of solvents, two-fold co-evaporation with toluene and subsequent condensation with N-Fmoc-glycine pentafluorophenyl ester. Starting with 1.0 mmole of the 2'-N-glycyl-2'-amino-2'-deoxyuridine derivative and following the procedure described above, 0.72 mmole (72%) of the corresponding 2'-(N-glycyl-glycyl)-2'-amino-2'-deoxyuridine-5'-triphosphate was obtained.

Starting with 5'-O-(4,4-dimethoxytrityl)-3'-O-acetyl-2'-amino-2'-deoxyuridine and coupling with N-Fmoc-$\beta$-alanine pentafluorophenyl ester, the corresponding 2'-(N-$\beta$-alanyl)-2'-amino-2'-deoxyuridine-5'-triphosphate can be synthesized. These modified nucleoside triphosphates are incorporated during the Sanger DNA sequencing process in the primer-extension products. The mass difference between the glycine, $\beta$-alanine and glycyl-glycine mass-modified nucleosides is, per nucleotide incorporated, 58.06, 72.09 and 115.1 daltons respectively.

When starting with 5'-O-(4,4-dimethoxytrityl)-3'-amino-2',3'-dideoxythymidine (obtained by published procedures, see EXAMPLE 12), the corresponding 3'-(N-glycyl)-3'-amino4 3'-(-N-glycyl-glycyl)-3'-amino-4 and 3'-N-$\beta$-alanyl)-3'-amino-2',3'-deoxythymidine-5'-triphosphates can be obtained. These mass-modified nucleoside triphosphates serve as a terminating nucleotide unit in the Sanger DNA sequencing reactions providing a mass difference per terminated fragment of 58.06, 72.09 and 115.1 daltons respectively when used in the multiplexing sequencing mode. The mass-differentiated fragments can then be analyzed by ES and/or MALDI mass spectrometry.

EXAMPLE 15

Synthesis of deoxyuridine-5'-triphosphate mass-modified at C-5 of the heterocyclic base with glycine, glycyl-glycine and $\beta$-alanine residues.

0.281 g (1.0 mmole) 5-(3-Aminopropynyl-1)-2'-deoxyuridine (see EXAMPLE 6) was reacted with either 0.927 g (2.0 mmole) N-Fmoc-glycine pentafluorophenylester or 0.955g (2.0 mmole) N-Fmoc-$\beta$-alanine pentafluorophenyl ester in 5 ml dry DMF in the presence of 0.129 g N,N-diisopropylethylamine (174 ul, 1.0 mmole) overnight at room temperature. Solvents were removed by evaporation in vacuo and the condensation products purified by flash chromatography on silica gel (Still et al., *J. Org. Chem.* 4, 2923–2925 (1978)). Yields were 476 mg (0.85 mmole: 85%) for the glycine and 436 mg (0.76 mmole; 76%) for the $\beta$-alanine derivatives. For the synthesis of the glycyl-glycine derivative, the Fmoc group of 1.0 mmole Fmoc-glycine-deoxyuridine derivative was removed by one-hour treatment with 20% piperidine in DMF at room temperature. Solvents were removed by evaporation in vacuo, the residue was co-evaporated twice with toluene and condensed with 0.927 g (2.0 mmole) N-Fmoc-glycine pentafluorophenyl ester and purified as described above. Yield was 445 mg (0.72 mmole; 30 72%). The glycyl-, glycyl-glycyl- and $\beta$-alanyl-2'-deoxyuridine derivatives, N-protected with the Fmoc group were transformed to the 3'-O-acetyl derivatives by tritylation with 4,4-dimethoxytrityl chloride in pyridine and acetylation with acetic anhydride in pyridine in a one-pot reaction and subsequently detritylated by one hour treatment with 80% aqueous acetic acid according to standard procedures. Solvents were removed, the residues dissolved in 100 ml chloroform and extracted twice with 50 ml 10% sodium bicarbonate and once with 50 ml water, dried with sodium sulfate, the solvent evaporated and the residues purified by flash chromatography on silica gel. Yields were 361 mg (0.60 mmole; 71%) for the glycyl-, 351 mg (0.57 mmole; 75%) for the $\beta$-alanyl- and 323 mg (0.49 mmole; 68%) for the glycyl-glycyl-3-O'-acetyl-2'-deoxyuridine derivatives respectively. Phosphorylation at the 5'-OH with $POCl_3$, transformation into the 5'-triphosphate by in-situ reaction with tetra(tri-n-butylammonium) pyrophosphate in DMF, 3'-de-O-acetylation, cleavage of the Fmoc group, and final purification by anion-exchange chromatography on DEAE-Sephadex was performed as described in EXAMPLE 14. Yields according to UV-absorbance of the uracil moiety were 0.41 mmole 5-(3-(N-glycyl)-amidopropynyl-1)-2'-deoxyurdine-5'-triphosphate (84%), 0.43 mmole 5-(3-(N-$\beta$-alanyl)-amidopropynyl-1)-2'-deoxyuridine-5'-triphosphate (75%) and 0.38 mmole 5-(3-(N-glycyl-glycyl)-amidopropynyl-1)-2'-deoxyuridine-5'-triphosphate (78%).

These mass-modified nucleoside triphosphates were incorporated during the Sanger DNA sequencing primer-extension reactions.

When using 5-(3-aminopropynyl-1)-2',3'-dideoxyuridine as starting material and following an analogous reaction sequence the corresponding glycyl-, glycyl-glycyl- and $\beta$-alanyl-2',3'-dideoxyuridine-5'-triphosphates were obtained in yields of 69, 63 and 71% respectively. These mass-modified nucleoside triphosphates serve as chain-terminating nucleotides during the Sanger DNA sequencing reactions. The mass-modified sequencing ladders are analyzed by either ES or MALDI mass spectrometry.

EXAMPLE 16

Synthesis of 8-glycyl- and 8-glycyl-glycyl-2'-deoxyadenosine-5'-triphosphate 727 mg (1.0 mmole) of $N^6$-(4-tert-butylphenoxyacetyl)8-glycyl-5'-(4,4-dimethoxytrityl)-2'-deoxyadenosine or 800 mg (1.0 mmole) $N^6$-(4tert-butylphenoxyacetyl)-8-glycyl-glycyl-5'-(4,4-dimethoxytrityl)-2'-deoxyadenosine prepared according to EXAMPLES 10 and 11 and literature (Köster et al., *Tetrahedron* 37, 362 (1981)) were acetylated with acetic anhydride in pyridine at the 3'-OH, detritylated at the 5'-position with 80% acetic acid in a one-pot reaction and transformed into the 5'-triphosphates via phosphorylation with $POCl_3$ and reaction in-situ with tetra(tri-n-butylammonium) pyrophosphate as described in EXAMPLE 14. Deprotection of the $N^6$-tert-butylphenoxyacetyl, the 3'-O-acetyl and the O-methyl group at the glycine residues was achieved with concentrated aqueous ammonia for ninety minutes at room temperature. Ammonia was removed by lyophilization and the residue washed with dichloromethane, solvent removed by evaporation in vacuo and the remaining solid material purified by anion-exchange chromatography on DEAE-Sephadex using a linear gradient of triethylammonium bicarbonate from 0.1 to 1.0 M. The nucleoside triphosphate containing fractions (checked by TLC on polyethyleneimine cellulose plates) were combined and lyophillized. Yield of the 8-glycyl-2'-deoxyadenosine-5'-triphosphate (determined by UV-absorbance of the adenine moiety) was 57% (0.57 mmole). The yield for the 8-glycyl-glycyl-2'-deoxyadenosine-5'-triphosphate was 51% (0.51 mmole).

These mass-modified nucleoside triphosphates were incorporated during primer-extension in the Sanger DNA sequencing reactions.

When using the corresponding N6-(4-tert-butylphenoxyacetyl)-8-glycyl- or glycyl-glycyl-5'-O-(4,4-dimethoxytrityl)2',3'-dideoxyadenosine derivatives as starting materials prepared according to standard procedures (see, e.g., for the introduction of the 2',3'-function: Seela et al., *Helvetica Chimica Acta* 74, 1048–1058 (1991)) and using an analogous reaction sequence as described above, the chain-terminating mass-modified nucleoside triphosphates 8-glycyl- and 8-glycyl-glycyl-2',3'-dideoxyadenosine-5'-triphosphates were obtained in 53 and 47% yields respectively. The mass-modified sequencing fragment ladders are analyzed by either ES or MALDI mass spectrometry.

EXAMPLE 17
Mass-modification of Sanger DNA sequencing fragment ladders by incorporation of chain-elongating 2'-deoxy- and chain-terminating 2',3'-dideoxythymidine-5'-(alpha-S-)-triphosphate and subsequent alkylation with 2-iodoethanol and 3-iodopropanol 2',3'-Dideoxythymidine-5'-(alpha-S)-triphosphate was prepared according to published procedures (e.g., for the alpha-S-triphosphate moiety: Eckstein et al., *Biochemistry* 15, 1685 (1976) and *Accounts Chem. Res.* 12, 204 (1978) and for the 2',3'-dideoxy moiety: Seela et al., *Helvetica Chimica Acta* 74, 1048–1058 (1991)). Sanger DNA sequencing reactions employing 2'-deoxythymidine-5'-(alpha-S)-triphosphate are performed according to standard protocols (e.g. Eckstein, *Ann. Rev. Biochem.* 54, 367 (1985)). When using 2',3'-dideoxythymidine-5'-(alpha-S)-triphosphates, this is used instead of the unmodified 2',3'-dideoxythymidine-5'-triphosphate in standard Sanger DNA sequencing (see e.g. Swerdlow et al., *Nucleic Acids Res.* 18, 1415–1419 (1990)). The template (2 pmole) and the nucleic acid M13 sequencing primer (4 pmole) modified according to EXAMPLE 1 are annealed by heating to 65° C. in 100 ul of 10 mM Tris-HCl pH 7.5, 10 mM $MgCl_2$, 50 mM NaCl, 7 mM dithiothreitol (DTT) for 5 min and slowly brought to 37° C. during a one hour period. The sequencing reaction mixtures contain, as exemplified for the T-specific termination reaction, in a final volume of 150 ul, 200 uM (final concentration) each of dATP, dCTP, dTTP, 300 uM c7-deaza-dGTP, 5 uM 2',3'-dideoxythymidine-5'-(alpha-S)-triphosphate and 40 units Sequenase (United States Biochemicals). Polymerization is performed for 10 min at 37° C., the reaction mixture heated to 70° C. to inactivate the Sequenase, ethanol precipitated and coupled to thiolated Sequelon membrane disks (8 mm diameter) as described in EXAMPLE 1. Alkylation is performed by treating the disks with 10 ul of 10 mM solution of either 2-iodoethanol or 3-iodopropanol in NMM (-methylmorpholine/water/2-propanol, 2/49/49, v/v/v) (three times), washing with 10 ul NMM (three times) and cleaving the alkylated T-terminated primer-extension products off the support by treatment with DTT as described in EXAMPLE 1. Analysis of the mass-modified fragment families is performed with either ES or MALDI mass spectrometry.

EXAMPLE 18
Analysis of a Mixture of Oligothymidylic Acids

Oligothymidylic acid, oligo $p(dT)_{12-18}$, is commercially available (United States Biochemical, Cleveland, Ohio). Generally, a matrix solution of 0.5 M in ethanol was prepared. Various matrices were used for this Example and Examples 19–21 such as 3,5-dihydroxybenzoic acid, sinapinic acid, 3-hydroxypicolinic acid, 2,4,6-trihydroxyacetophenone. Oligonucleotides were lyophilized after purification by HPLC and taken up in ultrapure water (MilliQ, Millipore) using amounts to obtain a concentration of 10 pmoles/)$\mu$l as stock solution. An aliquot (1$\mu$) of this concentration or a dilution in ultrapure water was mixed with 1 $\mu$l of the matrix solution on a flat metal surface serving as the probe tip and dried with a fan using cold air. In some experiments, cation-ion exchange beads in the acid form were added to the mixture of matrix and sample solution.

Figure 14:
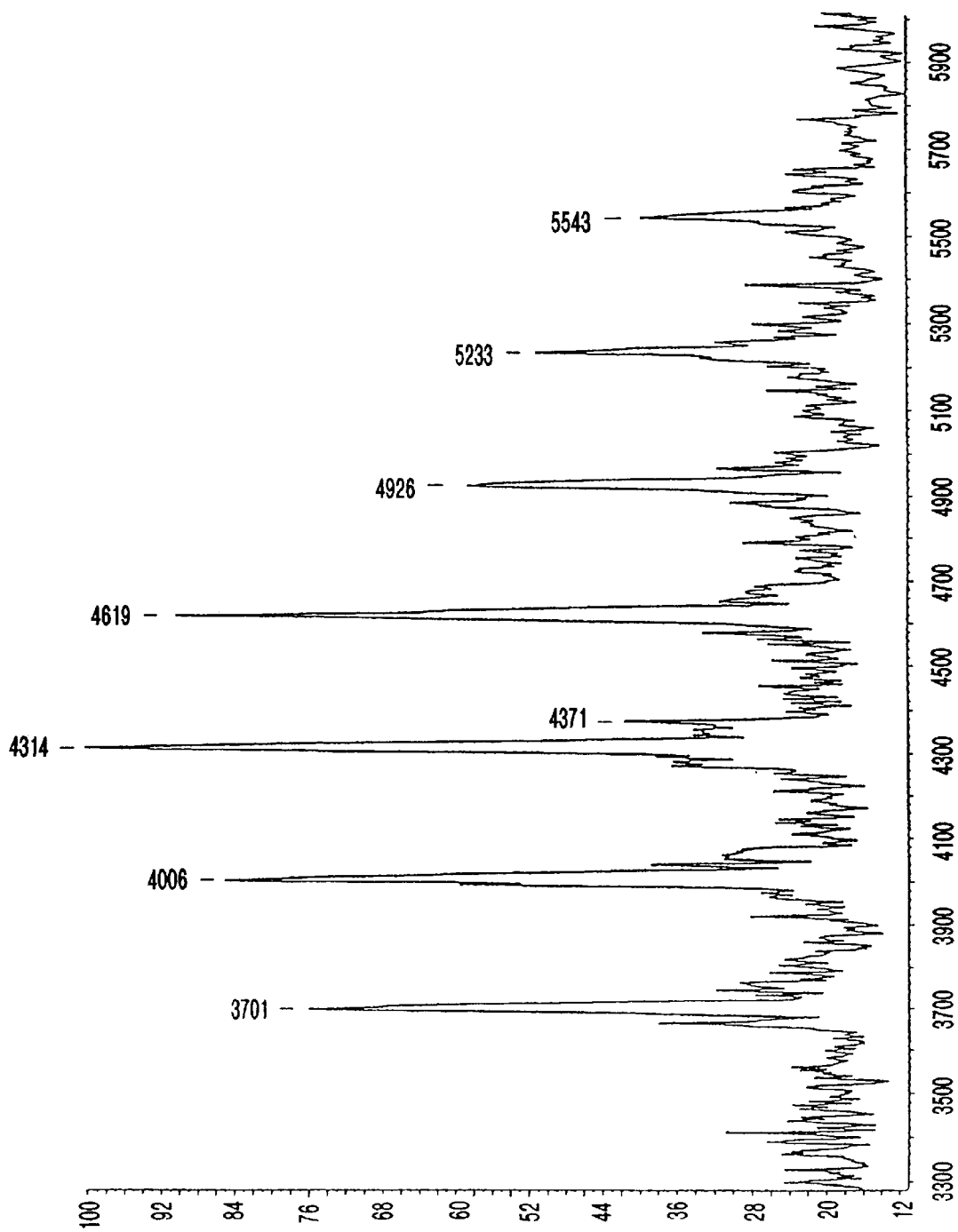
FIG. 14 shows a MALDI-TOF spectrum of a mixture of oligothymidylic acids, $d(pT)_{12-18}$.

MALDI-TOF spectra were obtained for this Example and Examples 19–21 on different commercial instruments such as Vision 2000 (Finnigan-MAT), VG TofSpec (Fisons Instruments), LaserTec Research (Vestec). The conditions for this Example were linear negative ion mode with an acceleration voltage of 25 kV. The MALDI-TOF spectrum generated is shown in FIG. 14. Mass calibration was done externally and generally achieved by using defined peptides of appropriate mass range such as insulin, gramicidin S, trypsinogen, bovine serum albumen, and cytochrome C. All spectra were generated by employing a nitrogen laser with 5 nsec pulses at a wavelength of 337 nm. Laser energy varied between $10^6$ and $10^7$ $W/cm^2$. To improve signal-to-noise ratio generally, the intensities of 10 to 30 laser shots were accumulated.

EXAMPLE 19
Mass Spectrometric Analysis of a 50-mer and a 99-mer

Figure 15:
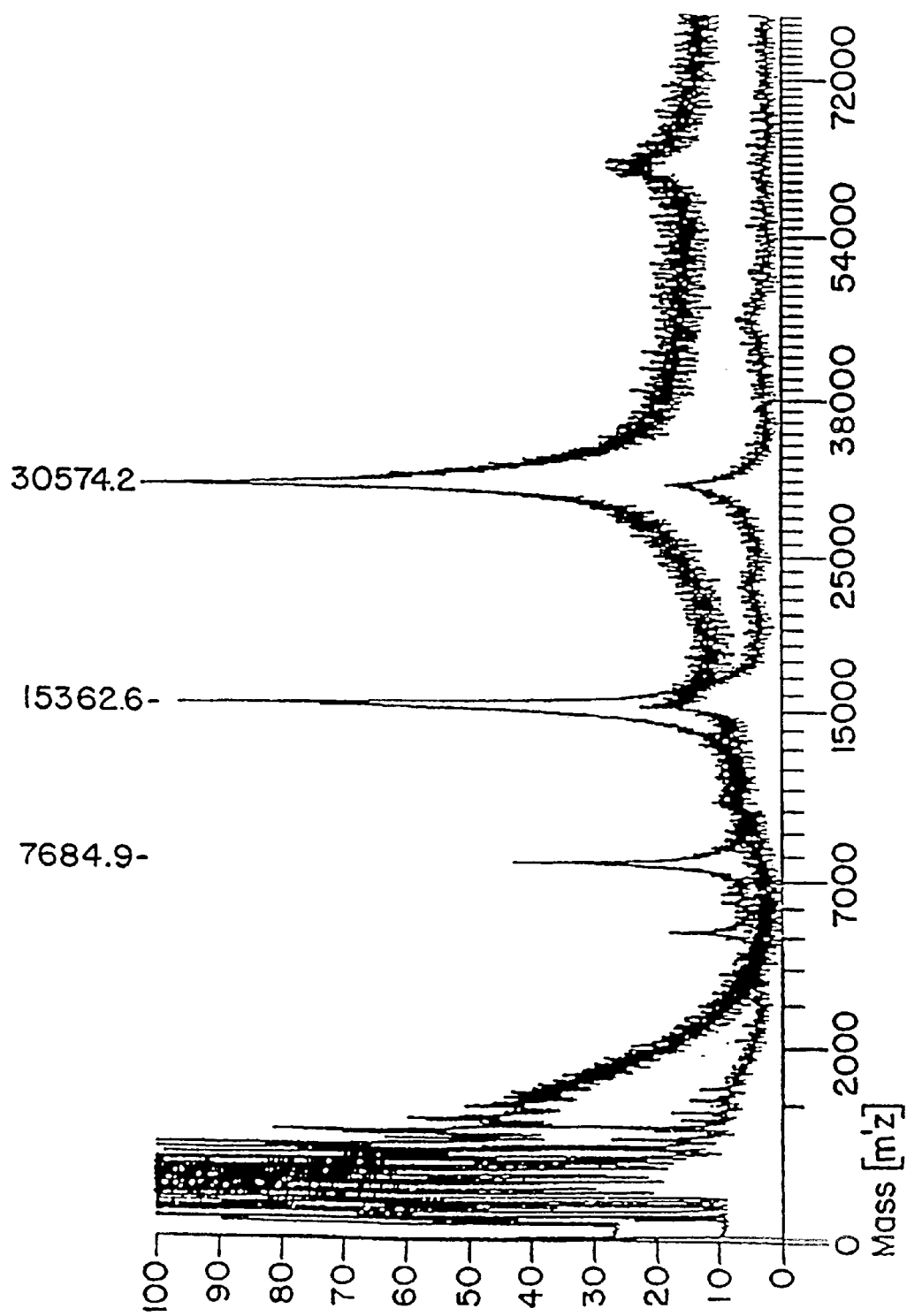
FIG. 15 shows a superposition of MALDI-TOF spectra of the 50-mer d(TAACGGTCATTACGGCCATTGACTGT-AGGACCTGCATTACATGACTAGCT) (SEQ ID NO:3) (500 fmol) and $dT(pdT)_{99}$ (500 fmol).
Figure 16A:
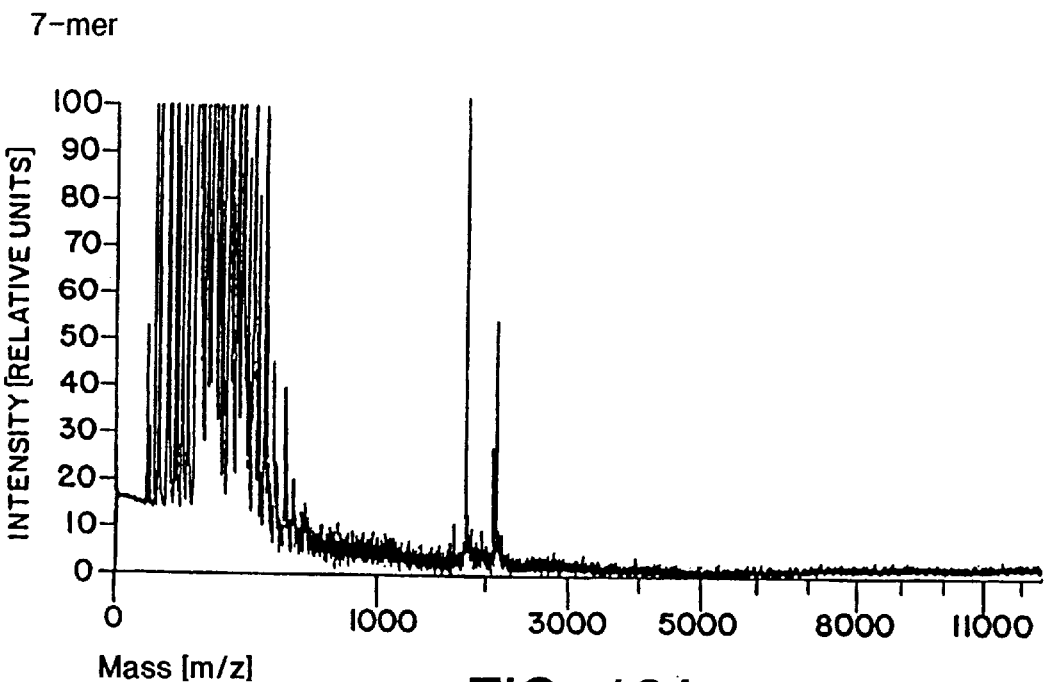
FIGS. 16A–16M show the MALDI-TOF spectra of all 13 DNA sequences representing the nested dT-terminated fragments of the Sanger DNA sequencing simulation of FIG. 2, 500 fmol each.
Figure 16B:
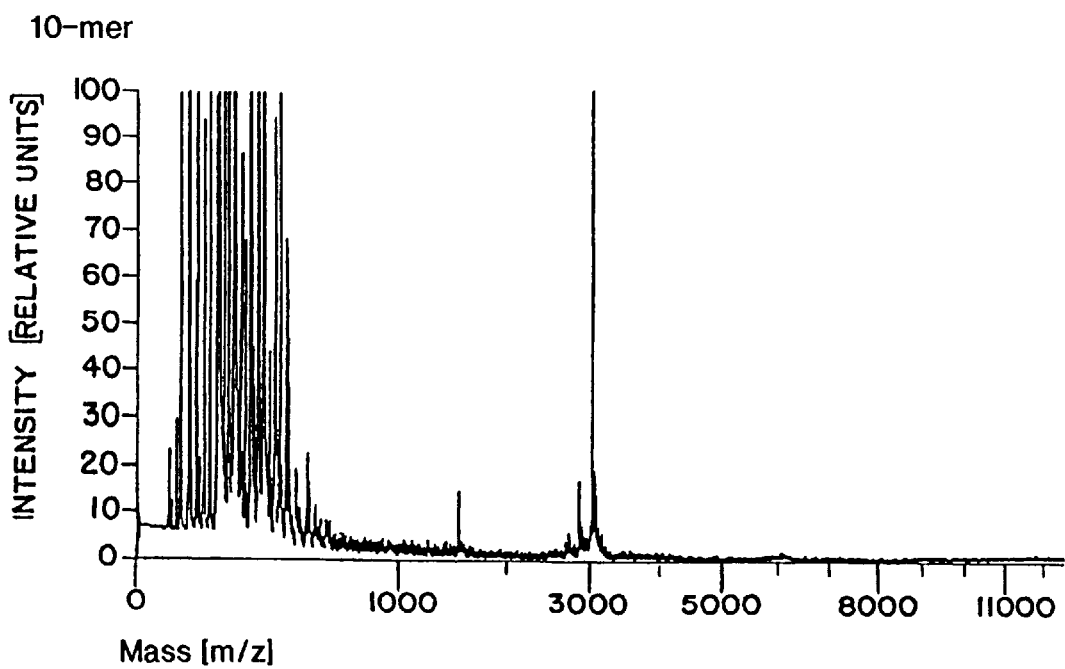
Figure 16C:
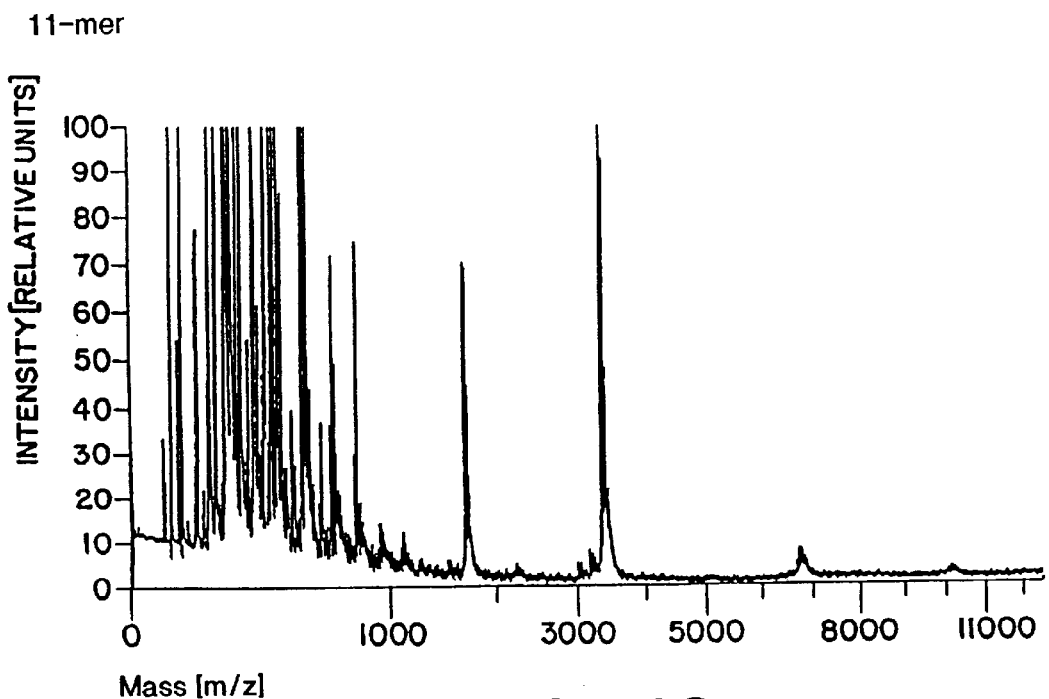
Figure 16D:
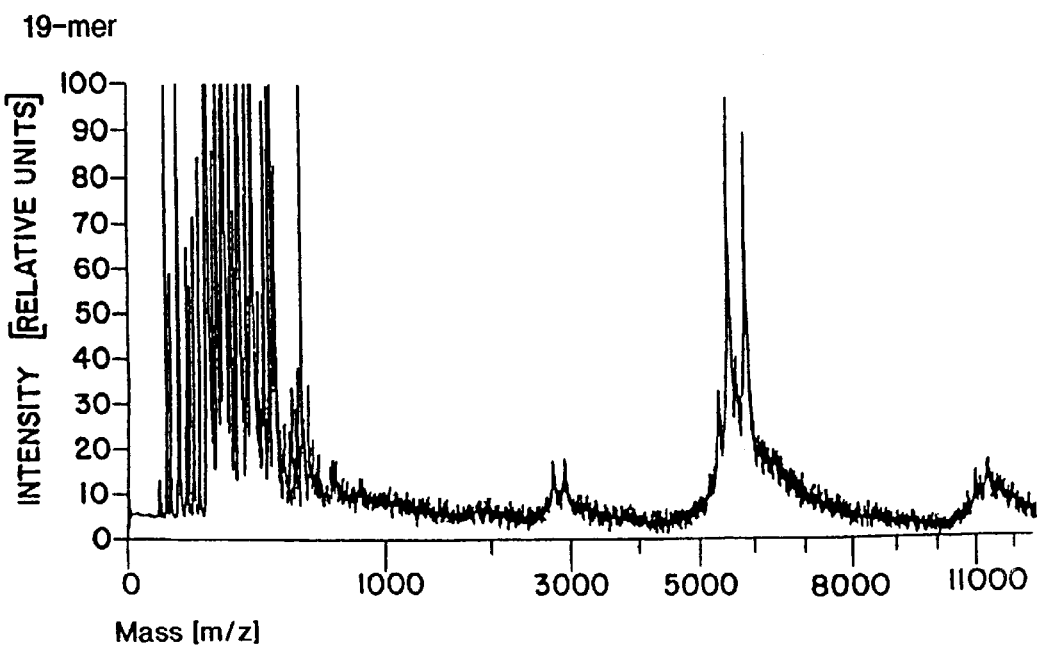
Figure 16E:
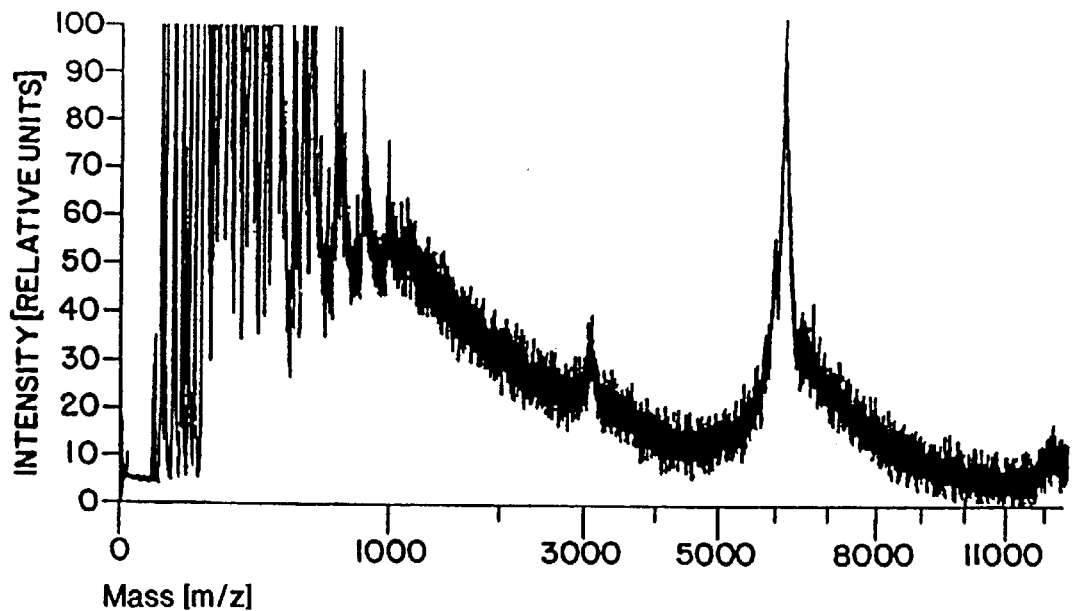
Figure 16F:
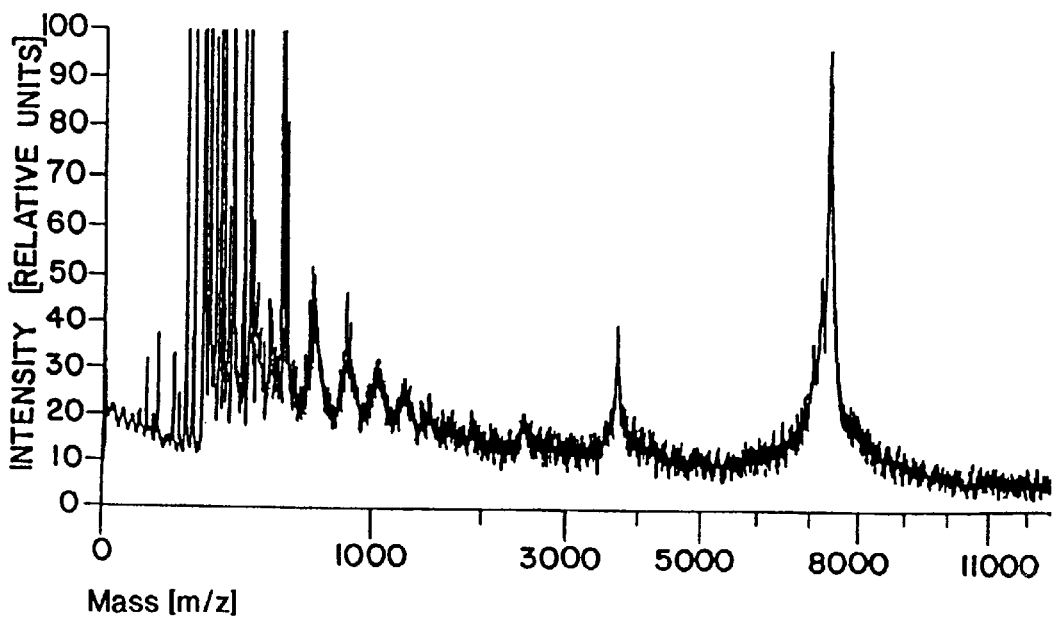
Figure 16G:
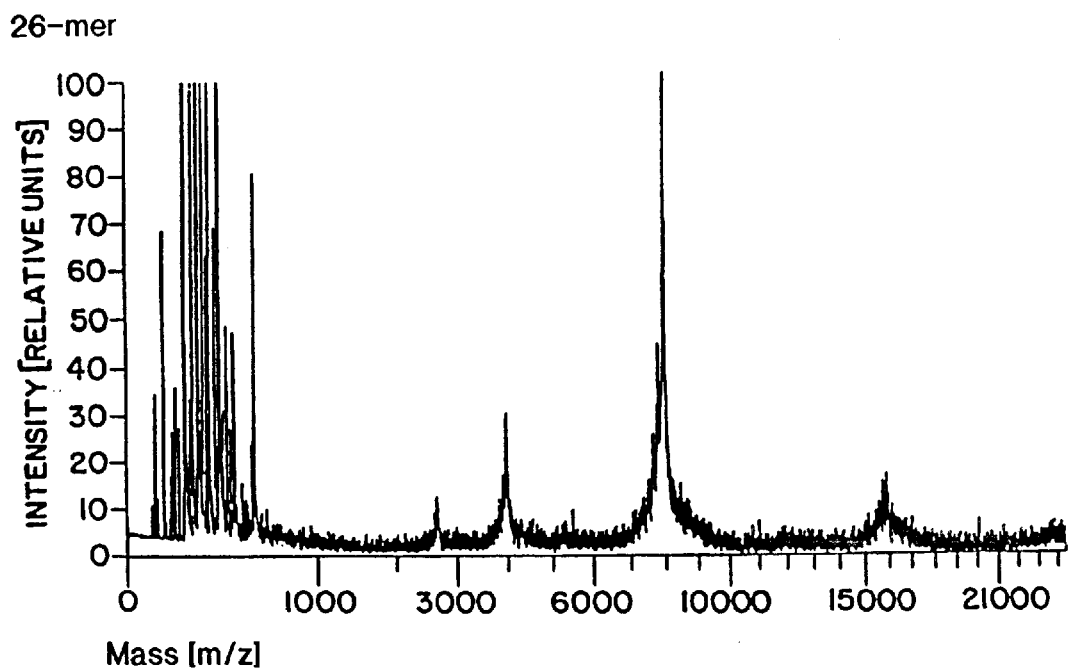
Figure 16H:
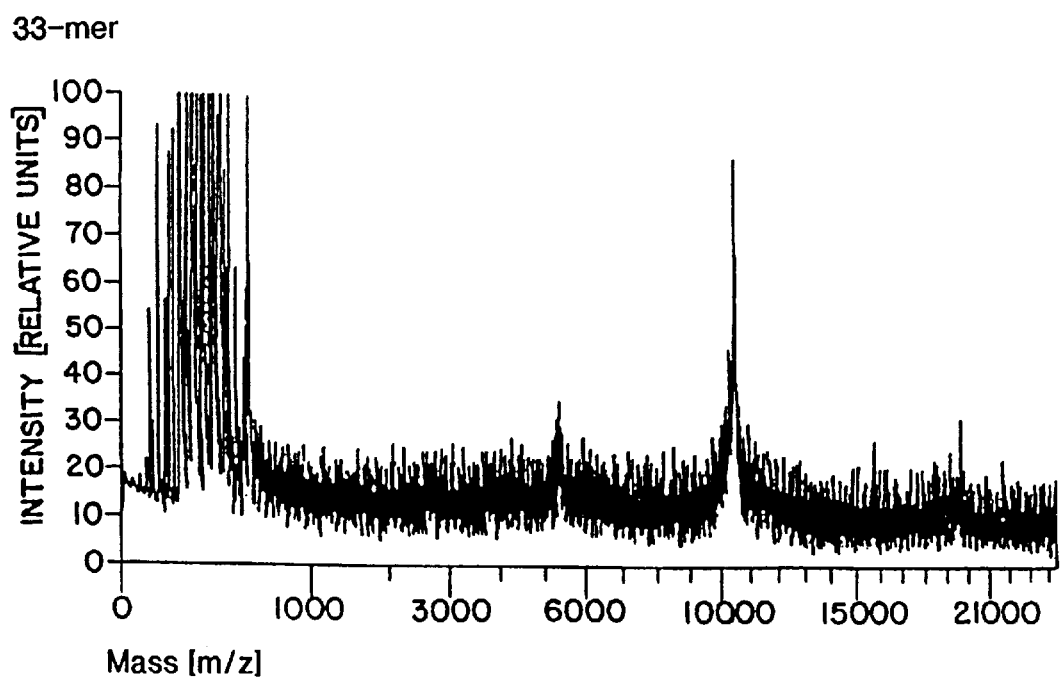
Figure 16I:
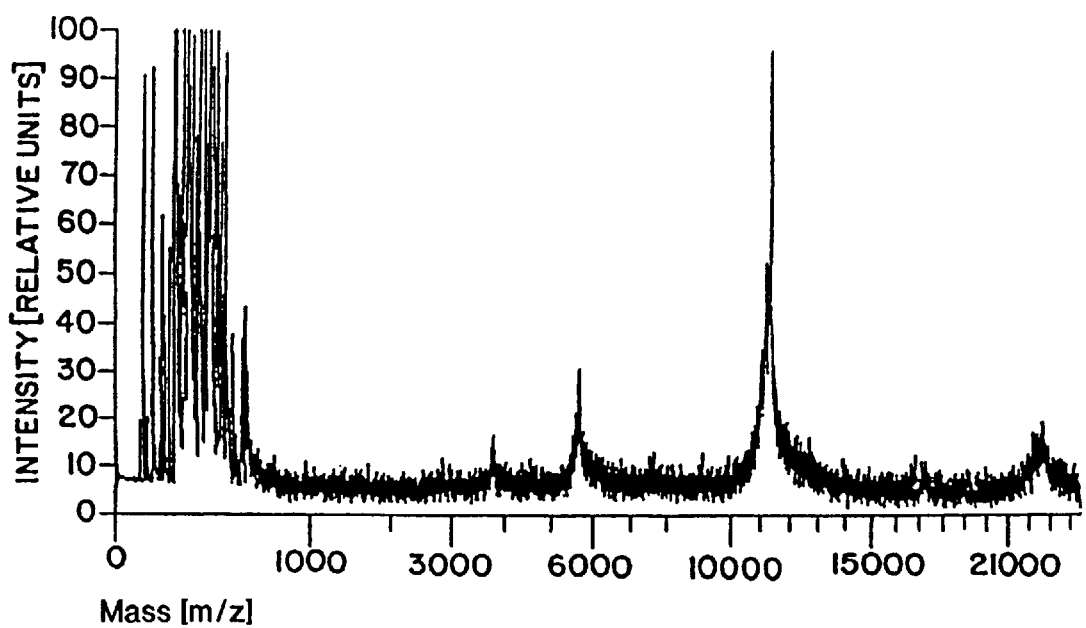
Figure 16J:
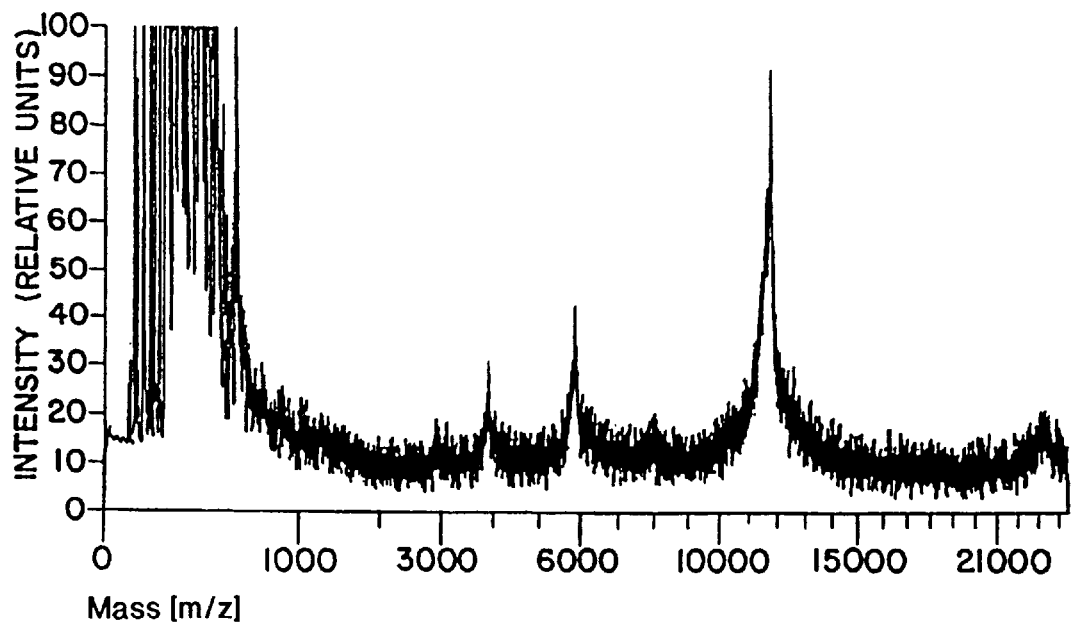
Figure 16K:
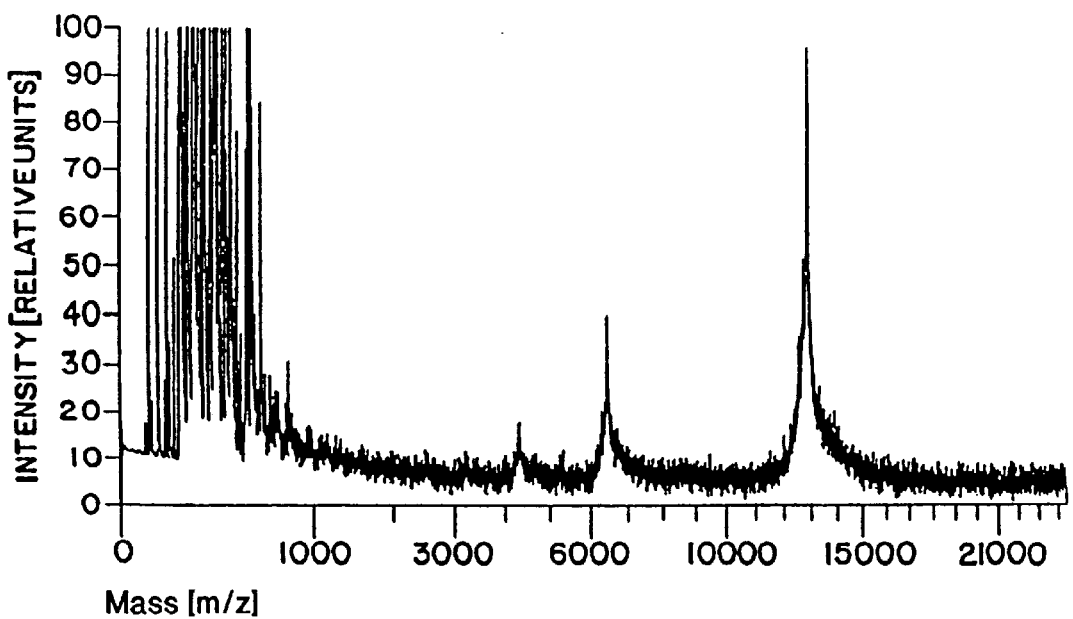
Figure 16L:
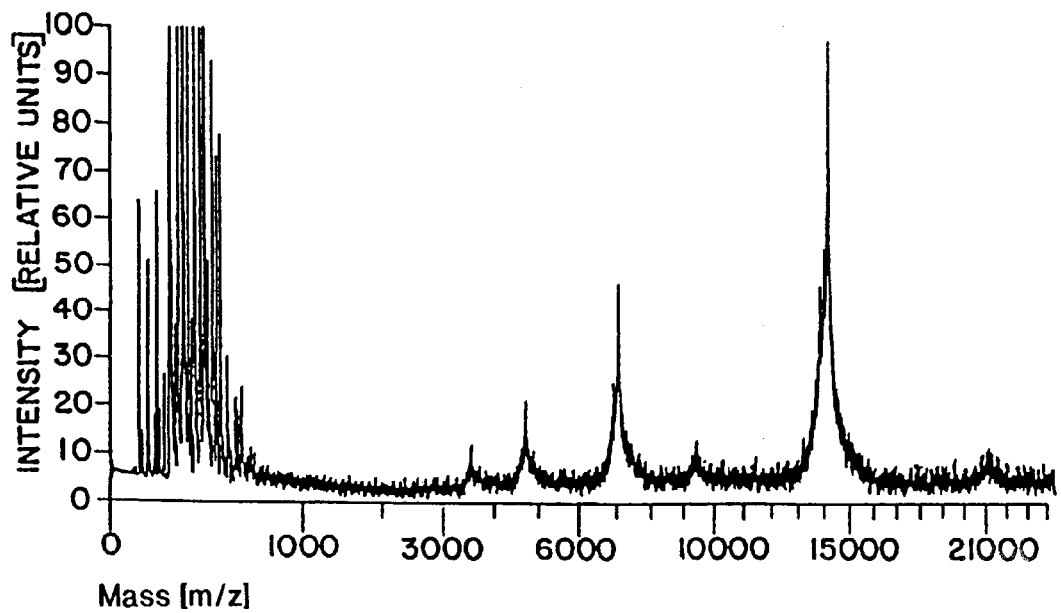
Figure 16M:
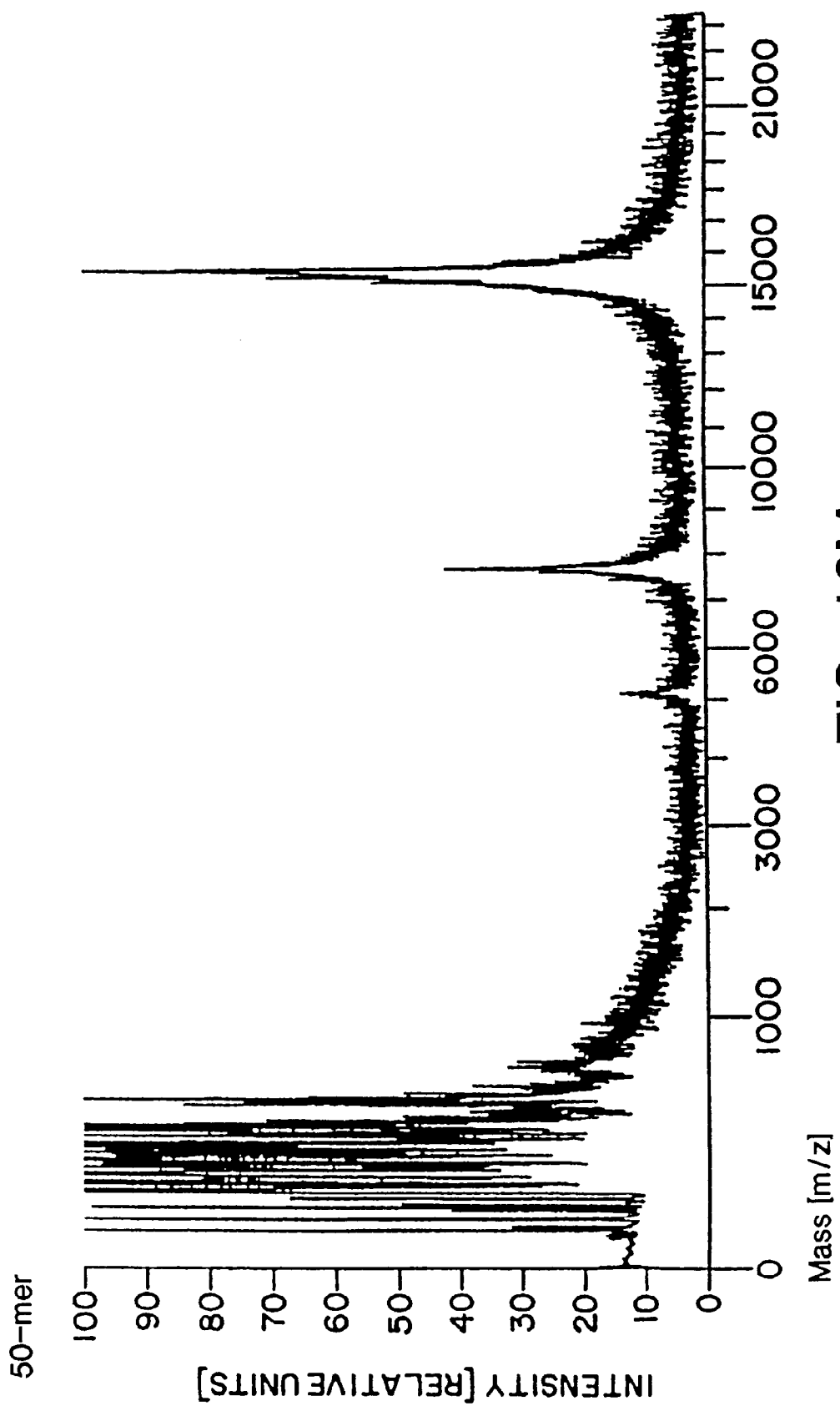

Two large oligonucleotides were analyzed by mass spectrometry. The 50-mer d(TAACGGTCATTACGGCCATTGACTGTAGGACCTG-CATTACATGACTAGCT) (SEQ ID NO:3) and dT(pdT)gg were used. The oligodeoxynucleotides were synthesized using β-cyanoethylphosphoamidites and purified using published procedures.(e.g. N. D. Sinha, J. Biernat, J. McManus and H. Köster, *Nucleic Acids Res.*, 12, 4539 (1984)) employing commercially available DNA synthesizers from either Millipore (Bedford, Mass.) or Applied Biosystems (Foster City, Calif.) and HPLC equipment and RP18 reverse phase columns from Waters (Milford, Mass.). The samples for mass spectrometric analysis were prepared as described in Example 18. The conditions used for MALDI-MS analysis of each oligonucleotide were 500 fmol of each oligonucleotide, reflectron positive ion mode with an acceleration of 5 kV and postacceleration of 20 kV. The MALDI-TOF spectra generated were superimposed and are shown in FIG. 15.

EXAMPLE 20
Simulation of the DNA Sequencing Results of FIG. 2

The 13 DNA sequences representing the nested dT-terminated fragments of the Sanger DNA sequencing for the 50-mer described in Example 19 (SEQ ID NO:3) were synthesized as described in Example 19. The samples were treated and 500 fmol of each fragment was analyzed by MALDI-MS as described in Example 18. The resulting MALDI-TOF spectra are shown in FIG. 16. The conditions were reflectron positive ion mode with an acceleration of 5 kV and postacceleration of 20 kV. Calculated molecular masses and experimental molecular masses are shown in Table 1.

The MALDI-TOF spectra were superimposed (FIG. 17) to demonstrate that the individual peaks are resolvable even between the 10-mer and 11-mer (upper panel) and the 37-mer and 38-mer (lower panel). The two panels show two different scales and the spectra analyzed at that scale.

EXAMPLE 2
MALDI-MS Analysis of a Mass-Modified Oligonucleotide

A 17-mer was mass-modified at C-5 of one or two deoxyuridine moieties. 5-[13-(2-Methoxyethoxyl)- tridecyne-1-yl]-5'-O-(4,4'-dimethoxytrityl)-2'-deoxyuridine-3'-β-cyanoetlyl-N,N-diisopropylphosphoamidite was used to synthesize the modified 1 7-mers using the methods described in Example 19.

The modified 7-mers were

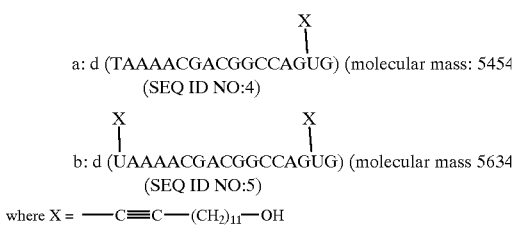

where X = —C≡C—(CH$_2$)$_{11}$—OH (unmodified 17-mer: molecular mass: 5273)

Figure 18:
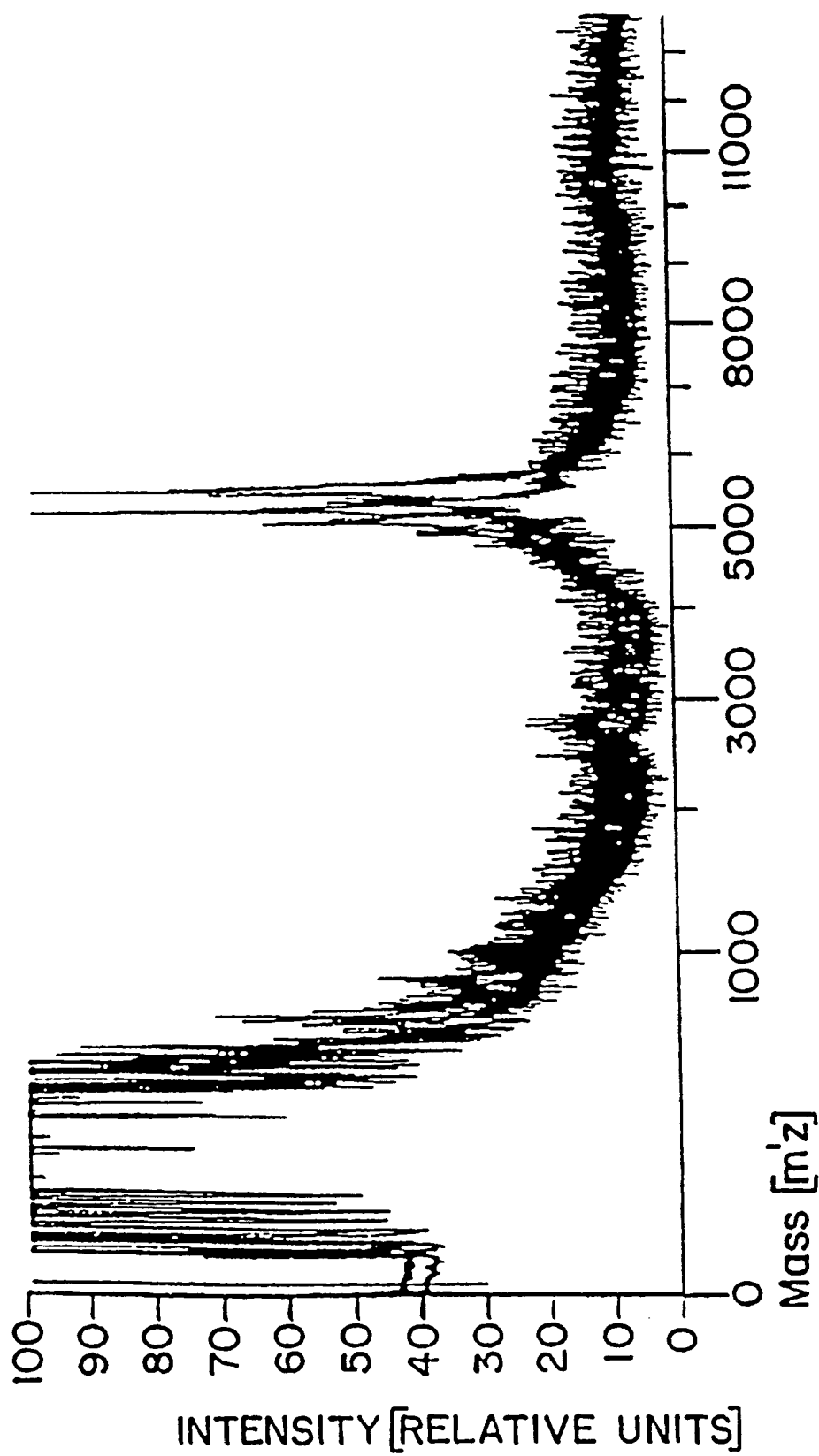
FIG. 18 shows the superimposed MALDI-TOF spectra from MALDI-MS analysis of mass-modified oligonucleotides as described in Example 21.

The samples were prepared and 500 fmol of each modified 17-mer was analyzed using MALDI-MS as described in Example 18. The conditions used were reflectron positive ion mode with an acceleration of 5 kV and postacceleration of 20 kV. The MALDI-TOF spectra which were generated were superimposed and are shown in FIG. 18.

All of the above-cited references and publications are hereby incorporated by reference.

EQUIVALENTS

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. An intact ionized and volatilized mass-modified nucleic acid molecule, comprising at least two mass modified nucleotides, wherein the molecule is positively charged.

2. An intact ionized mass-modified nucleic acid molecule, comprising:
at least one mass modified nucleotide, wherein the molecule is positively charged, and comprises a member selected from the group consisting of: a mass-modified universal primer and a mass-modified initiator oligonucleotide.

3. An intact ionized mass-modified nucleic acid molecule of claim 1, comprising at least one mass-modified nucleotide containing a mass-modifying functionality (M) attached to a heterocyclic base of the nucleotide.

4. An intact positively charged ionized mass-modified nucleic acid molecule, comprising:
at least one mass-modified nucleotide containing a modified heterocyclic base selected from a group consisting of a cytosine moiety modified at C-5, a thymine moiety modified at C-5, a thymine moiety modified at the methyl group of C-5, a uracil moiety modified at C-5, an adenine moiety modified at C-8, a $c^7$-deazaadenine moiety modified at C-8, a $c^7$-deazaadenine moiety modified at C-7, a guanine moiety modified at C-8, a $c^7$-deazaguanine moiety modified at C-8, a $c^7$-deazaguanine moiety modified at C-7, a hypoxanthine moiety modified at C-8, a $c^7$-deazahypoxanthine moiety modified at C-8, and a $c^7$-deazahypoxanthine moiety modified at C-7.

5. An intact ionized mass-modified nucleic acid molecule of claim 1, comprising at least one mass-modified nucleotide containing a mass-modifying functionality (M) attached to at least one phosphorus of the nucleotide.

6. An intact positively charged ionized mass-modified nucleic acid molecule, comprising:
at least one mass-modified nucleotide containing a mass-modifying functionality (M) attached to at least one sugar moiety of the nucleotide.

7. An intact positively charged ionized mass-modified nucleic acid molecule, comprising:
a mass-modifying functionality (M) attached to at least one sugar moiety of the nucleic acid molecule, wherein the sugar is modified at a position selected from the group consisting of an internal C-2' position, an external C-2' position, and an external C-5' position.

8. An ionized mass-modified nucleic acid molecule of claim 2, wherein a mass-modifying functionality (M) is attached to at least one sugar moiety of a 5'-terminal nucleotide of the primer, and wherein the mass-modifying function (M) is a linking functionality (L).

9. An intact ionized mass-modified nucleic acid molecule, comprising at least one mass-modified nucleotide containing a mass-modifying functionality (M) incorporated into the molecule, wherein (M) is selected from the group consisting of F, Cl, Br, I, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$.

10. An intact positively charged ionized mass-modified nucleic acid molecule, comprising:
at least two mass-modified nucleotides, wherein a mass-modifying functionality (M) incorporated into the at least one mass-modified nucleotide is generated from a precursor functionality (PF) attached to one or more of a nucleic acid primer, a chain-elongating nucleoside triphosphate or a chain-terminating nucleoside triphosphate, and wherein the precursor functionality (PF) is selected from the group consisting of $—N_3$, $—NH_2$, $—SH$, $—NCS$, $—OCO(CH_2)_r COOH$ (where r=1–20), —NHCO(CH$_2$)$_r$COOH (where r=1–20), —OSO$_2$OH, —OCO(CH$_2$)$_r$I (where r=1–20), and —OP(O-Alkyl)N(Alkyl)$_2$.

11. An ionized intact mass-modified nucleic acid molecule of claim 1, wherein a mass-modifying functionality (M) incorporated into the molecule is XR, wherein X is selected from the group consisting of —O—, —NH—, —S—, —NHC(S)—, —OCO(CH$_2$)$_r$COO— (where r=1–20), —NHCO(CH$_2$)$_r$COO— (where r=1–20), —OSO$_2$O— and R is selected from the group consisting of H, methyl, ethyl, propyl, isopropyl, t-butyl, hexyl, benzyl, benzhydryl, halogen, trityl, substituted trityl, aryl, substituted aryl, polyoxymethylene, monoalkylated polyoxymethylene, a polyethylene imine, —(NH(CH$_2$)$_r$NHCO(CH$_2$)$_r$CO—)$_m$—NH—(CH$_2$)$_r$—NH—CO—(CH$_2$)$_r$—COOH, —(NH(CH$_2$)$_r$CO—)$_m$—NH—(CH$_2$)$_r$—COOH, —(O(CH$_2$)$_r$CO—)$_m$—O—(CH$_2$)$_r$—COOH, —Si(Y)$_3$, —(NHCHaaCOOH), —(CH$_2$CH$_2$O)$_m$—CH$_2$CH$_2$OH, and —(CH$_2$CH$_2$O)$_m$—CH$_2$CH$_2$O—Y, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

12. A set of mass-differentiated tag probes wherein,
each tag probe in the set comprises a sequence of nucleotides which is complementary by Watson-Crick base pairing to a tag sequence present within at least one set of base-specifically terminated fragments;
the tag sequences to which each tag probe is complementary are different for each tag probe;
each tag probe in the set comprises at least one mass-modified nucleotide; and
the mass-modified nucleotides are not isotopically labeled and have different mass modifications in each tag probe.

13. The set of mass-differentiated tag probes of claim 12, wherein at least one of the mass-modified nucleotides comprises a mass-modifying functionality (M) attached to the heterocyclic base.

14. The set of mass-differentiated tag probes of claim 13, wherein the mass-modified heterocyclic base is selected from the group consisting of a cytosine moiety modified at C-5, a thymine moiety modified at C-5, a thymine moiety modified at the C-5 methyl group, a uracil moiety modified at C-5, an adenine moiety modified at C-8, a c$^7$-deazaadenine moiety modified at C-8, a, a c$^7$-deazaadenine moiety modified at C-7, a guanine moiety modified at C-8, a c$^7$-deazaguanine moiety modified at C-8, a c$^7$-deazaguanine moiety modified at C-7, a hypoxanthine moiety modified at C-8, a c$^7$-deazahypoxanthine moiety modified at C-8, and a c$^7$-deazahypoxanthine moiety modified at C-7.

15. The set of mass-differentiated tag probes of claim 12, wherein at least one of the mass-modified nucleotides comprises a mass-modifying functionality (M) attached to the phosphorus atom forming an internucleotidic linkage of the tag probe.

16. The set of mass-differentiated tag probes of claim 12, wherein at least one of the mass-modified nucleotides comprises a mass-modifying functionality (M) attached to the sugar moiety.

17. The set of mass-differentiated tag probes of claim 12, wherein at least one of the tag probes further comprises a cross-linking group (CL) which allows for covalent binding to the corresponding and complementary tag sequences.

18. The set of mass-differentiated tag probes of claim 17, wherein the cross-linking group (CL) is activated photochemically and is derived from at least one photoactivatable group selected from the group consisting of psoralen and an ellipticine.

19. The set of mass-differentiated tag probes of claim 12, wherein at least one of the tag probes is mass-modified with a mass-modifying functionality (M) selected from the group consisting of XR, F, Cl, Br, I, Si(CH$_3$)$_3$, Si(CH$_3$)$_2$(C$_2$H$_5$), Si(CH$_3$)(C$_2$H$_5$)$_2$, Si(C$_2$H$_5$)$_3$, CH$_2$F, CHF$_2$, and CF$_3$, wherein X is selected from the group consisting of —O—, —NH—, —S—, —NHC(S)—, —OCO(CH$_2$)$_r$COO— (where r=1–20), —NHCO(CH$_2$)$_r$COO— (where r=1–20), —OSO$_2$O—, and R is selected from the group consisting of H, methyl, ethyl, propyl, isopropyl, t-butyl, hexyl, benzyl, benzhydryl, halogen, trityl, substituted trityl, aryl, substituted aryl, polyoxymethylene, monoalkylated polyoxymethylene, a polyethylene imine, —(NH(CH$_2$)$_r$NHCO(CH$_2$)$_r$CO—)$_m$—NH—(CH$_2$)$_r$—NH—CO—(CH$_2$)$_r$—COOH, —(NH(CH$_2$)$_r$CO—)$_m$—NH—(CH$_2$)$_r$—COOH, —(O(CH$_2$)$_r$CO—)$_m$—O—(CH$_2$)$_r$—COOH, —Si(Y)$_3$, —(NHCHaaCOOH), —(CH$_2$CH$_2$O)$_m$—CH$_2$CH$_2$OH, and —(CH$_2$CH$_2$O)$_m$—CH$_2$CH$_2$O—Y, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

20. The set of mass-differentiated tag probes of claim 12, wherein one or more mass-modifying functionalities (M) incorporated into the probes are generated from one or more precursor functionalities (PF) attached to the mass-differentiated tag probes, and wherein the precursor functionalities (PF) are selected from a group consisting of —N$_3$, —NH$_2$, —SH, —NCS, —OCO(CH$_2$)$_r$COOH (where r=1–20), —NHCO(CH$_2$)$_r$COOH (where r=1–20), —OSO$_2$OH, —OCO(CH$_2$)$_r$I (where r=1–20), and —OP(O-Alkyl)N(Alkyl)$_2$.

21. An intact positively charged ionized mass-modified nucleic acid molecule, comprising:
two or more mass modified nucleotides selected from the group consisting of a mass-modified 2'-deoxynucleotide, a mass-modified 2',3'-dideoxynucleotide, a mass-modified nucleotide and a mass-modified 3'-deoxynucleotide, wherein the two or more mass-modified nucleotides are different from each other.

22. An ionized mass-modified nucleic acid molecule, comprising at least one mass modified nucleotide selected from the group consisting of a mass-modified 2'-deoxynucleotide, a mass-modified 2',3'-dideoxynucleotide, a mass-modified nucleotide and a mass-modified 3'-deoxynucleotide, wherein the mass modified nucleic acid molecule comprises a modified heterocyclic base selected from a group consisting of modified heterocyclic base is a c$^7$-deazaadenine moiety modified at C-8, a c$^7$-deazaadenine moiety modified at C-7, a c$^7$-deazaguanine moiety modified at C-8, a c$^7$-deazaguanine moiety modified at C-7, a hypoxanthine moiety modified at C-8, a c$^7$-deazahypoxanthine moiety modified at C-8, and a c$^7$-deazahypoxanthine moiety modified at C-7.

23. An ionized positively charged intact duplex, comprising a mass-modified tag probe bound to a tag sequence present within a base-specifically terminated nucleic acid fragment, wherein the mass-modified tag probe comprises at least one mass-modified nucleotide.

24. An ionized intact duplex, comprising a mass-modified tag probe bound to a tag sequence present within a base-specifically terminated nucleic acid fragment, wherein the mass-modified tag probe comprises at least one mass-modified nucleotide, wherein at least one of the mass-modified nucleotides comprises a mass-modifying functionality (M) attached to the heterocyclic base.

25. The ionized duplex of claim 24, wherein the mass-modified heterocyclic base is selected from the group consisting of a cytosine moiety modified at C-5, a thymine moiety modified at C-5, a thymine moiety modified at the C-5 methyl group, a uracil moiety modified at C-5, an adenine moiety modified at C-8, a $c^7$-deazaadenine moiety modified at C-8, a, a $c^7$-deazaadenine moiety modified at C-7, a guanine moiety modified at C-8, a $c^7$-deazaguanine moiety modified at C-8, a $c^7$-deazaguanine moiety modified at C-7, a hypoxanthine moiety modified at C-8, a $c^7$-deazahypoxanthine moiety modified at C-8, and a $c^7$-deazahypoxanthine moiety modified at C-7.

26. An ionized intact duplex, comprising a mass-modified tag probe bound to a tag sequence present within a base-specifically terminated nucleic acid fragment, wherein: the mass-modified tag probe comprises at least one mass-modified nucleotide; and a mass-modifying functionality (M) incorporated into the tag probe is attached to the phosphorus atom forming an internucleotidic linkage of the tag probe.

27. An ionized intact duplex, comprising a mass-modified tag probe bound to a tag sequence present within a base-specifically terminated nucleic acid fragment, wherein: the mass-modified tag probe comprises at least one mass-modified nucleotide; and at least one of the mass-modified nucleotides comprises a mass-modifying functionality (M) attached to the sugar moiety.

28. An ionized intact duplex, comprising a mass-modified tag probe bound to a tag sequence present within a base-specifically terminated nucleic acid fragment, wherein: the mass-modified tag probe comprises at least one mass-modified nucleotide; and the tag probe further comprises a cross-linking group (CL) which allows for covalent binding to the tag sequence.

29. The ionized duplex of claim 28, wherein the cross-linking group (CL) is activated photochemically and is derived from at least one photoactivatable group selected from the group consisting of psoralen and an ellipticine.

30. An ionized intact duplex, comprising a mass-modified tag probe bound to a tag sequence present within a base-specifically terminated nucleic acid fragment, wherein: the mass-modified tag probe comprises at least one mass-modified nucleotide; and the tag probe is mass-modified with a mass-modifying functionality (M) selected from the group consisting of XR, F, Cl, Br, I, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$) wherein X is selected from the group consisting of —O—, —NH—, —S—, —NHC(S)—, —OCO$(CH_2)_r$COO— (where r=1–20), —NHCO$(CH_2)_r$COO— (where r=1–20), —OSO$_2$O— and —OP(O-Alkyl)O— and R is selected from the group consisting of H, methyl, ethyl, propyl, isopropyl, t-butyl, hexyl, benzyl, benzhydryl, halogen, trityl, substituted trityl, aryl, substituted aryl, polyoxymethylene, monoalkylated polyoxymethylene, a polyethylene imine, —(NH$(CH_2)_r$NHCO$(CH_2)_r$CO—$)_m$—NH—$(CH_2)_r$—NH—CO—$(CH_2)_r$—COOH, —(NH$(CH_2)_r$CO—$)_m$—NH—$(CH_2)_r$—COOH, —O$(CH_2)_r$CO—$)_m$—O—$(CH_2)_r$—COOH, —Si(Y)$_3$, —(NHCHaaCO)$_m$—HCHaaCOOH, —(CH$_2$CH$_2$O)$_m$—CH$_2$CH$_2$OH, and —(CH$_2$CH$_2$O)$_m$—CH$_2$CH$_2$O—Y, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

31. An ionized intact duplex, comprising a mass-modified tag probe bound to a tag sequence present within a base-specifically terminated nucleic acid fragment, wherein: the mass-modified tag probe comprises at least one mass-modified nucleotide; and the tag probe is mass-modified with a mass-modifying functionality (M) selected from the group consisting of XR, F, Cl, Br, I, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$, wherein X is selected from the group consisting of —O—, —NH—, —S—, —NHC(S)—, —OCO$(CH_2)_r$COO— (where r=1–20), —NHCO$(CH_2)_r$COO— (where r=1–20), —OSO$_2$O— and —OP(O-Alkyl)O— and R is selected from the group consisting of H, methyl, ethyl, propyl, isopropyl, t-butyl, hexyl, benzyl, benzhydryl, halogen, trityl, substituted trityl, aryl, substituted aryl, (—NH$(CH_2)_r$NHCO$(CH_2)_r$CO—$)_m$—NH—$(CH_2)_r$—NH—CO—$(CH_2)_r$—COOH, (—NHCH$_2)_r$CO—$)_m$—NH—$(CH_2)_r$—COOH, (—O$(CH_2)_r$CO—$)_m$—O—$(CH_2)_r$—COOH, —Si(Y)$_3$, —(NHCHaaCO—$)_m$—NHCHaaCOOH, —(CH$_2$CH$_2$O)$_m$—CH$_2$CH$_2$OH, and —(CH$_2$CH$_2$O)$_m$—CH$_2$CH$_2$O—Y, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

32. An ionized intact duplex, comprising a mass-modified tag probe bound to a tag sequence present within a base-specifically terminated nucleic acid fragment, wherein: the mass-modified tag probe comprises at least one mass-modified nucleotide; and the tag probe is mass-modified with a mass-modifying functionality (M) selected from the group consisting of XR, F, Cl, Br, i, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$, wherein X is selected from the group consisting of —O—, —NH—, —S—, —NHC(S)—, —OCO$(CH_2)_r$COO— (where r=1–20), —NHC(O), —CONH—, —NH—C(S)—NH—, —NHCO$(CH_2)_r$COO— (where r=1–20), —OSO$_2$O—, —O—CO—CH$_2$—S— and —OP(O-Alkyl)O— and R is selected from the group consisting of H, N$_3$, methyl, ethyl, propyl, isopropyl, t-butyl, hexyl, benzyl, benzhydryl, halogen, trityl, substituted trityl, aryl, substituted aryl, $(CH_2)_m$—CH$_2$—OH, $(CH_2)_m$—CH$_2$—O—Y, $(CH_2CH_2NH)_m$—CH$_2$—CH$_2$—NH$_2$, —(NH$(CH_2)_r$NHCO$(CH_2)_r$CO—$)_m$—NH—$(CH_2)_r$—NH—CO—$(CH_2)_r$—COOH, —(NH$(CH_2)_r$CO—$)_m$—NH—$(CH_2)_r$—COOH, —(NH—CHY—CO)m—NH—CHY—COOH, (—O$(CH_2)_r$CO—$)_m$—O—$(CH_2)_r$—COOH, —Si(Y)$_3$, —(NHCHaaCO—$)_m$—NHCHaaCOOH, CH$_2$F, CHF$_2$, CF$_3$, —(CH$_2$CH$_2$O)$_m$—CH$_2$CH$_2$OH, and —(CH$_2$CH$_2$O)$_m$—CH$_2$CH$_2$O—Y, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

33. An ionized intact duplex, comprising a mass-modified tag probe bound to a tag sequence present within a base-specifically terminated nucleic acid fragment, wherein: the mass-modified tag probe comprises at least one mass-modified nucleotide; and one or more mass-modifying functionalities (M) incorporated into the tag probe are generated from one or more precursor functionalities (PF) attached to the tag probe, and wherein the precursor functionalities (PF) are selected from a group consisting of —N$_3$, —NH$_2$, —SH, —NCS, —OCO$(CH_2)_r$COOH (where r=1–20), —NHCO$(CH_2)_r$COOH (where r=1–20), —OSO$_2$OH, —OCO$(CH_2)_r$I (where r=1–20), and —OP(O-Alkyl)N(Alkyl)$_2$.

34. An ionized intact duplex, comprising a mass-modified tag probe bound to a tag sequence present within a base-specifically terminated nucleic acid fragment, wherein: the mass-modified tag probe comprises at least one mass-modified nucleotide; and one or more mass-modifying functionalities (M) incorporated into the tag probe are generated from one or more precursor functionalities (PF) attached to the tag probe, and wherein the precursor functionalities (PF) are selected from a group consisting of $—N_3$, $—NH_2$, $—SH$, $—NCS$, $—OCO(CH_2)_rCOOH$ (where r=1–20), $—NHCO(CH_2)_rCOOH$ (where r=1–20), $—OSO_2OH$, $—OCO(CH_2)_rI$ (where r=1–20), $—CONH_2$, $—NH—C(S)—NH_2$, $OP(O-Alkyl)OH$, and $O—CO—CH_2—SH$.

35. An ionized intact mass-modified nucleic acid molecule, comprising at least one mass modified nucleotide, wherein a mass-modifying functionality (M) incorporated into the molecule is generated from a precursor functionality (PF) attached to one or more of a nucleic acid primer, a chain-elongating nucleoside triphosphate or a chain-terminating nucleoside triphosphate, and wherein the precursor functionality (PF) is selected from a group consisting of $—N_3$, $—NH_2$, $—SH$, $—NCS$, $—OCO(CH_2)_rCOOH$ (where r=1–20), $—NHCO(CH_2)_rCOOH$ (where r=1–20), $—OSO_2OH$, $—OCO(CH_2)_rI$ (where r=1–20), $—CONH_2$, $—NH—C(S)—NH_2$, $OP(O-Alkyl)OH$, and $O—CO—CH_2—SH$.

36. An ionized intact mass-modified nucleic acid molecule, comprising at least two mass modified nucleotides, wherein a mass-modifying functionality (M) incorporated into the molecule is XR, wherein X is selected from the group consisting of $—O—$, $—NH—$, $—S—$, $—NHC(S)—$, $—OCO(CH_2)_rCOO—$ (where r=1–20), $—NHCO(CH_2)_rCOO—$ (where r=1–20), $—OSO_2O—$ and $—OP(O-Alkyl)O—$ and R is selected from the group consisting of H, methyl, ethyl, propyl, isopropyl, t-butyl, hexyl, benzyl, benzhydryl, halogen, trityl, substituted trityl, aryl, substituted aryl, $(—NH(CH_2)_rNHCO(CH_2)_rCO—)_m—NH—(CH_2)_r—NH—CO—(CH_2)_r—COOH$, $(—NH(CH_2)_rCO—)_m—NH—(CH_2)_r—COOH$, $(—O(CH_2)_rCO—)_m—O—(CH_2)_r—COOH$, $—Si(Y)_3$, $—(NHCHaaCO—)_m—NHCHaaCOOH$, $—(CH_2CH_2O)_m—CH_2CH_2OH$, and $—(CH_2CH_2O)_m—CH_2CH_2O—Y$, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

37. An ionized intact mass-modified nucleic acid molecule, comprising at least two mass modified nucleotides, wherein a mass-modifying functionality (M) incorporated into the molecule is XR, wherein X is selected from the group consisting of $—O—$, $—NH—$, $—S—$, $—NHC(S)—$, $OCO(CH_2)_rCOO—$ (where r=1–20), $—NHC(O)$, $—CONH—$, $—NH—C(S)—NH—$, $—NHCO(CH_2)_rCOO—$ (where r==1–20), $—OSO_2O—$, $—O—CO—CH_2—S—$ and $—OP(O-Alkyl)O—$ and R is selected from the group consisting of H, $N_3$, methyl, ethyl, propyl, isopropyl, t-butyl, hexyl, benzyl, benzhydryl, halogen, trityl, substituted trityl, aryl, substituted aryl, $(CH_2)_m—CH_2—OH$, $(CH_2)_m—CH_2—O—Y$, $(CH_2CH_2NH)_m—CH_2—CH_2—NH_2$, $—(NH(CH_2)_rNHCO(CH_2)_rCO—)_m—NH—(CH_2)_r—NH—CO—(CH_2)_r—COOH$, $—(NH(CH_2)_rCO—)_m—NH—(CH_2)_r—COOH$, $—(NH—CHY—CO)_m—NH—CHY—COOH$, $(—O(CH_2)_rCO—)_m—O—(CH_2)_r—COOH$, $—Si(Y)_3$, $—(NHCHaaCO—)_m—NHCHaaCOOH$, $CH_2F$, $CHF_2$, $CF_3$, $—(CH_2CH_2O)_m—CH_2CH_2OH$, and $—(CH_2CH_2O)_m—CH_2CH_2O—Y$, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

38. The set of mass-differentiated tag probes of claim 12, wherein one or more mass-modifying functionalities incorporated into the probes are generated from a precursor functionality (PF) attached to the mass-differentiated tag probes, and wherein the precursor functionalities are selected from the group consisting of $—N_3$, $—NH_2$, $—SH$, $—NCS$, $—OCO(CH_2)_rCOOH$ (where r=1–20), $—NHCO(CH_2)_rCOOH$ (where r=1–20), $—OSO_2OH$, $—OCO(CH_2)_rI$ (where r=1–20), $—CONH_2$, $—NH—C(S)—NH_2$, $OP(O-Alkyl)OH$, and $O—CO—CH_2—SH$.

39. The set of mass-differentiated tag probes of claim 12, wherein the tag probes are mass-modified with a mass-modifying functionality (M) selected from the group consisting of XR, F, Cl, Br, I, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$, wherein X is selected from the group consisting of $—O—$, $—NH—$, $—S—$, $—NHC(S)—$, $—OCO(CH_2)_rCOO—$ (where r=1–20), $—NHCO(CH_2)_rCOO—$ (where r=1–20), $—OSO_2O—$ and $—OP(O-Alkyl)O—$ and R is selected from the group consisting of H, $N_3$, methyl, ethyl, propyl, isopropyl, t-butyl, hexyl, benzyl, benzhydryl, halogen, trityl, substituted trityl, aryl, substituted aryl, $(—NH(CH_2)_rNHCO(CH_2)_rCO—)_m—NH—(CH_2)_r—NH—CO—(CH_2)_r—COOH$, $(—NH(CH_2)_rCO—)_m—NH—(CH_2)_r—COOH$, $(—O(CH_2)_rCO—)_m—O—(CH_2)_r—COOH$, $—Si(Y)_3$, $—(NHCHaaCO—)_m—NHCHaaCOOH$, $—(CH_2CH_2O)_m—CH_2CH_2OH$, and $—(CH_2CH_2O)_m—CH_2CH_2O—Y$, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

40. The set of mass-differentiated tag probes of claim 12, wherein the tag probes are mass-modified with a mass-modifying functionality (M) selected from the group consisting of XR, F, Cl, Br, I, $Si(CH_3)_3$, $Si(CH_3)_2(C_2H_5)$, $Si(CH_3)(C_2H_5)_2$, $Si(C_2H_5)_3$, $CH_2F$, $CHF_2$, and $CF_3$, wherein X is selected from the group consisting of $—O—$, $—NH—$, $—S—$, $—NHC(S)—$, $—OCO(CH_2)_rCOO—$ (where r=1–20), $—NHC(O)$, $—CONH—$, $—NH—C(S)—NH—$, $—NHCO(CH_2)_rCOO—$ (where r=1–20), $—OSO_2O—$, $—O—CO—CH_2—S—$ and $—OP(O-Alkyl)O—$ and R is selected from the group consisting of H, $N_3$, methyl, ethyl, propyl, isopropyl, t-butyl, hexyl, benzyl, benzhydryl, halogen, trityl, substituted trityl, aryl, substituted aryl, $(CH_2)_m—CH_2—OH$, $(CH_2)_m—CH_2—O—Y$, $(CH_2CH_2NH)_m—CH_2—CH_2—NH_2$, $—(NH(CH_2)_rNHCO(CH_2)_rCO—)_m—NH—(CH_2)_r—NH—CO—(CH_2)_r—COOH$, $—(NH(CH_2)_r CO—)_m—NH—(CH_2)_r—COOH$, $—(NH—CHY—CO)m—NH—CHY—COOH$, $(—O(CH_2)_rCO—)_m—O—(CH_2)_r—COOH$, $—Si(Y)_3$, $—(NHCHaaCO—)_m—NHCHaaCOOH$, $CH_2F$, $CHF_2$, $CF_3$, $—(CH_2CH_2O)_m—CH_2CH_2OH$, and $—(CH_2CH_2O)_m—CH_2CH_2O—Y$, where m is in the range of 0 to 200, Y is a lower alkyl group selected from a group consisting of methyl, ethyl, propyl, isopropyl, t-butyl and hexyl, r is in the range of 1 to 20, and aa represents the amino acid side chain of a naturally occurring amino acid.

41. An intact positively charged ionized and volatilized mass-modified nucleic acid molecule, comprising at least one mass-modified nucleotide selected from the group consisting of a mass-modified 2'-deoxynucleotide, a mass-modified 2',3'-dideoxynucleotide and a mass-modified 3'-deoxynucleotide.

42. An intact ionized and volatilized mass-modified nucleic acid molecule, comprising at least two mass modified nucleotides.

* * * * *

UNITED STATES PATENT AND TRADEMARK OFFICE
CERTIFICATE OF CORRECTION

PATENT NO. : 6,225,450 B1
DATED : May 1, 2001
INVENTOR(S) : Köster, H.

It is certified that error appears in the above-identified patent and that said Letters Patent is hereby corrected as shown below:

Column 2,
Line 25, please replace "sulphur" with -- sulfur --

Column 3,
Line 51, please replace "amplifyable" with -- amplifiable --

Figure 8A:
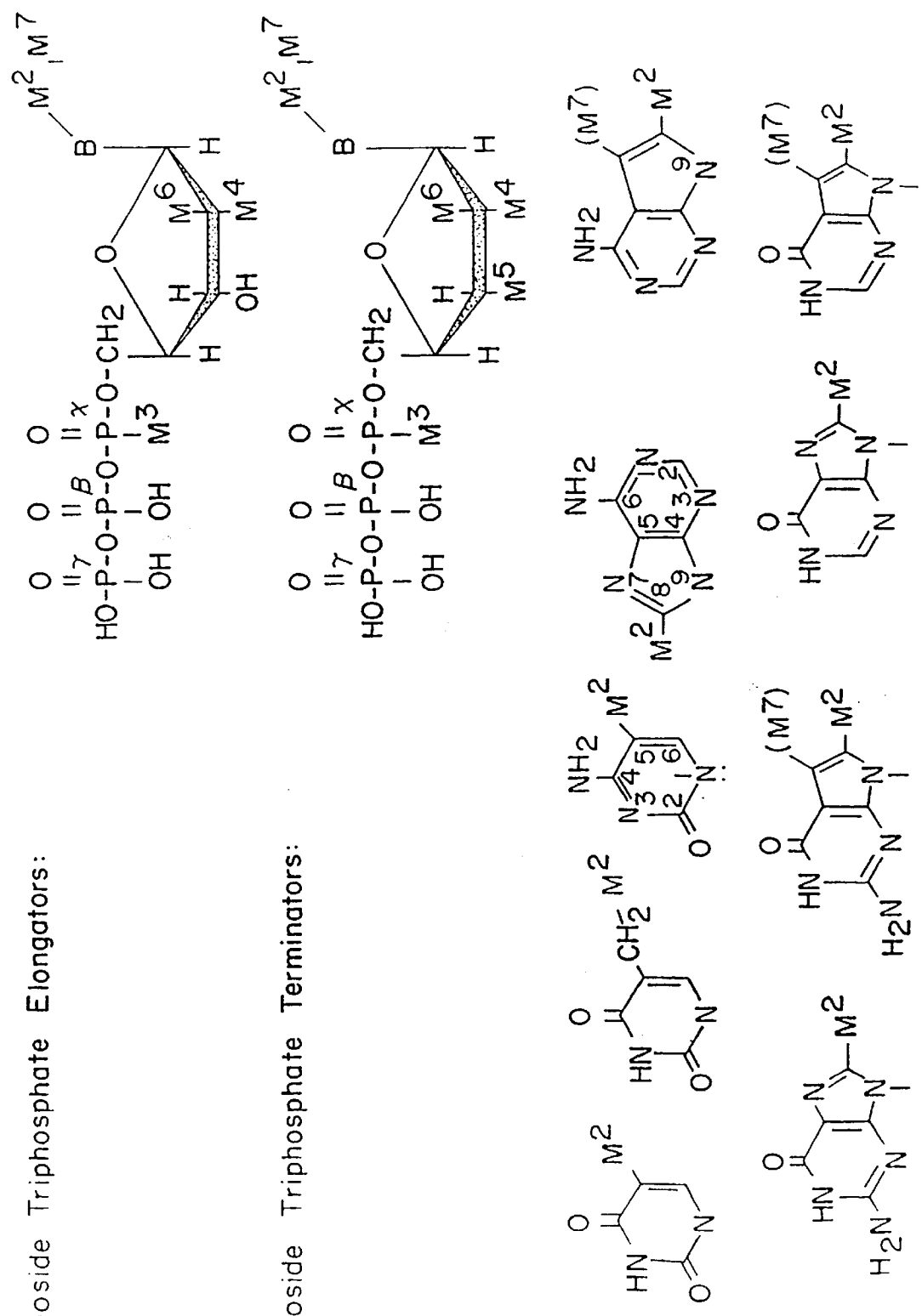
Figure 17A:
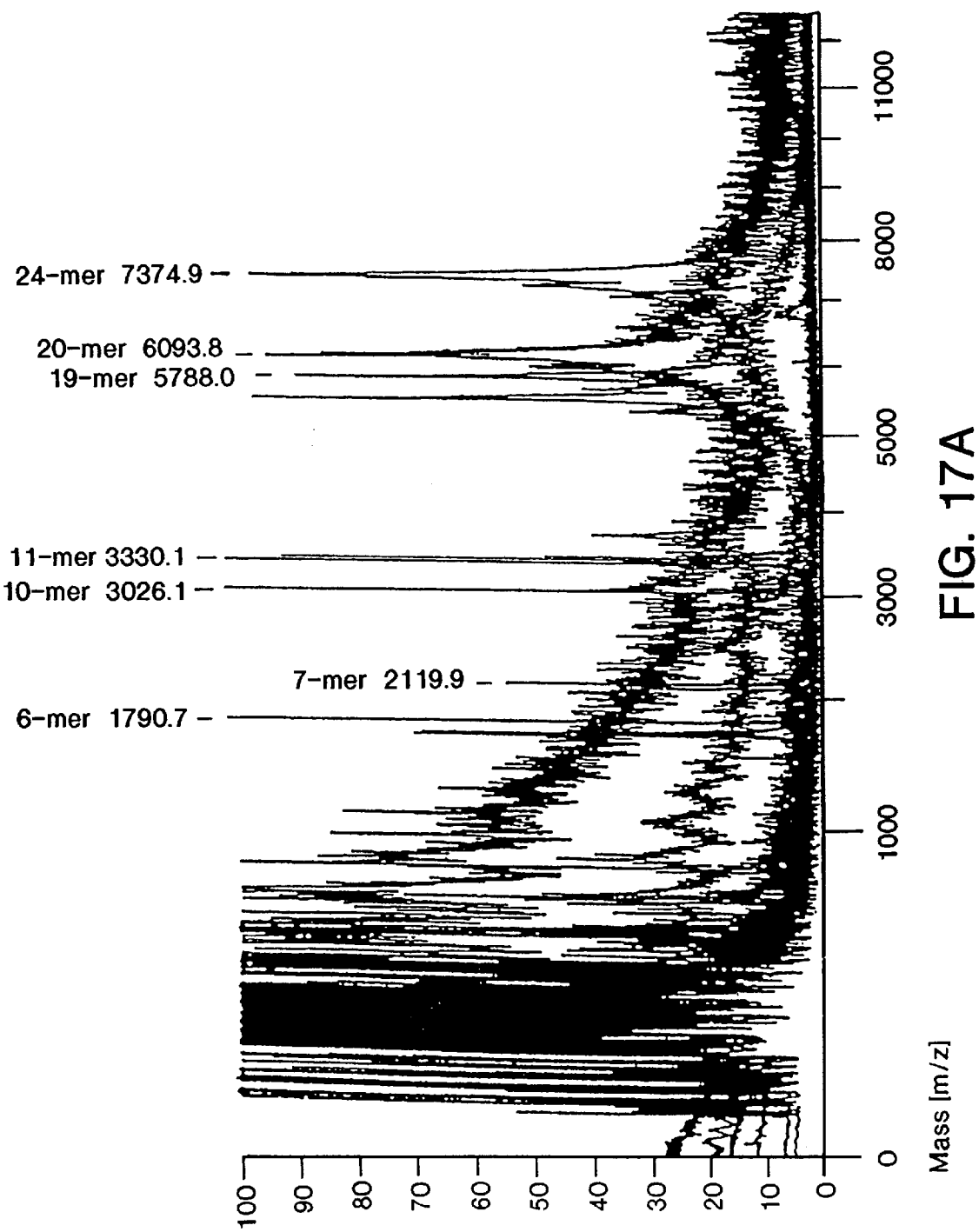
FIG. 17 shows the superposition of the spectra of FIG. 16A–16M. The two panels show two different scales and the spectra analyzed at that scale.
Figure 17B:
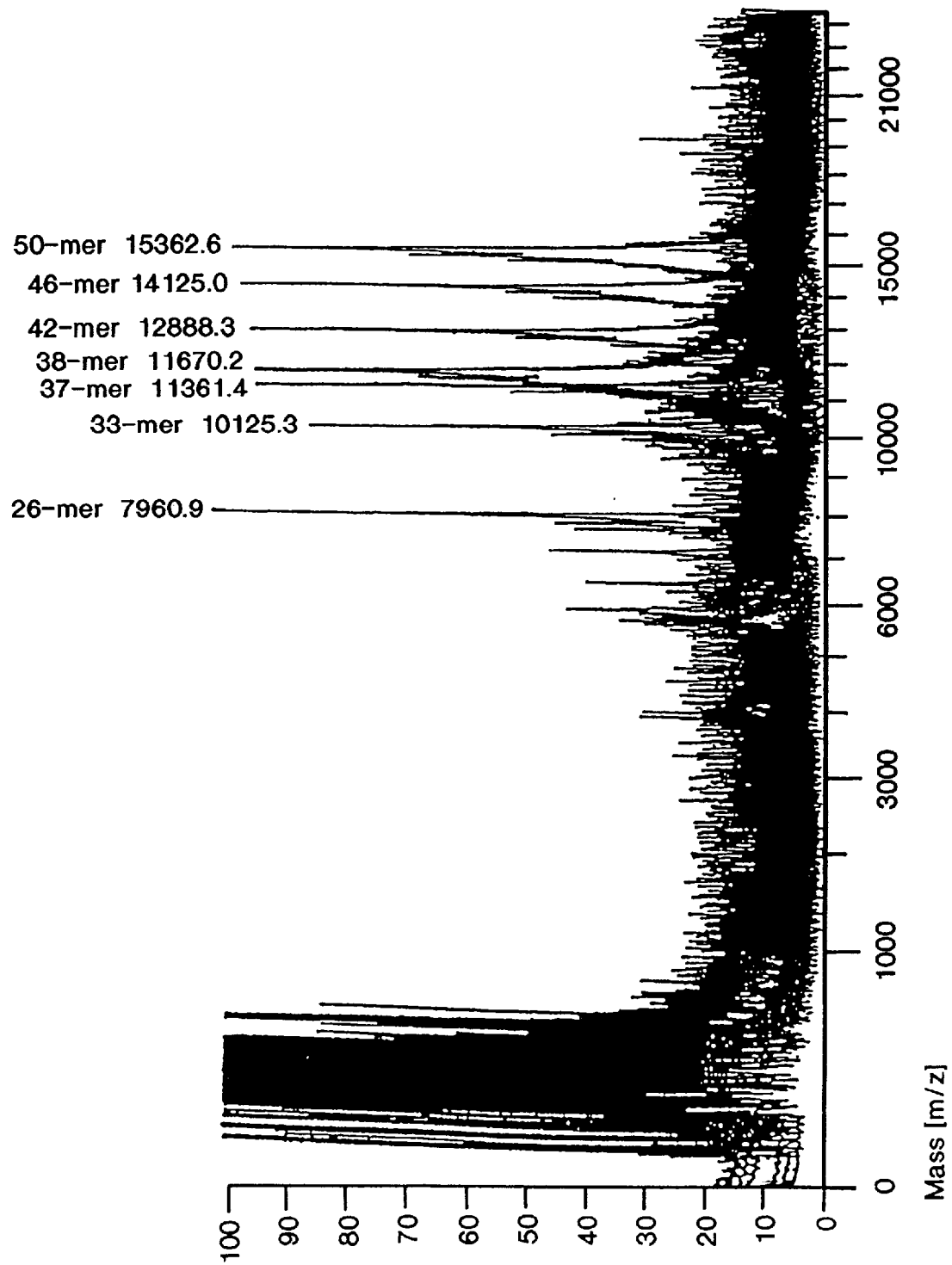

Column 9,
Line 24, please replace "FIG. 8" with -- FIGS. 8A and 8B --
Line 36, please replace "d(pT) $_{12-18}$." with -- d(pT)$_{12-18}$. --
Line 43, please replace "2" with -- 2A --
Line 45, please replace -- "FIG. 17" with -- FIGS. 17A and 17B --

Column 10,
Line 49, please replace "ribonucelotides" with -- ribonucleotides --

Column 12,
Line 22, please replace "FIG. 20" with -- FIGS. 20A and 20B --

Column 13,
Line 5, please replace " akyliodides" with -- alkyliodides --
Line 17, please replace "dithioerythrol" with -- dithioerythritol --

Column 22,
Line 63, please replace "propanaol" with -- propanol --

Column 14,
Line 61, please replace "FIG. 16" with -- FIGS, 16A-16M --
Line 62, please replace "2" with -- 2A-2B --
Line 63, please replace " FIG. 17" with -- FIGS. 17A-17B --

Column 15,
Line 36, please replace "7" with -- 7A --
Line 52, please replace "7" with -- 7B --

Column 16,
Line 7, plesase replace "FIG. 8" with -- FIGS. 8A-8B --

Column 17,
Line 22, please replace "7" with -- 7A-7B --

UNITED STATES PATENT AND TRADEMARK OFFICE
CERTIFICATE OF CORRECTION

PATENT NO. : 6,225,450 B1
DATED : May 1, 2001
INVENTOR(S) : Köster, H.

Figure 7A:
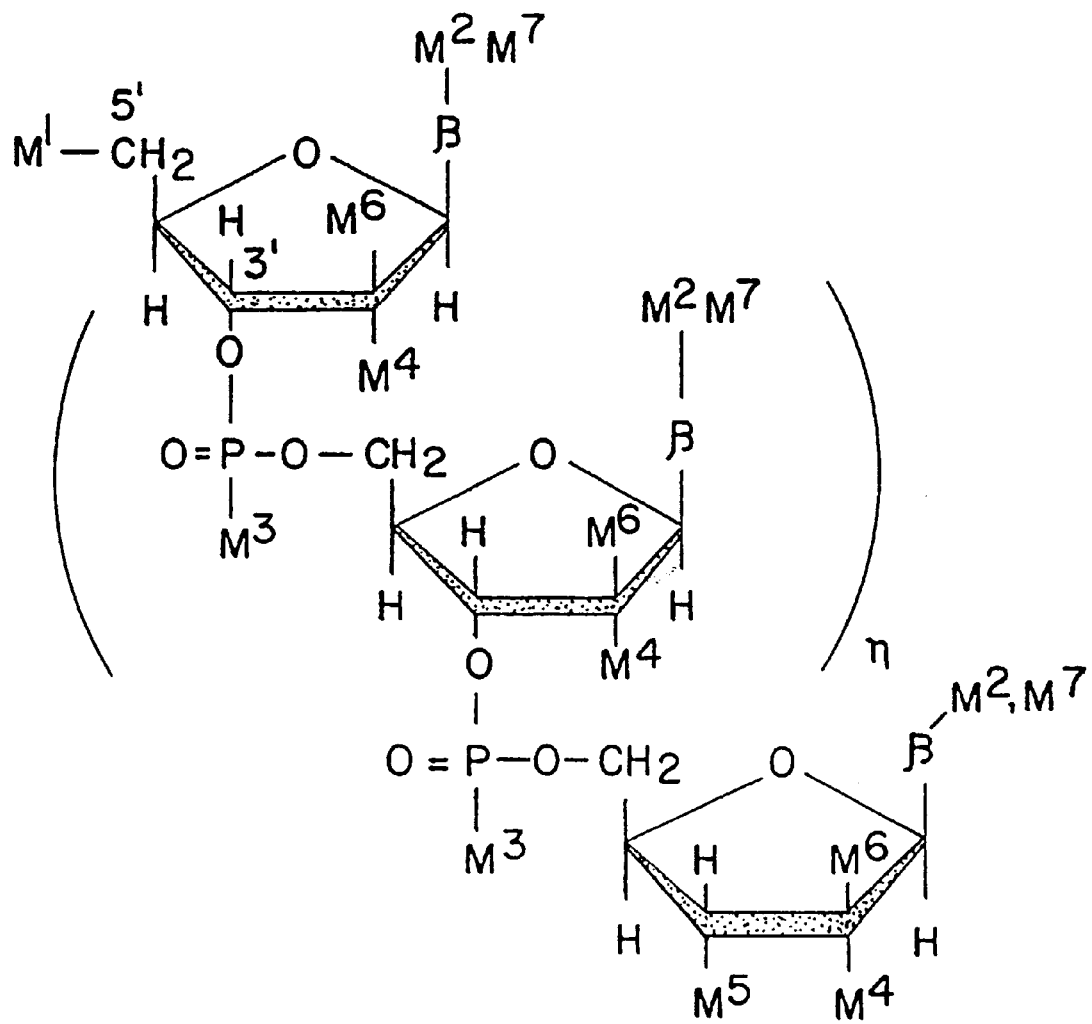

It is certified that error appears in the above-identified patent and that said Letters Patent is hereby corrected as shown below:

Column 19,
Line 33 and 53, please replace "7" with -- FIGS. 7A-7B --

Column 20,
Line 3, please replace "7" with -- FIGS. 7A-7B --

Column 22,
Line 63, please replace "propanaol" with -- propanol --

Column 32,
Line 2, please replace "pmoles/)" with -- pmoles/ --
Line 54, please replace "FIG. 16" with -- FIGS. 16A-16M --
Line 59, please replace "FIG. 17" with -- FIGS. 17A-17B --
Line 61, please replace "upper panel" with -- FIG. 17A --
Line 62, please replace " lower panel" with -- FIG. 17B --

Column 33,
Line 3, please replace "1 7-mers" with -- 17-mers --
Line 5, please replace " 7-mers" with -- 17-mers --

Claims
Please delete 3 and 5, and replace them with the following claims:

-- 3. An intact ionized mass-modified nucleic acid molecule of claim 131, comprising at least two mass-modified nucleotides containing a mass-modifying functionality (M) attached to a heterocyclic base of the nucleotide. --

UNITED STATES PATENT AND TRADEMARK OFFICE
CERTIFICATE OF CORRECTION

PATENT NO. : 6,225,450 B1
DATED : May 1, 2001
INVENTOR(S) : Köster, H.

It is certified that error appears in the above-identified patent and that said Letters Patent is hereby corrected as shown below:

<u>Claims cont'd.</u>

-- 5. An intact ionized mass-modified nucleic acid molecule of claim 131, comprising at least two mass-modified nucleotides containing a mass-modifying functionality (M) attached to at least one phosphorus of the nucleotide. --

Signed and Sealed this

Ninth Day of April, 2002

Attest:

JAMES E. ROGAN
*Director of the United States Patent and Trademark Office*

*Attesting Officer*

```
                       SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
          (A) LENGTH: 14 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: YES (xi) SEQUENCE DESCRIPTION: SEQ ID NO:1:

CATGCCATGG CATG                                                        14

(2) INFORMATION FOR SEQ ID NO:2:

(i) SEQUENCE CHARACTERISTICS:
          (A) LENGTH: 21 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: YES (xi) SEQUENCE DESCRIPTION: SEQ ID NO:2:

AAATTGTGCA CATCCTGCAG C                                                21

(2) INFORMATION FOR SEQ ID NO:3:

(i) SEQUENCE CHARACTERISTICS:
          (A) LENGTH: 50 base pairs
          (B) TYPE: nucleic acid
          (C) STRANDEDNESS: single
          (D) TOPOLOGY: linear (ii) MOLECULE TYPE: other nucleic acid (iii) HYPOTHETICAL: YES (xi) SEQUENCE DESCRIPTION: SEQ ID NO:3:
```

```
                                    -continued

TAACGGTCAT TACGGCCATT GACTGTAGGA CCTGCATTAC ATGACTAGCT                       50

(2) INFORMATION FOR SEQ ID NO:4:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:4:

TAAAACGACG GGCCAGNG                                                         18

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: YES (xi) SEQUENCE DESCRIPTION: SEQ ID NO:5:

NAAAACGACG GGCCAGNG                                                         18
```